US010342801B2

(12) United States Patent
Alargova et al.

(10) Patent No.: US 10,342,801 B2
(45) Date of Patent: Jul. 9, 2019

(54) PLATINUM COMPOUNDS, COMPOSITIONS, AND USES THEREOF

(71) Applicant: PLACON THERAPEUTICS, INC., Watertown, MA (US)

(72) Inventors: Rossitza G. Alargova, Brighton, MA (US); Mark T. Bilodeau, Waltham, MA (US); Richard Wooster, Natick, MA (US); Benoît Moreau, Newton, MA (US); Kerry Whalen, Waltham, MA (US); J. Michael Ramstack, Lunenburg, MA (US); Danielle N. Rockwood, Medford, MA (US); Patrick Lim Soo, Ridgewood, NJ (US); Sukhjeet Singh, Lexington, MA (US); Tsun P. Au Yeung, Watertown, MA (US); Charles-Andre Lemelin, North Chelmsford, MA (US); Linda M. Custer, Waltham, MA (US)

(73) Assignee: PLACON THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/737,064

(22) PCT Filed: Jun. 22, 2016

(86) PCT No.: PCT/US2016/038699
§ 371 (c)(1),
(2) Date: Dec. 15, 2017

(87) PCT Pub. No.: WO2016/209918
PCT Pub. Date: Dec. 29, 2016

(65) Prior Publication Data
US 2018/0243318 A1    Aug. 30, 2018

Related U.S. Application Data

(60) Provisional application No. 62/268,666, filed on Dec. 17, 2015, provisional application No. 62/183,403, filed on Jun. 23, 2015.

(51) Int. Cl.
*A61K 31/555* (2006.01)
*A61K 9/00* (2006.01)
(Continued)

(52) U.S. Cl.
CPC .......... *A61K 31/555* (2013.01); *A61K 9/0019* (2013.01); *A61K 9/08* (2013.01);
(Continued)

(58) Field of Classification Search
None
See application file for complete search history.

(56) References Cited

U.S. PATENT DOCUMENTS

| 2011/0159111 A1 | 6/2011 | Curry et al. |
| 2014/0193334 A1 | 7/2014 | Bierbach et al. |

FOREIGN PATENT DOCUMENTS

| WO | 2014/100417 A1 | 6/2014 |
| WO | 2015/102922 A1 | 7/2015 |

(Continued)

OTHER PUBLICATIONS

Pitchler, V. et al., "Maleimide-functionalised platinum(IV) complexes as a synthetic platform for targeted drug delivery" (2013) Chem. Commun. 49:2249-2251.
(Continued)

*Primary Examiner* — Karl J Puttlitz
(74) *Attorney, Agent, or Firm* — DT Ward, PC; Donna T. Ward; Heng Zhu

(57) ABSTRACT

The present teachings relate to compounds and compositions for treatment of cancers. In some embodiments, the composition comprises a platinum (IV) complex having at least one reacting group for reacting with a functional group on a protein.

8 Claims, 13 Drawing Sheets

(51) Int. Cl.
  *A61K 47/02*  (2006.01)
  *A61K 47/26*  (2006.01)
  *A61P 35/00*  (2006.01)
  *A61K 9/08*  (2006.01)
  *A61K 31/4015*  (2006.01)

(52) U.S. Cl.
  CPC .......... *A61K 31/4015* (2013.01); *A61K 47/02* (2013.01); *A61K 47/26* (2013.01); *A61P 35/00* (2018.01)

(56) References Cited

FOREIGN PATENT DOCUMENTS

| WO | 2015102922 | * | 7/2015 |
| WO | 2015/200250 A1 | | 12/2015 |
| WO | 2015200250 | * | 12/2015 |

OTHER PUBLICATIONS

International Search Report and Written Opinion dated Sep. 13, 2016, in application No. PCT/US2016/038699, entitled: Platinum Compounds, Compositions, and Uses Thereof.

Moreau, B. et al. "Abstract 4484:BTP-114: An albumin binding cisplatin prodrug with improved and sustained tumor growth inhibition" (2015) Proceedings: 106th Annual Meeting of the American Association for Cancer Research Apr. 18-22, 2015 Philadelphia, PA / Cancer Research 75: Issue 15 Supplemental Abstract No. 4494.

Supplemental European Search Report dated Jan. 28, 2019 in co-pending European application No. 16815194.2, entitled "Platinum Compounds, Compositions, and Uses Thereof".

* cited by examiner

Figure 14-1

| | | Treatment Period / Cycle / Day (Visit Window) | | | | | | | | | |
|---|---|---|---|---|---|---|---|---|---|---|---|
| | | Treatment Period | | | | | | | | | |
| | Screen-ing | C1 | | | | Subsequent Even Cycles (C2, C4, etc.) | | | Subsequent Odd Cycles (C3, C5, etc.) | | EOT |
| Evaluation / Procedure | D-14 to -1 | D1 | D 3 or 4 | D8 | D15 | D1 | D8 | D15 | D1 | D8 | D15 | D+30[3] |
| Window | - | - | - | ±1d | ±1d | ±1d | ±2d | ±2d | ±1d | ±2 | ±2d | ±3 d |
| Baseline Evaluations | | | | | | | | | | | | |
| Written informed consent | X | | | | | | | | | | | |
| Demographics | X | | | | | | | | | | | |
| Height | X | | | | | | | | | | | |
| Medical history | X | X | | | | | | | | | | |
| Cancer diagnosis and history, including DNA repair mutation status and all prior systemic and radiation therapies and surgeries | X | X | | | | | | | | | | |
| Screening serologies[1] | X | | | | | | | | | | | |
| Review of entrance criteria | X | X | | | | | | | | | | |
| Study Drug Administration | | | | | | | | | | | | |
| Pre-hydration, per institutional practice, diuretics and anti-emetics | | X | | | | X | | | X | | | |
| Verify urine output (>100 mL) | | X | | | | X | | | X | | | |
| Compound 8 administration | | X | | | | X | | | X | | | |
| Post-hydration | | X | | | | X | | | X | | | |

| Evaluation / Procedure | | Screening D-24 to -1 | C1 | | | | | Subsequent Even Cycles (C2, C4, etc.) | | | | Subsequent Odd Cycles (C3, C5, etc.) | | | EOT |
|---|---|---|---|---|---|---|---|---|---|---|---|---|---|---|---|
| | | | D1 | D 3 or 4 | D8 | D15 | D22 | D1 | D8 | D15 | D22 | D1 | D8 | D15 | D>99 |
| | Window | - | - | - | ±1d | ±1d | ±1d | ±1d | ±1d | ±1d | ±1d | ±1d | ±1d | ±1d | ±1d |
| Pharmacokinetics (PK) | | | | | | | | | | | | | | | |
| Blood sample collections for PK | | | X$^p$ | X$^p$ | X$^p$ | X$^p$ | X$^p$ | X$^p$ | | | | | | | |
| Additional Evaluations in Expansion Cohort(s) | | | | | | | | | | | | X$^p$ | | | X |
| Tumor markers$^{aa}$ | | X | | | | | | | | | | | | | X |

PLATINUM COMPOUNDS, COMPOSITIONS, AND USES THEREOF

CROSS REFERENCE TO RELATED APPLICATIONS

This application is a 35 U.S.C. § 371 U.S. National Stage Entry of International Application No. PCT/US2016/038699, entitled, "PLATINUM COMPOUNDS, COMPOSITIONS, AND USES THEREOF, filed Jun. 22, 2016, which claims the benefit of priority of U.S. Provisional Patent Application No. 62/183,403, filed Jun. 23, 2015, entitled PLATINUM COMPOUNDS, COMPOSITIONS, AND USES THEREOF, and U.S. Provisional Patent Application No. 62/268,666, filed Dec. 17, 2015, entitled PLATINUM COMPOUNDS, COMPOSITIONS, AND USES THEREOF, the contents of each of which are herein incorporated by reference in their entirety.

FIELD OF THE INVENTION

The invention relates to platinum based compounds.

BACKGROUND OF THE INVENTION

Platinum-based drugs are among the most active and widely used anticancer agents. Cisplatin is one of the few FDA-approved, platinum-based cancer chemotherapeutics. Although cisplatin is effective against a number of solid tumors, especially testicular, bladder and ovarian cancer, its clinical use has been limited because of its toxic effects as well as the intrinsic and acquired resistance of some tumors to this drug.

To overcome these limitations, platinum analogs with lower toxicity and greater activity in cisplatin-resistant tumors have been developed and tested, resulting in the approval of carboplatin and oxaliplatin in the United States. For example, carboplatin has the advantage of being less nephrotoxic, but its cross-resistance with cisplatin has limited its application in otherwise cisplatin-treatable diseases.

Oxaliplatin, however, exhibits a different anticancer spectrum from that of cisplatin. It has been approved as the first or second line therapy in combination with 5-fluorouracil/leucovorin for advanced colorectal cancer, for which cisplatin and carboplatin are essentially inactive. These platinum drugs have platinum in the 2+ oxidative state (Pt(II)) and are not orally active.

Platinum complexes in the 4+ oxidative state (Pt(IV) complexes) provide several advantages. Platinum(IV) complexes are substantially inactive in the 4+ oxidation state but become activated upon reduction to the platinum(II) state. As such Pt(IV) complexes constitute prodrugs of Pt(II) drugs that are activated in tumor cells. The two additional coordination sites (the axial sites) can also be modified to change the pharmacokinetic properties of the complexes. For example, the two axial sites, as well as the four equatorial sites, can include ligands that have a Michael acceptor. The inclusion of a Michael acceptor as disclosed in the present teachings may increase the Pt concentration in tumor cells and, in certain instances, may increase the efficacy in treating a disease or a condition discussed herein. In certain instances, Pt(IV) complexes of the present teachings can be orally active and/or have a reduced long-term toxicity.

SUMMARY OF THE INVENTION

The present teachings relate to compositions, for example, for reducing, disrupting, or inhibiting the growth of a cancer cell or inducing the death of a cancer cell.

The composition can include a platinum (IV) compound. In various embodiments, the platinum (IV) compound includes a suitable reacting group for reacting with a functional group on a protein. Such compounds are referred to herein as Pt(IV)M. The reacting group may be a Michael acceptor. For example, a Michael acceptor can be introduced by a ligand. In various embodiments, one of or both the axial ligands each comprises one or more Michael acceptors.

The present teachings also provide compositions including a compound as described herein and methods of using a compound or a composition as described herein. In various embodiments, the methods of the present teachings are useful for the prevention or treatment of diseases that benefit from increased cell death or decreased cell proliferation. For example, the method of the present teachings can be used to increase cancer cell death or decrease cancer cell proliferation. The increased cancer cell death or decreased cancer proliferation can occur, for example, outside the body (ex vivo) or inside the body (in vivo).

Certain embodiments of the present teachings also provide for use of a compound as described herein as a medicament for treating or preventing a disease and/or in the manufacture of such a medicament, e.g., for use in the treatment of a disease. Some embodiments provide the use of a compound as described herein for use as a medicament. In certain embodiments, the teachings provide a compound or composition as described herein for the treatment of disease, e.g. for the treatment of a cancer. In certain embodiments, the teachings provide a compound or composition as described herein for the treatment of a tumor, wherein the tumor cells express one or more KRAS mutations.

BRIEF DESCRIPTION OF DRAWINGS

FIGS. 14-1, 14-2 and 14-3 show schedule of events in Example 39.

DETAILED DESCRIPTION

Figure 1:
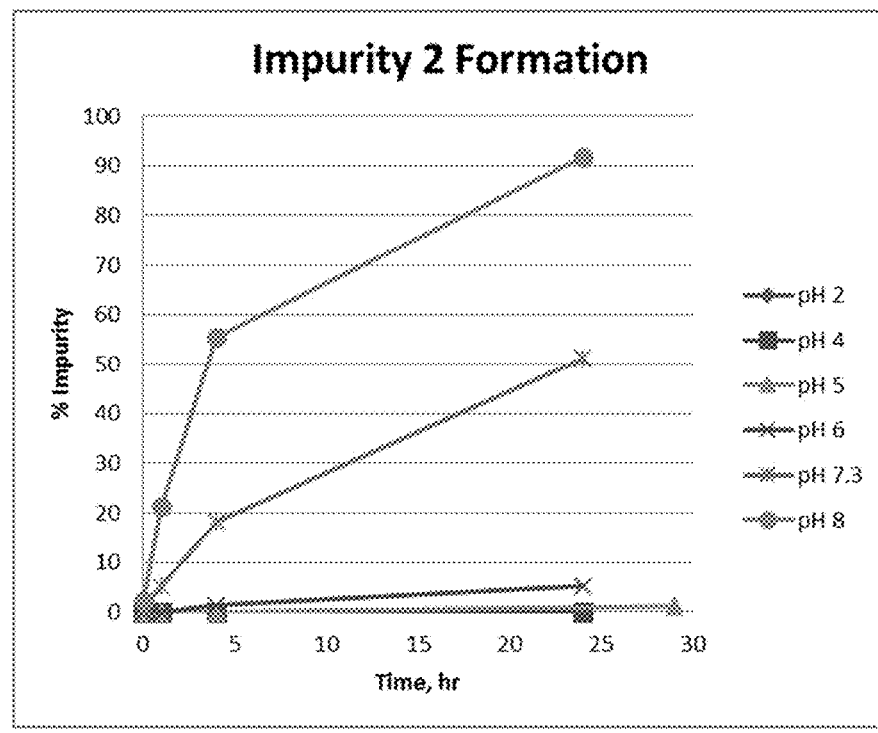
FIG. 1 shows formation of Impurity 2 in 0.1 mg/mL Compound 8 in Britton Robinson buffer at room temperature.

Applicants have discovered that Pt(IV) compounds having a suitable reacting group for reacting with a functional group on a protein are effective inhibitors of cellular proliferation and tumor growth. Such compounds are referred to herein as Pt(IV)M. In some embodiments, the protein is albumin and the Pt(IV)M compounds do not comprise albumin. The reacting group may be a Michael acceptor. In some embodiments, the Pt(IV)M compounds comprise a monomaleimide.

A feature of these compounds is their relatively low toxicity to an organism while maintaining efficacy at inhibiting, e.g., slowing or stopping tumor growth. As used herein, "toxicity" refers to the capacity of a substance or composition to be harmful or poisonous to a cell, tissue organism or cellular environment. Low toxicity refers to a reduced capacity of a substance or composition to be harmful or poisonous to a cell, tissue organism or cellular environment. Such reduced or low toxicity may be relative to a standard measure, relative to a treatment or relative to the absence of a treatment.

Toxicity may further be measured relative to a subject's weight loss where weight loss over 15%, over 20% or over 30% of the body weight is indicative of toxicity. Other metrics of toxicity may also be measured such as patient presentation metrics including lethargy and general malaise. Neutropenia or thrombopenia may also be metrics of toxicity.

Pharmacologic indicators of toxicity include elevated AST/ALT levels, neurotoxicity, kidney damage, GI damage and the like.

Furthermore, in some embodiments, such compounds are effective for inhibiting tumor growth, whether measured as a net value of size (weight, surface area or volume) or as a rate over time, in multiple types of tumors.

In some embodiments the size of a tumor is reduced by 60% or more. In some embodiments, the size of a tumor is reduced by at least 20%, at least 30%, at least 40%, at least 50%, at least 60%, at least 70%, at least 80%, at least 90%, at least 95%, at least 96%, at least 97%, at least 98%, at least 99%, at least 100%, by a measure of weight, and/or area and/or volume.

In some embodiments, the RECIST (Response Evaluation Criteria In Solid Tumors) criteria are used to characterize the effects of the compounds of the invention on solid tumors. The guidelines for gauging tumors were updated and published in the European Journal of Cancer (EJC) in January 2009 (Eisenhauer et al., 2009, European Journal of Cancer 45: 228-247), the contents of which are incorporated herein by reference in their entirety. Any of the RECIST metrics may be used to characterize the effects of the compounds of the invention on tumors including but not limited to response, assessment and measurement criteria.

It has been surprisingly found that the relative ability of compounds of the invention to inhibit in vitro cell proliferation is not predictive of their relative ability to inhibit tumor growth, i.e., their relative ability to inhibit tumor growth is greater than their relative ability to inhibit cell proliferation in vitro.

Without wishing to be bound to any theory, the effective delivery of a Pt(IV)M compound may be related to the covalent attachment of the compound to a protein such as albumin. Conjugation to albumin prevents rapid clearance and delivers stable and inactive form of platinum to tumor sites. The compound-albumin bond may be cleaved at a tumor site, creating an active platinum compound, e.g., a Pt(II) compound. Trafficking of a Pt(IV)M compound by albumin is being studied with MIA PaCa-2 and BxPC-3 cell lines (Commisso et al., 2013, Nature, 497:633-637, the contents of which are incorporated herein by reference in their entirety).

In some embodiments, a Pt(IV)M compound as described herein is administered to a subject who has a tumor comprising cells that express one or more KRAS mutations. A subject's tumor may be assayed for KRAS mutations using methods known in the art, for example, see Anderson, 2011, Expert Rev Mol Diagn. 11:635-642 and Thierry et al., 2014, Nature Medicine 20:430-435, the contents of each of which are incorporated herein by reference in their entirety. If the tumor has a KRAS mutation, the tumor is likely to be responsive to treatment by the Pt(IV)M compounds disclosed herein. In some embodiments, the tumor is directly assayed for the presence of a KRAS mutation. In some embodiments, a non-tumor tissue, e.g., plasma DNA is assayed for the presence of a KRAS mutation.

This finding is also important because some tumors containing cells that express one or more KRAS mutants are not sensitive to certain treatments. For example, colorectal cancer patients are tested for the presence of KRAS mutations because the presence of certain of these mutations predicts resistance to therapies directed against EGFR (Siena et al., 2009, J Natl Cancer Inst 101:1308-24, the contents of which are incorporated herein by reference in their entirety). Such patients are candidates for treatments with a Pt(IV)M compound described herein.

For convenience, before further description of the present teachings, certain definitions of terms employed in the specification and claims are collected here. These definitions should be read in light of the remainder of the disclosure and as understood by a person of ordinary skill in the art. Unless defined otherwise, all technical and scientific terms used herein have the same meaning as commonly understood by a person of ordinary skill in the art.

The articles "a" and "an," as used herein, should be understood to mean "at least one," unless clearly indicated to the contrary.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements.

In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig. In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to amelioration of a disease or disorder, or at least one sign or symptom thereof. "Treatment" or "treating" can refer to reducing the progression of a disease or disorder, as determined by, e.g., stabilization of at least one sign or symptom or a reduction in the rate of progression as determined by a reduction in the rate of progression of at least one sign or symptom. In another embodiment, "treatment" or "treating" refers to delaying the onset of a disease or disorder.

As used herein, "prevention" or "preventing" refers to a reduction of the risk of acquiring or having a sign or symptom a given disease or disorder, i.e., prophylactic treatment.

The phrase "therapeutically effective amount" as used herein means that amount of a compound, material, or composition comprising a compound of the present teachings that is effective for producing a desired therapeutic effect. Accordingly, a therapeutically effective amount treats or prevents a disease or a disorder, e.g., ameliorates at least one sign or symptom of the disorder. In various embodiments, the disease or disorder is a cancer.

A dash ("—") that is not between two letters or symbols is used to indicate a point of attachment for a substituent. For example, —$CONH_2$ is attached through the carbon atom (C).

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as ($C_1$-$C_{22}$)alkyl, ($C_1$-$C_8$)alkyl, ($C_1$-$C_6$)alkyl, and ($C_1$-$C_4$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond (shown, for example, as "="), such as a straight or branched group of 2-22, 2-8, 2-6, or 2-4 carbon atoms, referred to herein as ($C_2$-$C_{22}$)alkenyl, ($C_2$-$C_8$)alkenyl, ($C_2$-$C_6$)alkenyl, and ($C_2$-$C_4$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond (shown, for example, as "≡"), such as a straight or branched group of 2-22, 2-8, 2-6, 2-4 carbon atoms, referred to herein as ($C_2$-$C_{22}$)alkynyl, ($C_2$-$C_8$)alkynyl, ($C_2$-$C_6$)alkynyl, and ($C_2$-$C_4$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "cycloalkyl" as used herein refers to a saturated or unsaturated monocyclic, bicyclic, other multicyclic, or bridged cyclic hydrocarbon group. A cyclocalkyl group can have 3-22, 3-12, or 3-8 ring carbons, referred to herein as ($C_3$-$C_{22}$)cycloalkyl, ($C_3$-$C_{12}$)cycloalkyl, or ($C_3$-$C_8$)cycloalkyl, respectively. A cycloalkyl group can also have one or more carbon-carbon double bond or carbon-carbon triple bond.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle[3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as $(C_6-C_{22})$aryl, $(C_6-C_{18})$aryl, $(C_6-C_{14})$aryl, or $(C_6-C_{10})$aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocylic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "$(C_6)$aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "$(C_6)$arylalkyl." The term "benzyl" as used herein refers to the group —$CH_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycyclic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1,9-diamine, or the like.

The term "heteroaromatic" or "heteroaryl" as used herein refers to a mono-, bi-, or multi-cyclic aromatic ring system containing one or more heteroatoms, for example 1-3 heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of N, O, and S. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "$(C_2-C_5)$heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl).

The term "bicyclic heteroaromatic" or "bicyclic heteroaryl" as used herein refers to a heteroaryl group fused to another aromatic or non-aromatic carbocyclic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl).

The term "tricyclic heteroaromatic" or "tricyclic heteroaryl" as used herein refers to a bicyclic heteroaryl group fused to another aromatic or non-aromatic carbocyclic or heterocyclic ring. The term "tricyclic heteroaromatic" or "tricyclic heteroaryl" also encompasses reduced or partly reduced forms of fused aromatic system wherein one or both rings contain ring heteroatoms. Each of the ring in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), pyrido[1,2-a]benzimidazole (pyrido[1,2-a]benzimidazolyl), and pyrido[1,2-b]indazole (pyrido[1,2-b]indazolyl).

The term "alkoxy" as used herein refers to an alkyl group attached to an oxygen (—O-alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as $(C_1-C_{22})$alkoxy, $(C_1-C_8)$alkoxy, or $(C_1-C_6)$alkoxy, respectively. Exemplary alkoxy groups include, but are not limited to, methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy." The term "arylalkoxy" as used herein refers to an arylalkyl group attached to an oxygen atom. An exemplary arylalkyl group is benzyloxy group.

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R_{b'}$ is not hydrogen. The amine or amino can be attached to the parent molecular group through the nitrogen. The amine or amino also may be cyclic, for example any two of $R_a$, $R_b$, and $R_{b'}$ may be joined together and/or with the N to form a 3- to 12-membered ring (e.g., morpholino or piperidinyl). The term amino also includes the corresponding quaternary ammonium salt of any amino group. Exemplary amines include alkylamine, wherein at least one of $R_a$ $R_b$, or $R_{b'}$ is an alkyl group, or cycloalkylamine, wherein at least one of $R_a$ $R_b$, or $R_{b'}$ is a cycloalkyl group.

The term "ammonia" as used herein refers to $NH_3$.

The term "aldehyde" or "formyl" as used herein refers to —CHO.

The term "acyl" term as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —$NR_cC(O)(R_d)$— or —$C(O)NR_cR_e$, wherein $R_c$, $R_d$, and $R_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, $R_c$, $R_d$, or $R_e$. The amide also may be cyclic, for example $R_c$ and $R_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to a sulfur atom. Exemplary arylthio groups include, but are not limited to, arylthios having a monocyclic aromatic ring system, wherein the ring comprises 6 carbon atoms, referred to herein as "$(C_6)$arylthio."

The term "arylsulfonyl" as used herein refers to an aryl group attached to a sulfonyl group, e.g., —$S(O)_2$-aryl-. Exemplary arylsulfonyl groups include, but are not limited to, arylsulfonyls having a monocyclic aromatic ring system, wherein the ring comprises 6 carbon atoms, referred to herein as "$(C_6)$arylsulfonyl."

The term "carbamate" as used herein refers to the form —$R_fOC(O)N(R_g)$—, —$R_fOC(O)N(R_g)R_h$—, or —$OC(O)NR_gR_h$, wherein $R_f$, $R_g$, and $R_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of $R_f$, $R_g$ and $R_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to $R_j$—COOH or its corresponding carboxylate salts (e.g., $R_j$—COONa), where $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein $R_j$ is alkyl, such as —O—C(O)-alkyl. Exemplary carboxy also include aryl or heteroaryl carboxy, e.g. wherein $R_j$ is an aryl, such as phenyl and tolyl, or heteroaryl group such as pyridine, pyridazine, pyrimidine and pyrazine. The term carboxy also includes "carboxycarbonyl," e.g. a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—$R_i$—, —$R_j$C(O)O—$R_i$—, or —$R_j$C(O)O—, where O is not bound to hydrogen, and $R_i$ and $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_i$ can be a hydrogen, but $R_j$ cannot be hydrogen. The ester may be cyclic, for example the carbon atom and $R_j$, the oxygen atom and $R_i$, or $R_i$ and $R_j$ may be joined to form a 3- to 12-membered ring. Exemplary esters include, but are not limited to, alkyl esters wherein at least one of $R_i$ or $R_j$ is alkyl, such as —O—C(O)-alkyl, —C(O)—O-alkyl-, and -alkyl-C(O)—O-alkyl-. Exemplary esters also include aryl or heteroaryl esters, e.g. wherein at least one of $R_i$ or $R_j$ is an aryl group, such as phenyl or tolyl, or a heteroaryl group, such as pyridine, pyridazine, pyrimidine or pyrazine, such as a nicotinate ester. Exemplary esters also include reverse esters having the structure —$R_j$C(O)O—, where the oxygen is bound to the parent molecule. Exemplary reverse esters include succinate, D-argininate, L-argininate, L-lysinate and D-lysinate. Esters also include carboxylic acid anhydrides and acid halides.

The term "ether" refers to the structure —$R_k$O—$R_l$—, where $R_k$ and $R_l$ can independently be alkyl, alkenyl, alkynyl, aryl, cycloalkyl, heterocyclyl, and ether. The ether can be attached to the parent molecular group through $R_k$ or $R_l$. Exemplary ethers include, but are not limited to, alkoxyalkyl and alkoxyaryl groups. Ethers also includes polyethers, e.g., where one or both of $R_k$ and $R_l$ are ethers.

The terms "halo" or "halogen" or "hal" or "halide" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_m$ (such as acetyl, —C(O)CH$_3$) or —$R_m$—C(O)—$R_n$—. The ketone can be attached to another group through $R_m$ or $R_n$. $R_m$ or $R_n$ can be alkyl, alkenyl, alkynyl, cycloalkyl, heterocyclyl or aryl, or $R_m$ or $R_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3^-$.

The term "perfluoroalkyl" as used herein refers to an alkyl group in which all of the hydrogen atoms have been replaced by fluorine atoms. Exemplary perfluoroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —$R_o$OP(O)O$_2^{2-}$, —OP(O)(OR$_q$)O$^-$, or —$R_o$OP(O)(OR$_p$)O$^-$, wherein $R_o$, $R_p$ and $R_q$ each independently can be alkyl, alkenyl, alkynyl, aryl, cycloalkyl, heterocyclyl, or hydrogen.

The term "sulfide" as used herein refers to the structure —$R_q$S—, where $R_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —$R_r$S(O)O—, —$R_r$S(O)OR$_s$—, or —S(O)OR$_s$—, wherein $R_r$ and $R_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_r$ or $R_s$ is alkyl, alkenyl, or alkynyl.

The term "sulfonamide" as used herein refers to the structure —($R_t$)—N—S(O)$_2$—$R_v$— or —$R_t$($R_u$)N—S(O)$_2$—$R_v$, where $R_t$, $R_u$, and $R_v$ can be, for example, hydrogen, alkyl, alkenyl, alkynyl, aryl, cycloalkyl, and heterocyclyl. Exemplary sulfonamides include alkylsulfonamides (e.g., where $R_v$ is alkyl), arylsulfonamides (e.g., where $R_v$ is aryl), cycloalkyl sulfonamides (e.g., where $R_v$ is cycloalkyl), and heterocyclyl sulfonamides (e.g., where $R_v$ is heterocyclyl).

The term "sulfonate" as used herein refers to a salt or ester of a sulfonic acid. The term "sulfonic acid" refers to $R_w$SO$_3$H, where $R_w$ is alkyl, alkenyl, alkynyl, aryl, cycloalkyl, or heterocyclyl (e.g., alkylsulfonyl). The term "sulfonyl" as used herein refers to the structure $R_x$SO$_2$—, where $R_x$ can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups.

The term "sulfonate" as used herein refers $R_w$SO$_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, CF$_3$SO$_3^-$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_aR_bR_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the invention or the intermediates useful for preparing them. Examples of suitable substituents include, but are not limited to: $(C_1-C_{22})$, $(C_1-C_8)$, $(C_1-C_6)$, or $(C_1-C_4)$ alkyl, alkenyl or alkynyl; $(C_6-C_{22})$, $(C_6-C_{18})$, $(C_6-C_{14})$, or $(C_6-C_{10})$ aryl; $(C_2-C_{21})$, $(C_2-C_{17})$, $(C_2-C_{13})$, or $(C_2-C_9)$ heteroaryl; $(C_3-C_{22})$, $(C_3-C_{12})$, or $(C_3-C_8)$ cycloalkyl; $(C_1-C_{22})$, $(C_1-C_8)$, $(C_1-C_6)$, or $(C_1-C_4)$ alkoxy; $(C_6-C_{22})$, $(C_6-C_{18})$, $(C_6-C_{14})$, or $(C_6-C_{10})$ aryloxy; —CN; —OH; oxo; halo; carboxy; amino, such as —NH($(C_1-C_{22})$, $(C_1-C_8)$, $(C_1-C_6)$, or $(C_1-C_4)$ alkyl), —N($(C_1-C_{22})$, $(C_1-C_8)$, $(C_1-C_6)$, or $(C_1-C_4)$ alkyl)$_2$, —NH($(C_6)$aryl), or —N($(C_6-C_{10})$ aryl)$_2$; formyl; ketones, such as —CO$_2$($(C_1-C_{22})$, $(C_1-C_8)$, $(C_1-C_6)$, or $(C_1-C_4)$ alkyl), —CO($(C_6-C_{10})$ aryl) esters, such as —CO$_2$($(C_1-C_{22})$, $(C_1-C_8)$, $(C_1-C_6)$, or $(C_1-C_4)$ alkyl) and —CO$_2$($(C_6-C_{10})$ aryl). One of skill in art can readily choose a suitable substituent based on the stability and pharmacological and synthetic activity of the compound of the invention.

The term "pharmaceutically acceptable counter ion" refers to a pharmaceutically acceptable anion or cation. In various embodiments, the pharmaceutically acceptable counter ion is a pharmaceutically acceptable ion. For example, the pharmaceutically acceptable counter ion is selected from citrate, malate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutically acceptable counter ion is selected from chloride, bromide, iodide, nitrate, sulfate, bisulfate, phosphate, acid phosphate, citrate, malate, acetate, oxalate, acetate, and lactate. In particular embodiments, the pharmaceutically acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present teachings. Compounds included in the present teachings that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, malate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitart rate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present teachings that include an amino moiety may form pharmaceutically acceptable salts with various amino acids, in addition to the acids mentioned above. Compounds included in the present teachings, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

Unless otherwise specified, the chemical groups include their corresponding monovalent, divalent, trivalent, and tetravalent groups. For example, methyl includes monovalent methyl (—CH$_3$), divalent methyl (—CH$_2$—, methylyl), trivalent methyl

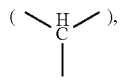

and tetravalent methyl

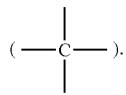

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques. For example, the term "about" can encompass variations of ±10%, ±5%, ±2%, ±1%, ±0.5%, or ±0.1% of the numerical value of the number which the term "about" modifies. In various embodiments, the term "about" encompasses variations of ±5%, ±2%, ±1%, or ±0.5% of the numerical value of the number. In some embodiments, the term "about" encompasses variations of ±5%, ±2%, or ±1% of the numerical value of the number. In certain embodiments, the term "about" encompasses variations of ±5% of the numerical value of the number. In certain embodiments, the term "about" encompasses variations of ±2% of the numerical value of the number. In certain embodiments, the term "about" encompasses variations of ±1% of the numerical value of the number.

All numerical ranges herein include all numerical values and ranges of all numerical values within the recited range of numerical values. As a non-limiting example, ($C_1$-$C_6$) alkyls also include any one of $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_2$-$C_3$), ($C_2$-$C_4$), ($C_2$-$C_5$), ($C_2$-$C_6$), ($C_3$-$C_4$), ($C_3$-$C_5$), ($C_3$-$C_6$), ($C_4$-$C_5$), ($C_4$-$C_6$), and ($C_5$-$C_6$) alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

The present teachings generally provide compounds, compositions, and methods of using the compounds or compositions.

Compounds

In various embodiments provided herein, a platinum (IV) compound includes a suitable reacting group for reacting with a functional group on a protein. The reacting group possesses protein-conjugating properties, i.e., it binds covalently to the protein. For example, the reacting group can be introduced by a ligand. In various embodiments, one of or both the axial ligands each comprises one or more reacting groups. In some embodiments, the protein is albumin. In some embodiments, the reacting group is a Michael acceptor. In some embodiments, a compound of the present teachings has Formula I:

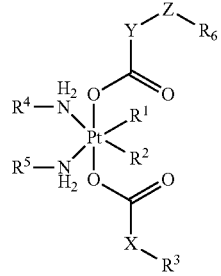

or a pharmaceutically acceptable salt thereof, wherein:

X and Y are independently selected from NH, alkyl and aryl;

$R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl;

$R^4$ and $R^5$ are each H or together constitute a cyclohexyl ring;

Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl; and $R^6$ is a suitable reacting group for reacting with a functional group on a protein such as but not limited to:

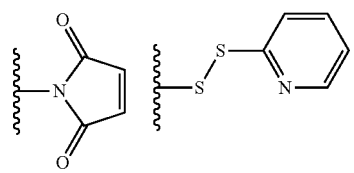

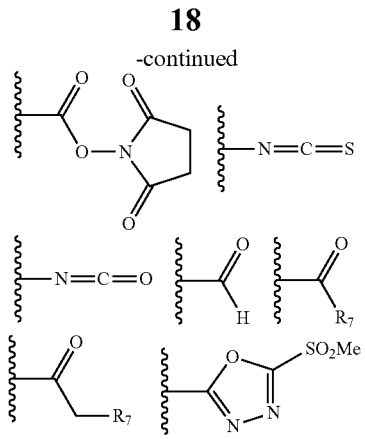

where $R^7$ is Cl, Br, F, mesylate, tosylate, O-(4-nitrophenyl), O-pentafluoropnenyl. Fhe reacting group can also be an activated disulfide group, a vinylcarbonyl group, a vinyl acetylene group, an epoxide, an aziridine group or an acetylene group. The groups may be substituted, where appropriate.

An embodiment of the invention is a compound or a pharmaceutically acceptable salt thereof wherein X together with $R^3$ is selected from the group consisting of:

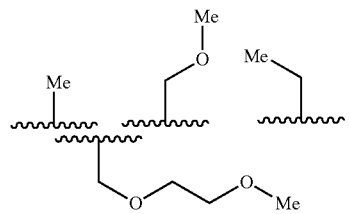

In some embodiments, the reacting group is a maleimide. Such compounds may be referred to herein as "monomaleimide compounds", i.e., Pt(IV)M monomaleimide compounds. As used herein, "monomaleimide compounds" are compounds with a single maleimide group. The monomaleimide compound has Formula II:

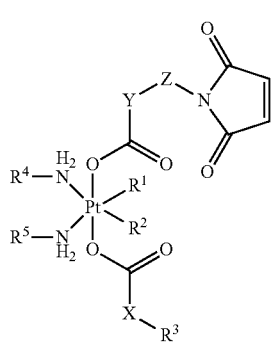

or a pharmaceutically acceptable salt thereof, wherein:

X and Y are independently selected from NH, alkyl and aryl;

$R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl;

$R^4$ and $R^5$ are each H or together constitute a cyclohexyl ring; and

Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

Not willing to be bound to any theory, the unsymmetrical nature of Pt(IV)M monomaleimide compounds allows for the modulation of platinum drug release.

Another embodiment of the invention is a maleimide compound or a pharmaceutically acceptable salt thereof wherein Y together with Z and the maleimide is selected from the group consisting of:

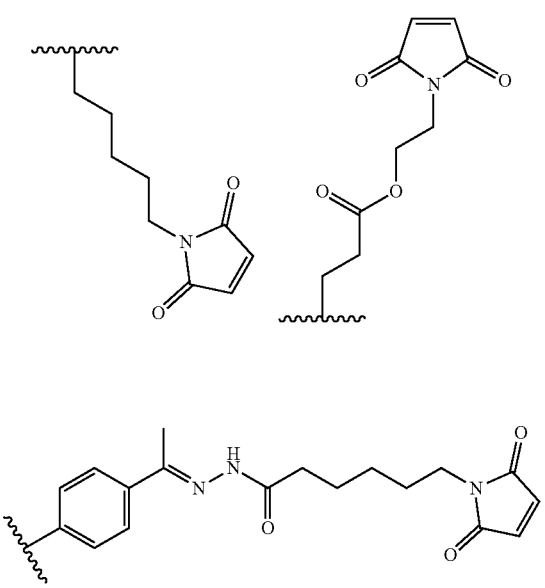

Another embodiment of the invention is a maleimide compound having Formula IIa:

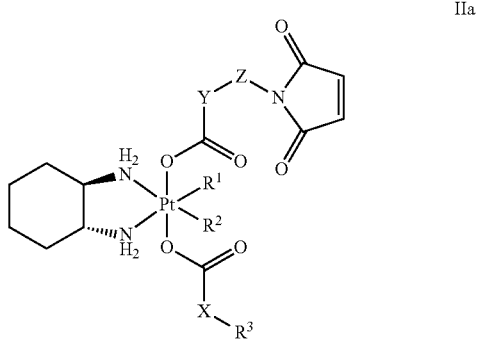

or a pharmaceutically acceptable salt thereof, wherein:

X and Y are independently selected from NH, alkyl and aryl;

$R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl; and Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

Another embodiment of the invention is a maleimide compounds having Formula IIb:

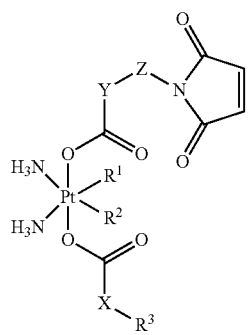

IIb or a pharmaceutically acceptable salt thereof, wherein:

X and Y are independently selected from NH, alkyl and aryl;

$R^1$ and $R^2$ each is Cl, or $R^1$ and $R^2$ are joined to form an oxalate;

$R^3$ is hydrogen, alkyl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, wherein each of the carboxyl, carbamoyl, ether, alkoxy, aryloxy, amino, amide, carbamate, alkyl, alkenyl, alkynyl, aryl, arylalkyl, cycloalkyl, heteroaryl, or heterocyclyl is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl; and Z is alternatively absent or alkyl, aryl, cycloalkyl, heterocyclyl, aryl, and heteroaryl, wherein each of the alkyl, alkenyl, cycloalkyl, heterocyclyl, aryl, and heteroaryl groups optionally is substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl, or alkylidene hydrazine wherein each of the carboxyl, carbamoyl, ether, alkoxy, aryloxy, amino, amide, carbamate, alkyl, alkenyl, alkynyl, aryl, arylalkyl, cycloalkyl, heteroaryl, heterocyclyl or alkylidene hydrazine is optionally substituted with one or more groups, each independently selected from halogen, cyano, nitro, hydroxyl, carboxyl, carbamoyl, ether, alkoxy, aryloxy, amino, amide, carbamate, alkyl, alkenyl, alkynyl, aryl, arylalkyl, cycloalkyl, heteroaryl, heterocyclyl.

A non-limiting example of a Pt(IV)M compound of the invention is a compound selected from the group consisting of the compounds listed:

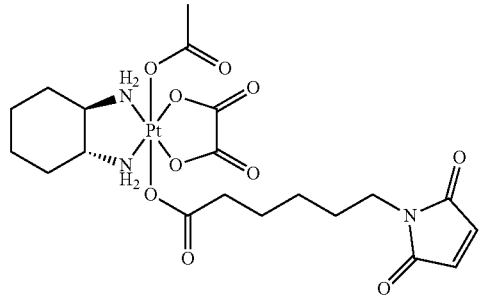

1

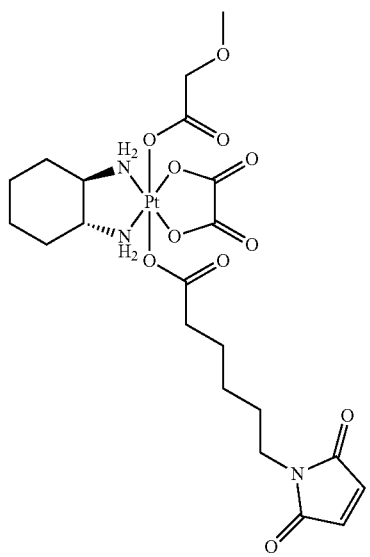

2

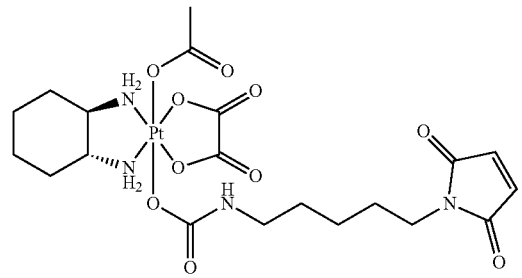

3

4
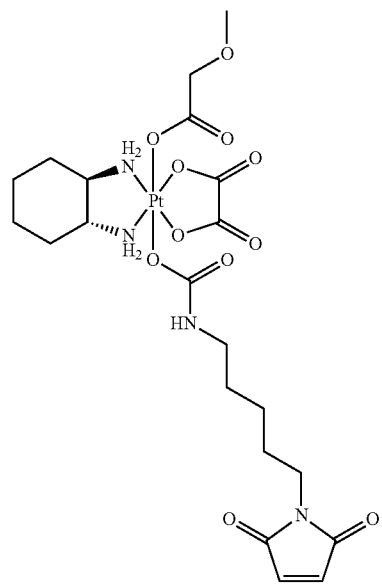
5
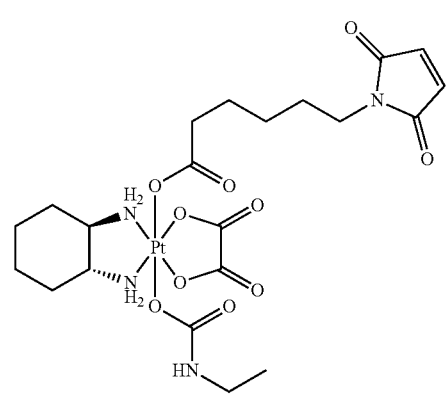
6
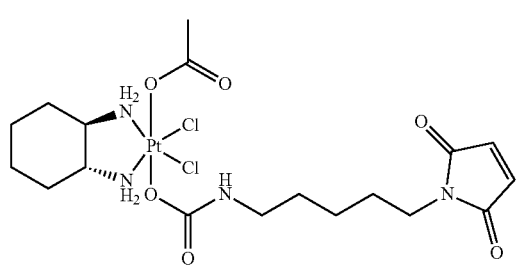
7
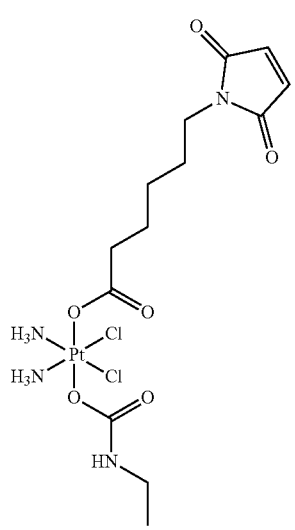
8
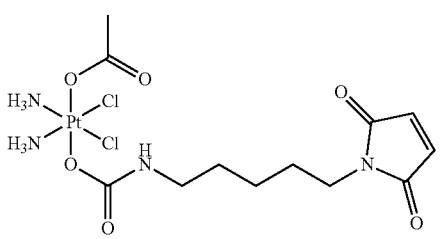
9
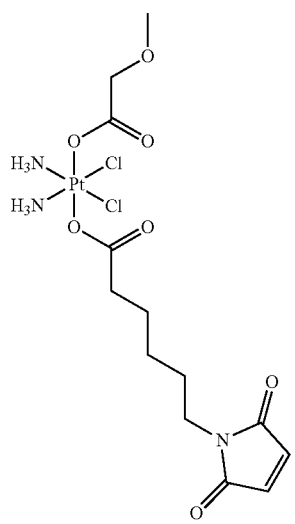

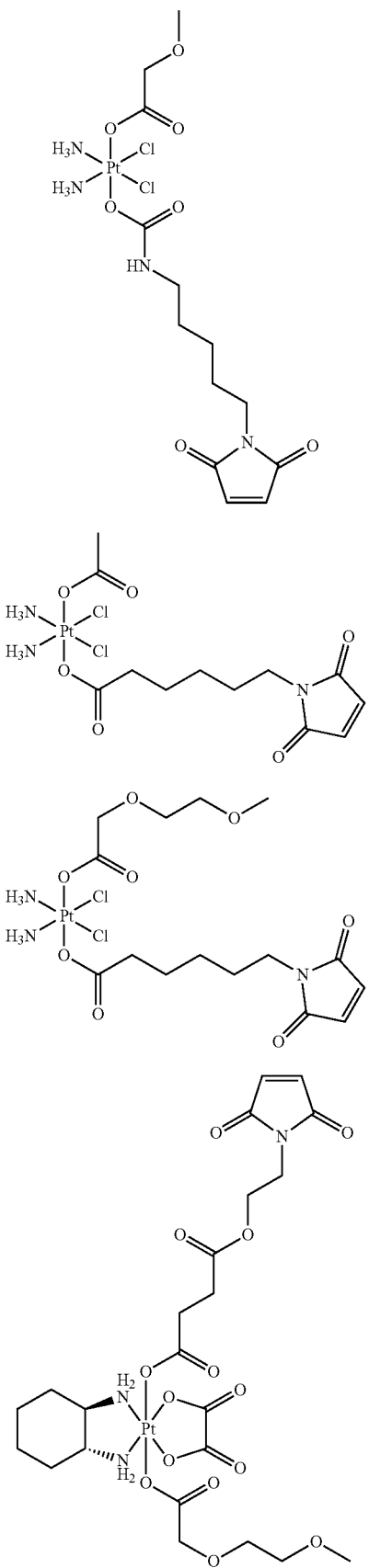
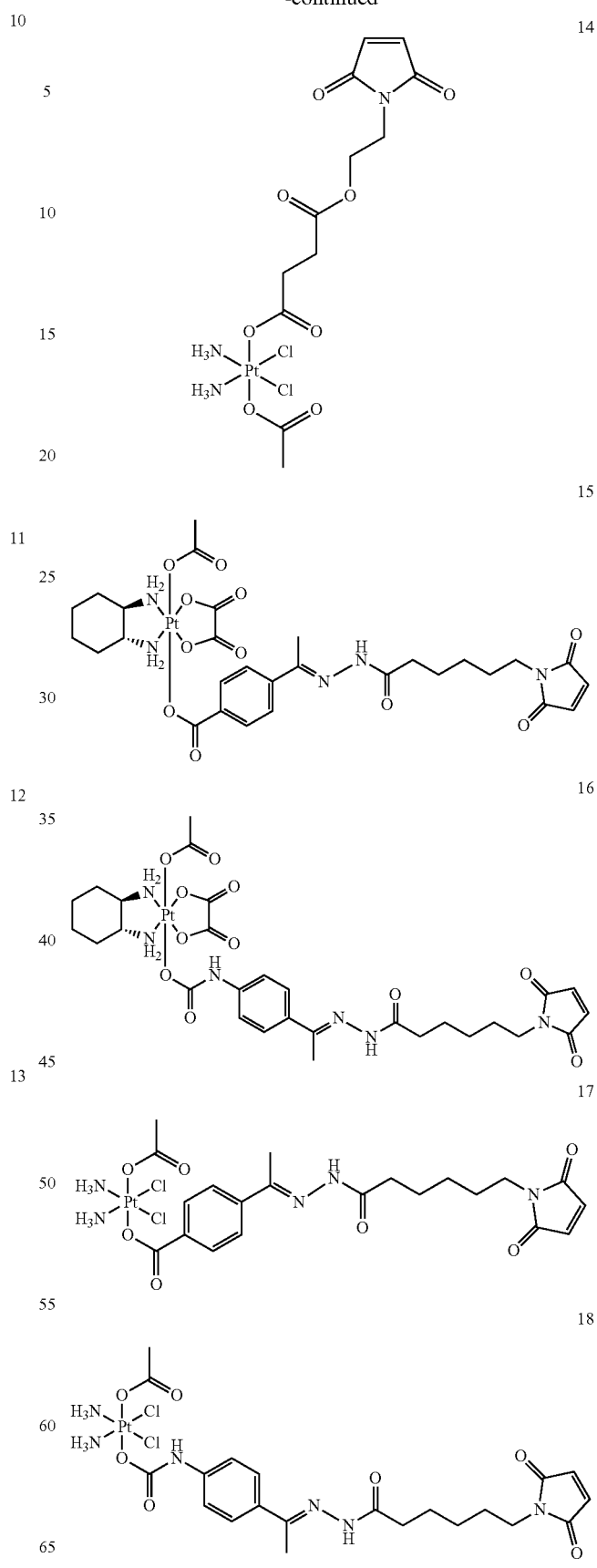

Another non-limiting example of a Pt(IV)M compound of the invention is a compound selected from the group consisting of the compounds listed:

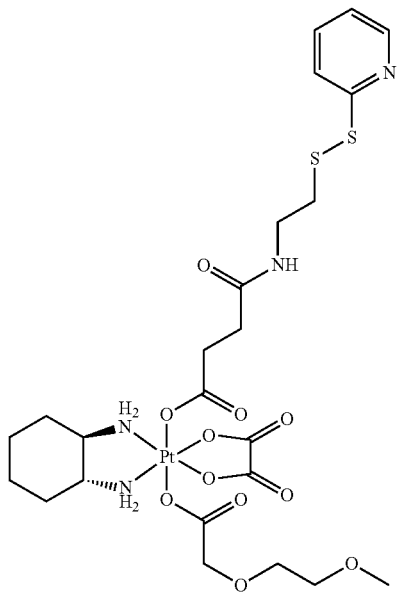

21

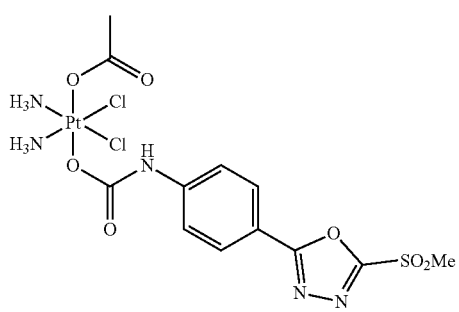

22

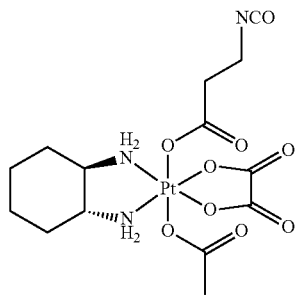

23

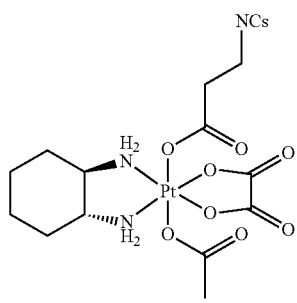

24

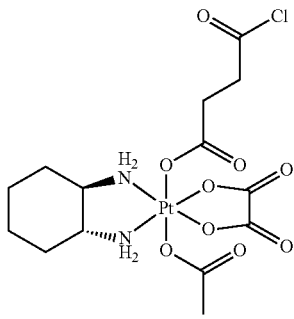

25

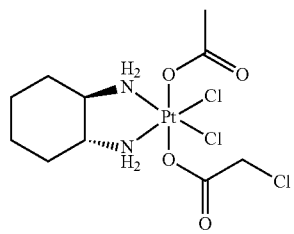

26

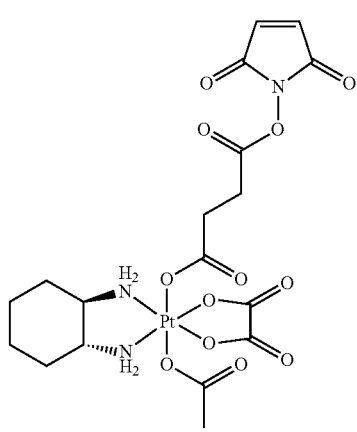

27

As described herein, some compounds of the present teachings may be provided as a salt comprising a charged platinum complex and a counter ion, including a pharmaceutically acceptable counter ion. The counter ion may be a weak or non-nucleophilic stabilizing ion, having a charge of (−1), (−2), (−3), (+1), (+2), (+3), etc. In some embodiments, the counter ion has a charge of (−1). In other embodiments, the counter ion has a charge of (−2). In some embodiments, the counter ion has a charge of (+1). In other embodiments, the counter ion has a charge of (+2).

The present teachings further comprise compositions (including pharmaceutical compositions) each comprising one or more of the compounds as described herein, and at least one pharmaceutically acceptable excipient.

Formulation, Delivery, Administration, and Dosing

In some embodiments, compositions are administered to humans, human patients or subjects. For the purposes of the present disclosure, the phrase "active ingredient" generally refers to the Pt(IV)M compounds to be delivered as described herein.

Although the descriptions of pharmaceutical compositions provided herein are principally directed to pharmaceutical compositions which are suitable for administration to humans, it will be understood by the skilled artisan that such compositions are generally suitable for administration to any other animal, e.g., to non-human animals, e.g. non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit. In some embodiments, the pharmaceutical composition described herein may be prepared, processed, packaged, or stored with a temperature of about 15-30° C. The temperature may be below 30° C. The temperature may be below 10° C. The temperature may be between about 0° C. to about 10° C., about 2° C. to about 8° C. The pharmaceutical composition may be stored at a temperature of below 0° C., below about −10° C., or below about −20° C.

In some embodiments, the pharmaceutical composition described herein may be protected from light. The pharmaceutical composition described herein may be packaged or stored in any opaque or light-filtering vial such as an amber vial to minimize exposure to light.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

The Pt(IV)M compounds of the present invention can be formulated using one or more excipients to: (1) increase stability; (2) permit the sustained or delayed release (e.g., from a depot formulation of the Pt(IV)M compounds); (3) alter the biodistribution (e.g., target the Pt(IV)M compounds to specific tissues or cell types); (4) alter the release profile of the Pt(IV)M compounds in vivo. Non-limiting examples of the excipients include any and all solvents, dispersion media, diluents, or other liquid vehicles, dispersion or suspension aids, surface active agents, isotonic agents, thickening or emulsifying agents, and preservatives. Excipients of the present invention may also include, without limitation, lipidoids, liposomes, lipid nanoparticles, polymers, micelles, dendrimers, exosomes, cyclodextrins, lipoplexes, core-shell nanoparticles, peptides, proteins, enzymes including hyaluronidase, nanoparticle mimics and combinations thereof. Accordingly, the formulations of the invention may include one or more excipients, each in an amount that together increases the stability of the Pt(IV)M compounds.

In some embodiments, the pH value of the pharmaceutical composition is between about 3 to about 7, between 3 and 6, between 3 and 5, about 3, about 4, about 5, about 6 or about 7.

Excipients

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants, bulking agents, and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference in its entirety) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical compositions.

Exemplary diluents include, but are not limited to, dextrose, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM®), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and VEEGUM® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [TWEEN® 20], polyoxyethylene sorbitan [TWEEN® 60], polyoxyethylene sorbitan monooleate [TWEEN® 80], sorbitan monopalmitate [SPAN® 40], sorbitan monostearate [SPAN® 60], sorbitan tristearate [SPAN® 65], glyceryl monooleate, sorbitan monooleate [SPAN® 80]), polyoxyethylene esters (e.g. polyoxyethylene monostearate [MYRJ® 45], polyoxyethylene hydrogenated castor oil, polyethoxylated castor oil, polyoxymethylene stearate, and SOLUTOL®), sucrose fatty acid esters, polyethylene glycol fatty acid esters (e.g. CREMOPHOR®), polyoxyethylene ethers, (e.g. polyoxyethylene lauryl ether [BRIJ® 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Poloxamer® 188 (Pluronic® F-68), Poloxamer® 407 (Pluronic® F-127), cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT PLUS®, PHENONIP®, methylparaben, GERMALL® 115, GERMABEN® II, NEOLONE™, KATHON™, and/or EUXYL®.

Exemplary buffering agents include, but are not limited to, succinate, tartrate, and lactate buffers, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Excipients such as cocoa butter and suppository waxes, coloring agents, coating agents, sweetening, flavoring, and/or perfuming agents can be present in the composition, according to the judgment of the formulator.

In some embodiments, the excipients have a weight percent of between about 0.5% (w/w) to about 50% (w/w), between about 1% (w/w) to about 50% (w/w), between about 0.5% (w/w) to about 20% (w/w), between about 1% (w/w) to about 20% (w/w), between about 1% (w/w) to about 10% (w/w), or between about 1% (w/w) to about 5% (w/w).

In some embodiments, the excipients comprise mannitol, sucrose, lactose, trehalose, and/or inulin. In one embodiment, the excipients comprise mannitol having a weight percent of between about 1% (w/w) and about 10% (w/w). The concentration of mannitol may be about 1% (w/w), 2% (w/w), 3% (w/w), or 4% (w/w).

In some embodiments, the excipients comprise a buffer having a pH of between about 2 to about 6, or about 4 to about 5. The concentration of the buffer may be between about 0.5 mM to about 100 mM, about 1 mM to about 50 mM, about 1 mM to about 20 mM, between about 1 mM to about 10 mM, or between about 1 mM to about 5 mM.

In some embodiments, the excipients may comprise citrate, acetate, lactate, succinate and/or tartrate buffers. The concentration of the buffers may be between about about 0.5 mM to about 100 mM, about 1 mM to about 10 mM.

In one embodiment, the excipients comprise a citrate buffer comprising sodium citrate and citric acid, or citric acid and sodium hydroxide. The concentration of the citrate buffer may be at least about 5 mM.

Administration

The Pt(IV)M compounds of the present invention may be administered by any route which results in a therapeutically effective outcome. These include, but are not limited to enteral, gastroenteral, epidural, oral, transdermal, epidural (peridural), intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection, (into the base of the penis), intravaginal administration, intrauterine, extra-amniotic administration, transdermal (diffusion through the intact skin for systemic distribution), transmucosal (diffusion through a mucous membrane), insufflation (snorting), sublingual, sublabial, enema, eye drops (onto the conjunctiva), or in ear drops. In specific embodiments, compositions may be administered in a way which allows them cross the blood-brain barrier, vascular barrier, or other epithelial barrier.

Dosing

The present invention provides methods comprising administering Pt(IV)M compounds to a subject in need thereof. Pt(IV)M compounds as described herein may be administered to a subject using any amount and any route of administration effective for preventing or treating or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like.

Compositions in accordance with the invention are typically formulated in dosage unit form for ease of administration and uniformity of dosage. It will be understood, however, that the total daily usage of the compositions of the present invention may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, compositions in accordance with the present invention may be administered at dosage levels sufficient to deliver from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

In some embodiments, compositions in accordance with the present invention may be administered at dosage levels from about 10 mg/m$^2$ to about 500 mg/m$^2$, from about 20 mg/m$^2$ to about 400 mg/m$^2$, from about 50 mg/m$^2$ to about 400 mg/m$^2$, from about 20 mg/m$^2$ to about 200 mg/m$^2$, from about 20 mg/m$^2$ to about 100 mg/m$^2$, of subject body surface area per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In some embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used.

As used herein, a "split dose" is the division of single unit dose or total daily dose into two or more doses, e.g, two or more administrations of the single unit dose. As used herein, a "single unit dose" is a dose of any therapeutic administered in one dose/at one time/single route/single point of contact, i.e., single administration event. As used herein, a "total daily dose" is an amount given or prescribed in 24 hr period.

It may be administered as a single unit dose. In one embodiment, the Pt(IV)M compounds of the present invention are administered to a subject in split doses. The Pt(IV)M compounds may be formulated in buffer only or in a formulation described herein.

Dosage Forms

A pharmaceutical composition described herein can be formulated into a dosage form described herein, such as an oral, topical, intranasal, intratracheal, or injectable (e.g., intravenous, intraocular, intravitreal, intramuscular, intracardiac, intraperitoneal, subcutaneous).

Liquid Dosage Forms

Liquid dosage forms for parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art including, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. In certain embodiments for parenteral administration, compositions may be mixed with solubilizing agents such as CREMOPHOR®, alcohols, oils, modified oils, glycols, polysorbates, cyclodextrins, polymers, and/or combinations thereof.

Injectable

Injectable preparations, for example, sterile injectable aqueous or oleaginous suspensions may be formulated according to the known art and may include suitable dispersing agents, wetting agents, and/or suspending agents. Sterile injectable preparations may be sterile injectable solutions, suspensions, and/or emulsions in nontoxic parenterally acceptable diluents and/or solvents, for example, a solution in 1,3-butanediol. Among the acceptable vehicles and solvents that may be employed include, but are not limited to, water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by exposure to dry heat, moist heat, or irradiation, or by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it may be desirable to slow the absorption of the active ingredient from subcutaneous or intramuscular injection. This may be accomplished by the use of a liquid suspension of crystalline or amorphous material with poor water solubility. The rate of absorption of the Pt(IV)M compounds then depends upon its rate of dissolution which, in turn, may depend upon crystal size and crystalline form. Alternatively, delayed absorption of a parenterally administered Pt(IV)M compound may be accomplished by dissolving or suspending the monomalimide in an oil vehicle. Injectable depot forms are made by forming microencapsule matrices of the Pt(IV)M compounds in biodegradable polymers such as polylactide-polyglycolide. Depending upon the ratio of Pt(IV)M compounds to polymer and the nature of the particular polymer employed, the rate of Pt(IV)M compound release can be controlled. Examples of other biodegradable polymers include, but are not limited to, polylactides, polylactones, poly(orthoesters) and poly(anhydrides). Depot injectable formulations may be prepared by entrapping the Pt(IV)M compounds in liposomes or microemulsions which are compatible with body tissues.

Pulmonary

Formulations described herein as being useful for pulmonary delivery may also be used for intranasal delivery of a pharmaceutical composition. Another formulation suitable for intranasal administration may be a coarse powder comprising the active ingredient and having an average particle from about 0.2 μm to 500 μm. Such a formulation may be administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, contain about 0.1% to 20% (w/w) active ingredient, where the balance may comprise an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

General considerations in the formulation and/or manufacture of pharmaceutical agents may be found, for example, in Remington: The Science and Practice of Pharmacy 21st ed., Lippincott Williams & Wilkins, 2005 (incorporated herein by reference in its entirety).

Coatings or Shells

Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Pharmaceutical Compositions and Methods of Use

Embodiments of the present teachings also relate to treating a hyperproliferative disorder, cancer and/or a tumor according to any of the techniques and compositions and combinations of compositions described herein.

In various embodiments, methods for treating a subject having a cancer are provided, wherein the method comprises administering a therapeutically-effective amount of a compound, as described herein, to a subject having a cancer, suspected of having cancer, or having a predisposition to a cancer. According to the present invention, cancer embraces any disease or malady characterized by uncontrolled cell proliferation, e.g., hyperproliferation. Cancers may be characterized by tumors, e.g., solid tumors or any neoplasm.

In some embodiments, the subject may be otherwise free of indications for treatment with the compound. In some embodiments, methods include use of cancer cells, including but not limited to mammalian cancer cells. In some instances, the mammalian cancer cells are human cancer cells.

In some embodiments, the compounds of the present teachings have been found to inhibit cancer and/or tumor growth. They may also reduce cell proliferation, invasiveness, and/or metastasis, thereby rendering them useful for the treatment of a cancer.

In some embodiments, the compounds of the present teachings may be used to prevent the growth of a tumor or cancer, and/or to prevent the metastasis of a tumor or cancer. In some embodiments, compositions of the present teachings may be used to shrink or destroy a cancer.

In some embodiments, a compound provided herein is useful for inhibiting proliferation of a cancer cell. In some embodiments a compound provided herein is useful for inhibiting cellular proliferation, e.g., inhibiting the rate of cellular proliferation, preventing cellular proliferation, and/or inducing cell death. In general, a compound as described herein can inhibit cellular proliferation of a cancer cell or both inhibiting proliferation and/or inducing cell death of a cancer cell.

The cancers treatable by methods of the present teachings generally occur in mammals. Mammals include, for example, humans, non-human primates, dogs, cats, rats, mice, rabbits, ferrets, guinea pigs horses, pigs, sheep, goats, and cattle. In various embodiments, the cancer is lung cancer, e.g., small cell lung cancer, non-small cell lung cancer, squamous cell lung cancer, breast cancer, e.g., mutant BRCA1 and/or mutant BRCA2 breast cancer, non-BRCA-associated breast cancer, colorectal cancer, colon cancer, ovarian cancer, pancreatic cancer, bladder cancer, prostate cancer, cervical cancer, renal cancer, leukemia, central nervous system cancers, myeloma, melanoma, mesothelioma, stomach cancer, rectal cancer, cancer of the large intestine, cancer of the small intestine, esophageal cancer, uterine cancer, head and neck cancer, endometrial cancer, eye cancer, thyroid cancer, testicular cancer, bile duct cancer, liver cancer, kidney cancer, pituitary cancer, lymphoma, brain cancer, glioma, glioblastoma multiforme, meningioma, medulloblastoma, astrocytoma, neuroblastoma, basal cell carcinoma of the skin, sarcoma, synovial sarcoma, rhabdomyosarcoma, leiomyosarcoma, chondrosarcoma, and fibrosarcoma. In some embodiments, the cancer is lung cancer. In certain embodiments, the cancer is human lung carcinoma, ovarian cancer, pancreatic cancer or colorectal cancer.

In some embodiments, the compounds of the present teachings may be administered to the cancer cells having BRCA1 mutations, BRCA2 mutations, ERCC1 or ERCC2 mutations, mutations in the fanconi anemia genes, MLH1, MSH2, PTEN, Mutations in genes that code for proteins involved in DNA repair, mutations in genes that code for proteins involved in non-homologous DNA repair, mutations in genes that code for proteins involved in nucleotide excision repair, mutations in genes that code for proteins involved in DNA mismatch repair, genetic tests that identify tumors that have a defect in DNA repair, changes in the expression of genes involved in DNA repair such as ERCC1 or ERCC2, and so on. The mutations may be germline or somatic.

In another aspect, the compounds of the present teachings may be administered to cells with increased albumin uptake, for example, but not limited to, cells with mutations that increase micropinocytosis, cells with mitogen activated kinase pathway mutations, cells with KRAS mutations, cells with BRAF mutations, cells with RAC mutations, cells with RAS overexpression, cells with RAC1 activation, or cells with CDC42 activation.

In some embodiments, cells with increased albumin update may be identified with imaging techniques. For example, a contrast agent is administered to a patient and the level of accumulation of the contrast agent at a tumor site is measured with an imaging technique. The imaging technique may be ultrasound, X-ray, single-photon emission tomography/computed tomography (SPECT/CT), positron emission tomography/computed tomography (PET/CT), magnetic resonance imaging (MRI), computed tomography (CT), single-photon emission tomography (SPECT), fluorescence tomography, and fluorescence spectroscopy.

In yet another aspect, the compounds of the present teachings may be administered to tumors with a high level of enhanced permeability and retention (EPR) effect. In some embodiments, tumors with a high level of enhanced permeability and retention effect may be identified with imaging techniques. As a non-limited example, iron oxide nanoparticle magnetic resonance imaging may be administered to a patient and EPR effects are measured.

In some embodiments, the compounds of the present teachings may be administered to a subject selected with the method disclosed in WO2015017506, the contents of which are incorporated herein by reference in their entirety, the method comprising:

(a) administering a contrast agent to the subject;
(b) measuring the level of accumulation of the contrast agent at at least one intended site of treatment; and
(c) selecting the subject based on the level of the accumulation of the contrast agent; wherein the intended site of treatment is a tumor.

Kits and Devices

The invention provides a variety of kits and devices for conveniently and/or effectively carrying out methods of the present invention. Typically kits will comprise sufficient amounts and/or numbers of components to allow a user to perform multiple treatments of a subject(s) and/or to perform multiple experiments.

In one embodiment, the present invention provides kits for inhibiting tumor cell growth in vitro or in vivo, comprising a Pt(IV)M compound of the present invention or a combination of Pt(IV)M compounds of the present invention, optionally in combination with any other active agents.

The kit may further comprise packaging and instructions and/or a delivery agent to form a formulation composition. The delivery agent may comprise a saline, a buffered solution, or any delivery agent disclosed herein. The amount of each component may be varied to enable consistent, reproducible higher concentration saline or simple buffer formulations. The components may also be varied in order to increase the stability of Pt(IV)M compounds in the buffer solution over a period of time and/or under a variety of conditions.

The present invention provides for devices which may incorporate Pt(IV)M compounds of the present invention. These devices contain in a stable formulation available to be immediately delivered to a subject in need thereof, such as a human patient. In some embodiments, the subject has cancer.

Non-limiting examples of the devices include a pump, a catheter, a needle, a transdermal patch, a pressurized olfactory delivery device, iontophoresis devices, multi-layered microfluidic devices. The devices may be employed to deliver Pt(IV)M compounds of the present invention according to single, multi- or split-dosing regiments. The devices may be employed to deliver Pt(IV)M compounds of the present invention across biological tissue, intradermal, subcutaneously, or intramuscularly. More examples of devices suitable for delivering Pt(IV)M compounds include but not limited to a medical device for intravesical drug delivery disclosed in International Publication WO 2014036555, a glass bottle made of type I glass disclosed in US Publication No. 20080108697, a drug-eluting device comprising a film made of a degradable polymer and an active agent as disclosed in US Publication No. 20140308336, an infusion device having an injection micropump, or a container containing a pharmaceutically stable preparation of an active agent as disclosed in U.S. Pat. No. 5,716,988, an implantable device comprising a reservoir and a channeled member in fluid communication with the reservoir the as disclosed in International Publication WO 2015023557, a hollow-fibre-based biocompatible drug delivery device with one or more layers as disclosed in US Publication No. 20090220612, an implantable device for drug delivery including an elongated, flexible device having a housing defining a reservoir that contains a drug in solid or semi-solid form as disclosed in International Publication WO 2013170069, a bioresorbable implant device disclosed in U.S. Pat. No. 7,326,421, contents of each of which are incorporated herein by reference in their entirety. It will be appreciated that the following examples are intended to illustrate but not to limit the present invention. Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated by reference in their entirety.

EXAMPLES

Example 1

Preparing Pt(IV)M Compounds

Synthesis of the Pt(IV)M compounds and HPLC analytical methods have been described in Examples 1-19 of PCT application No. PCT/US2015/037071, the contents of which are incorporated herein by reference in their entirety.

Example 2

Composition of Compound 8 Powder for Injection

In order to determine a stable formulation for Compound 8, several experiments were conducted to assess the stability of Compound 8 under different conditions including pH, buffer molarity, exposure to light, and temperature. It was determined that two major impurities develop during the formulation procedure (shown below). The first impurity, Impurity-1, is a free amine without a platinum group that can develop when the formulation is exposed to light. The second impurity, Impurity-2, is a ring-opening product of the maleimide group which forms at pH values above 5. After extensive evaluation, the final formulation was determined to be a solution of 3-5 mg/ml of Compound 8 in 5 mM citrate buffer at pH about 4 with 5% mannitol in water for injection. After the identification of the vehicle, the saturated solubility of several drug substance lots was determined in the vehicle of choice. It was also determined that during and after formulation, the compositions must be protected from light and maintained at 2 to 8° C. during formulation and refrigerated upon storage to minimize the formation of both impurities.

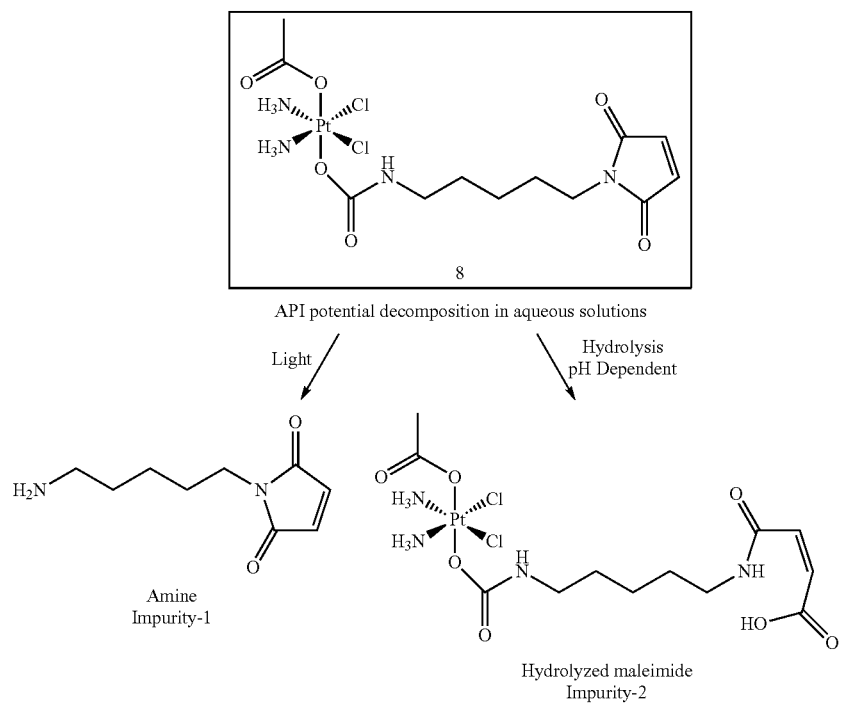

Results pH Stability: pH Range Screen with 120 mM Britton Robinson Universal Buffer It has been well established in the literature that the maleimide group is susceptible to a ring-opening product at physiological pH values. In order to determine the stability of Compound 8 at a range of pH values, a stock solution of 10 mg/ml Compound 8 in N,N-dimethylformamide (DMF) was spiked into a series of Britton Robinson buffers with pH set at values of 2, 4, 5, 6, 7.3, and 8 to make a final concentration of 0.1 mg/ml Compound 8. The amount of Impurity 2 (maleimide ring opening impurity) that was produced over the course of 24 hr at room temperature is shown in FIG. 1.

From this preliminary experiment, it was determined that Impurity 2 is not produced at pH values below 4 for up to 24 hr. At shorter time periods, Compound 8 is stable at higher pH values. For example, Impurity 2 is not detected at 4 hr at pH 5 and even at pH 6 Impurity 2 is not detected within 1 hr. However, for longer storage conditions or for in-use stability time, the lower pH is preferred in order to minimize the contribution of Impurity to the total impurity profile.

pH Stability: Evaluation of Acidifying Formulations

Figure 2:
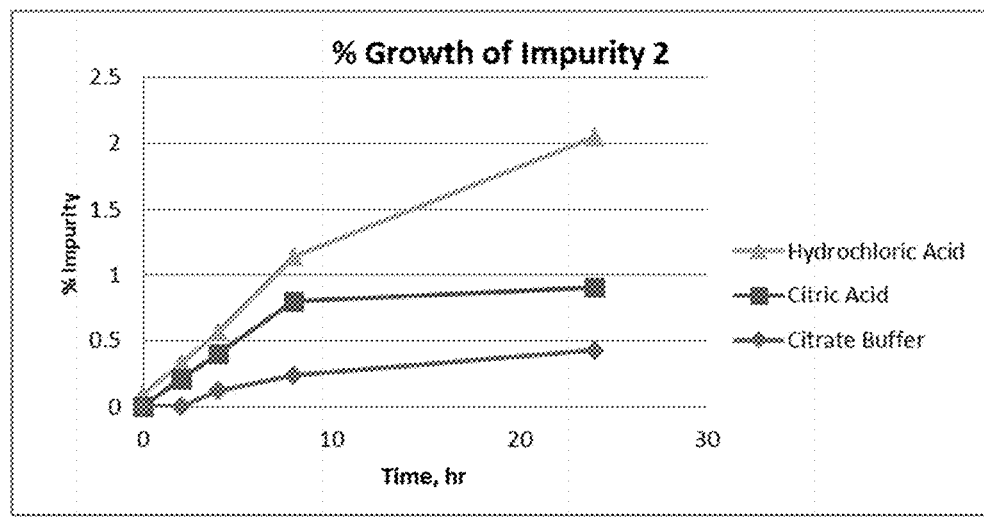
FIG. 2 shows formation of Impurity 2 in acidic vehicle formulations.

In order to determine whether a buffer would be required to maintain stability, two acidifying agents, hydrochloric acid and citric acid, were evaluated with respect to a control formulation in 5 mM citrate buffered saline. All vehicles were brought to a pH of 4 in saline and each formulation was made at 1 mg/ml concentration in each vehicle. The relative amount of Impurity 2 produced over 24 hr stored at room temperature is shown in FIG. 2.

The citrate buffered formulation inhibits the formation of Impurity 2 likely due to its ability to buffer the formulation. In contrast, both of the formulations made with the acidifying agents show higher Impurity 2 formation, with hydrochloric acid forming over 2% by area after 24 hrs. Therefore, based on these data a buffered formulation is preferred.

pH Stability: Buffering Capacity

Based on the data generated by the acidic vehicle study, it was identified that a buffered formulation would be preferred. For clinical dosing, it is optimal to decrease the amount of buffer that will be dosed so that upon injection the buffering capacity of the formulation will be overridden by the buffering capacity of the blood. This shift in pH to physiological values is ideal for the binding of albumin to the maleimide group on the drug. Additionally, it has been suggested by the literature to limit the amount of buffer dosed in non-clinical studies to less than 10 mM.

In order to assess the effect of the buffering capacity, formulations were made with 5 mM and 100 mM citrate saline pH about 4. Two formulations were made in 100 mM citrate, one at 0.1 mg/ml and the other at 1 mg/ml. A third formulation of 5 mM citrate at 1 mg/ml was made for comparison to determine whether increasing the buffering capacity improved the stability of the formulation.

Figure 3:
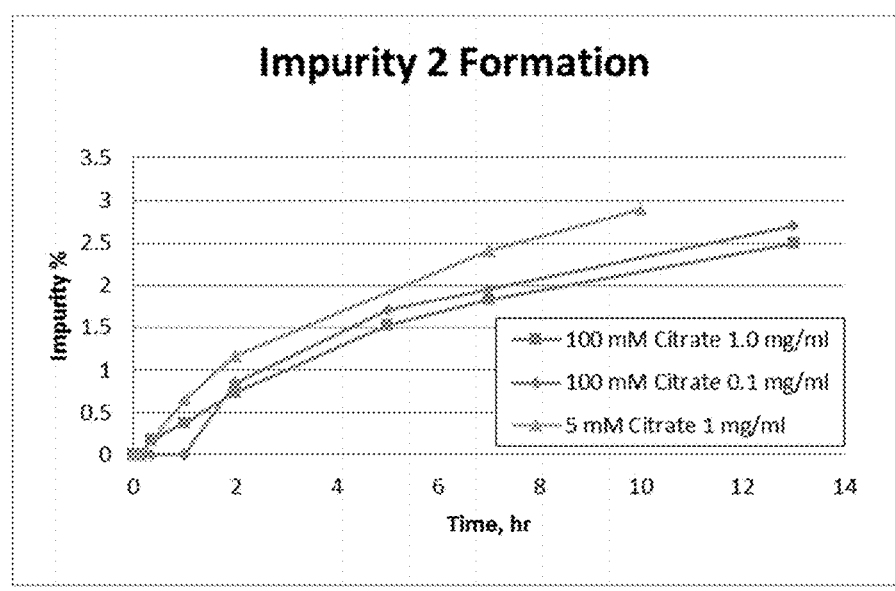
FIG. 3 shows formation of Impurity 2 as a function of buffer molarity.

The buffering capacity appeared to have little effect on the stability of Compound 8, as seen in FIG. 3. The impurity profile over 10 hr was similar for 5 mM versus 100 mM. Therefore, a lower molarity buffer was chosen in order to mitigate the risks of using a higher amount of buffer.

pH Stability: Final Determination of pH

After a thorough analysis of the contributions of pH to the stability of the drug product, the final two vehicles considered consisted of 5 mM citrate saline pH adjusted to either 4 or 5. Both prototypes were evaluated in mock manufacturing processes and mock clinical dilution studies.

Vial Selection: Clear Versus Amber

Compound 8 product has 2 major degradation pathways in aqueous solutions, namely Impurity 1 and Impurity 2. Impurity 1 is rapidly formed when exposed light whereas Impurity 2 is pH-dependent. The growth of both impurities appears to be independent; however, if the amine product (Impurity 1) is formed in high concentrations it increases the pH of the formulation which in turn catalyzes the production of Impurity 2. In order to minimize the formation of these impurities, it is recommended to store the drug product in an amber vial. The following experiments monitor the formulations when stored in clear versus amber vials.

Figure 4:
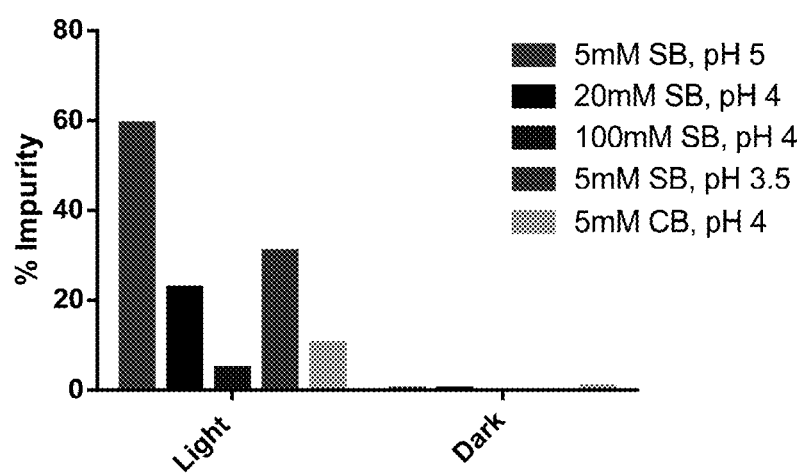
FIG. 4 shows Impurity 1 formation in light versus dark conditions (lower figure represents the magnified version of the dark formulations).
Figure 4:
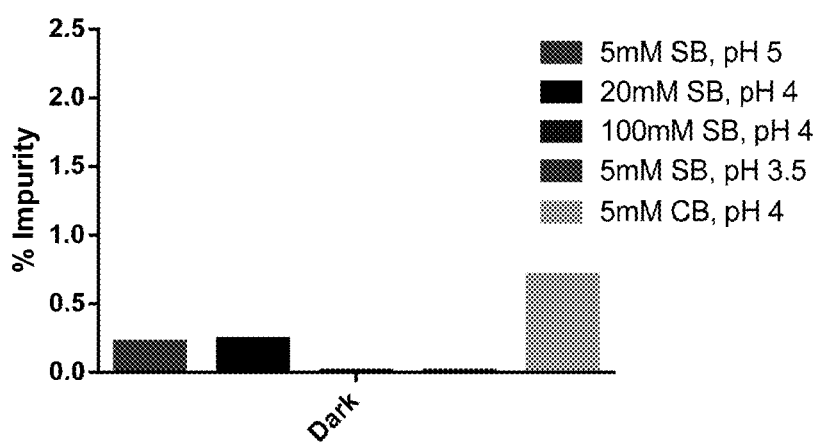
Figure 5:
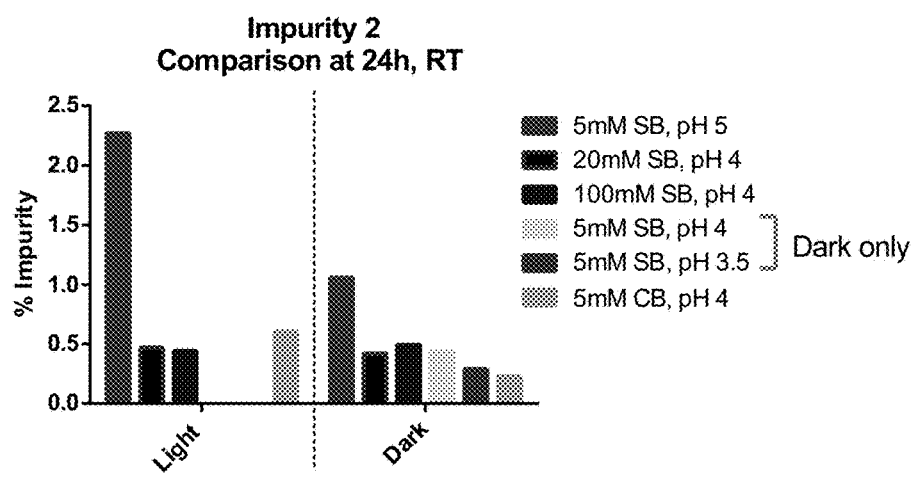
FIG. 5 shows Impurity 2 formation in light versus dark conditions.

To compare light versus dark conditions, Compound 8 was formulated in 5 mM citrate buffer saline at pH about 4 and placed into two separate vials (one clear and the other amber). The formulations were stored at room temperature for 24 hours and the amount of Impurity 1 and Impurity 2 was observed. From the FIGS. 4 and 5, it can be seen that exposing the Compound 8 solution to light in a clear vial caused an increase in the amount of Impurity 1 in comparison to the solution contained in an amber vial (~10% Impurity 1 compared to ~0.75% Impurity 1). Similarly the amount of Impurity 2 also decreased from 0.5% (clear vial) to ~0.25% (amber vial) when stored in dark conditions. Also, from these experiments it was concluded that the formation of Impurity 2 is not photosensitive but dependent upon the pH of the formulation.

Temperature Effects

In order to determine the effect of both temperature and light on the formation of the two main degradation products, mock manufacturing processes and mock clinical dilution studies were conducted. The mock process was simulated by formulating and holding the Compound 8 drug product at room temperature or under cold conditions (e.g. ice bath) for discreet amounts of time that would simulate the large scale manufacturing process. Once the samples went through the mock manufacturing process, they were stored at −20° C., as a frozen solution, and then thawed as they would be in the clinic prior to administration. For the mock clinical dilution study, each solution was diluted in saline, at the lowest dilution factor expected in the clinic. Then the diluted formulations were stored in syringes at room temperature and then assayed for potency and total impurities (from both procedures) at the end of the day.

Figure 6:
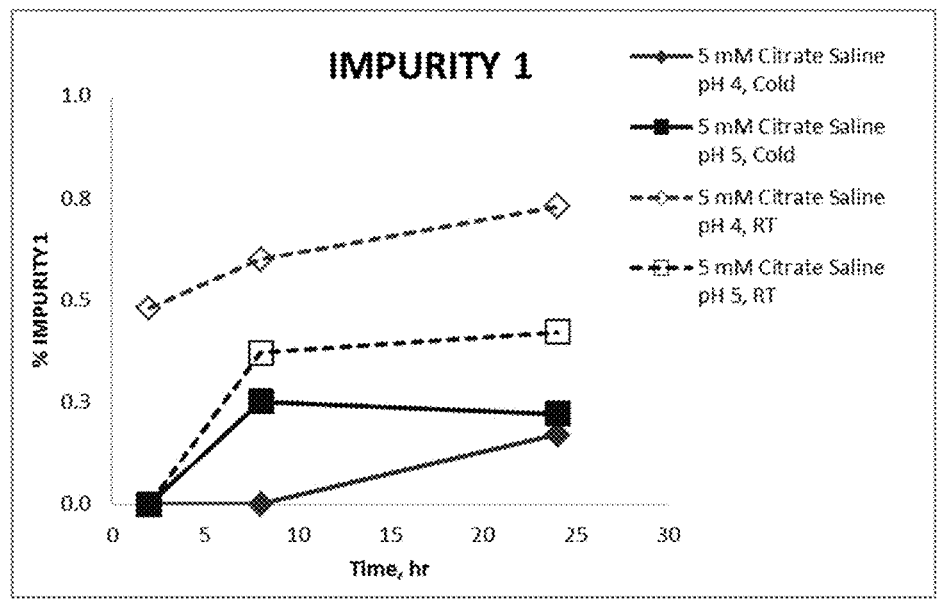
FIG. 6 shows formation of Impurity 1 a mock scale-up process at room temperature versus cold temperatures.
Figure 7:
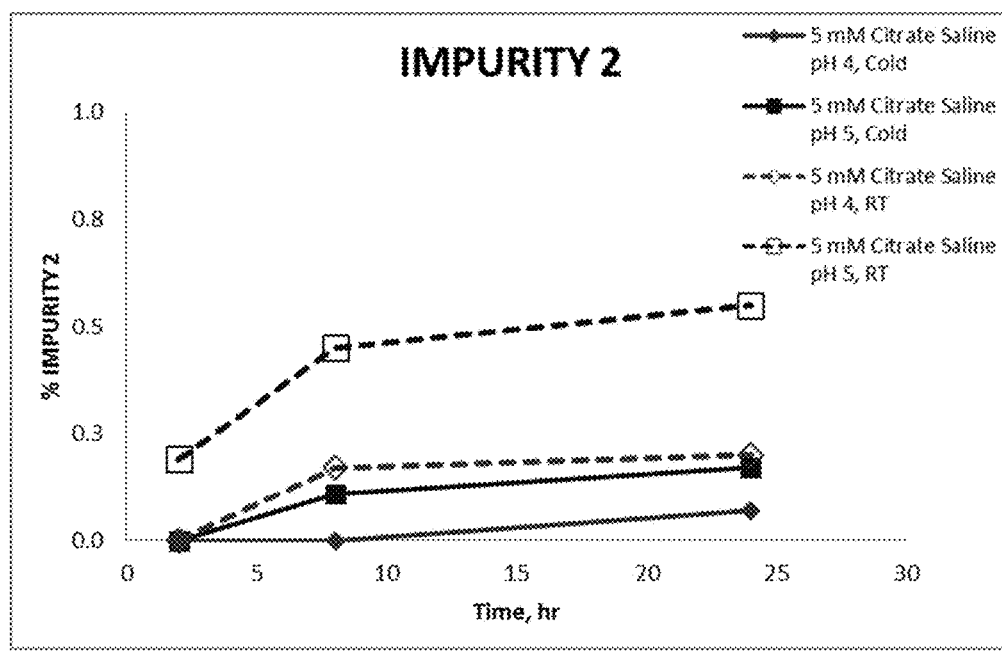
FIG. 7 shows formation of Impurity 2 a mock scale-up process at room temperature versus cold temperatures.

For the mock manufacturing process, the room temperature samples were formulated and stored at room temperature for a total of 8 hrs and then refrigerated overnight. In contrast, the cold samples were formulated on ice, stored in the 2-8° C. for a total of 8 hrs, and at the end of the day frozen to −20° C. The total amount of Impurity 1 and Impurity 2 are shown in FIGS. 6 and 7, respectively.

The formation of Impurity 1 was greater when formulated at room temperature (~0.8% after 24 hrs.) as opposed to formulation under cold conditions (<0.3% after 24 hrs.). This trend was observed at each of the time points taken. Similarly, the formation of Impurity 2 was slightly greater when formulated at room temperature (~0.3% after 24 hrs.) when compared to formulation under cold conditions (~0.1% after 24 hrs.). Therefore, it is recommended to manufacture and store the Compound 8 drug product under cold conditions (2-8° C.) to minimize the degradation products, Impurity 1 and Impurity 2.

Figure 8:
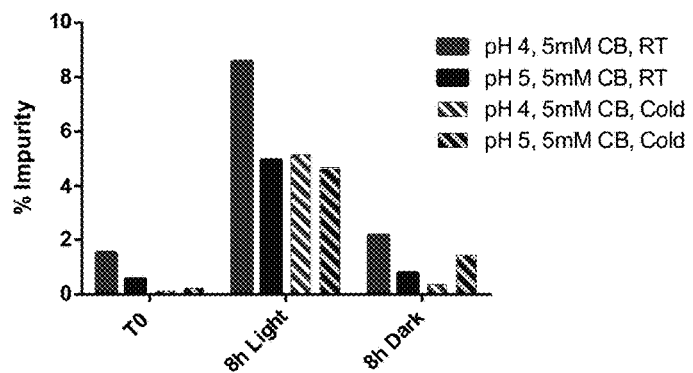
FIG. 8 shows Impurity 1 formation after mock process and clinical dilution in saline (CB: citrate buffer).
Figure 9:
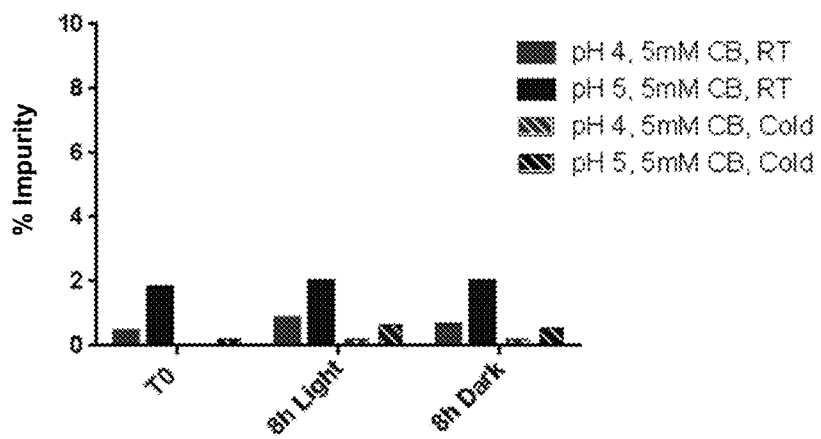
FIG. 9 shows Impurity 2 formation after mock process and clinical dilution in saline (CB: citrate buffer).

In order to understand how the clinical dilution contributes to the total amount of impurities, the mock manufacturing process samples were thawed and diluted in saline. In addition, a comparison between light and dark conditions was conducted to understand the risk of exposing the formulations to light while in the clinic. After a dilution of 2.5-fold in saline, the Compound 8 solution was drawn up into two syringes. The dark samples were protected from light with aluminum foil and the light samples were stored directly underneath a fluorescent light bulb. Both mock manufactured Compound 8 solutions (room temperature and cold) were evaluated in the mock clinical dilution study and the results are shown in FIGS. 8 and 9.

At the initial time point, both degradation products are formed in smaller quantities when formulated under cold conditions than when compared to the formulation at room temperature. After exposure to light or dark for 8 hrs, both the amount of Impurity 1 and Impurity 2 are higher for the room temperature sample than for the cold sample. The total amount of impurities is the lowest for the formulation that was manufactured at cold temperatures and protected from light during dilution.

Based on the above results, it is recommended to supply Compound 8 in an amber vial. The drug product should be formulated at cold temperatures and stored frozen. For in-use applications, exposure to light during thaw and dilution should be minimized and the dosing solution should be covered with an amber bag.

Lot Dependence

Two lots of Compound 8 with different purities were compared in order to determine if there were any differences in the total amount of degradation products produced during formulation. Compound 8 lots CAL-69-73A (99% purity) and CAL-69-74A (97% purity) were evaluated in 5 mM citrate saline pH about 4 and about 5.

Figure 10:
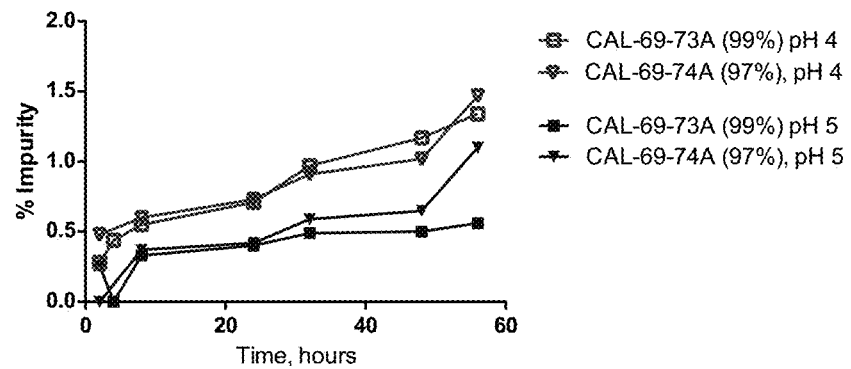
FIG. 10 shows Impurity 1 formation in two different DS lots in 5 mM citrate saline at both pH about 4 and about 5.
Figure 11:
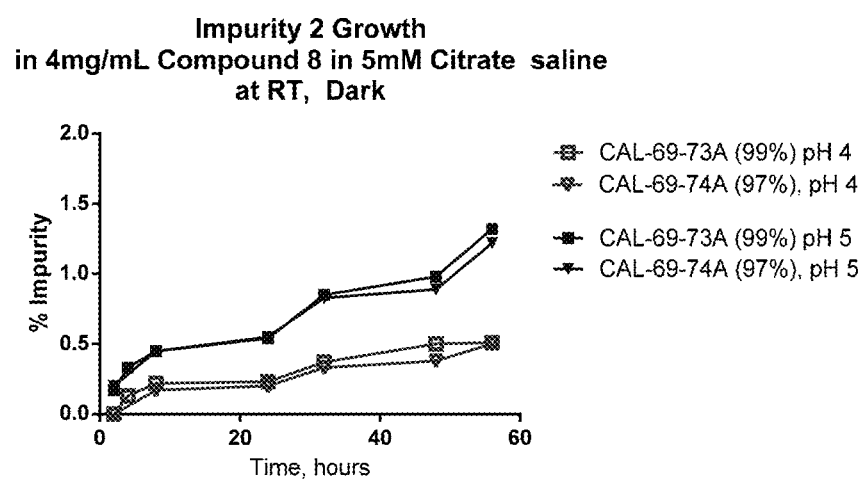
FIG. 11 shows Impurity 2 formation in two different DS lots in 5 mM citrate saline at both pH about 4 and about 5.

FIGS. 10 and 11 demonstrated that there were no significant differences observed between the two Compound 8 purity lots tested.

Saturated Solubility: 5 mM Citrate Saline pH about 4

The saturated solubility was tested by targeting a concentration between 10 to 20 mg/ml in 5 mM citrate saline pH about 4. The formulations were prepared by stirring at room temperature for 1 hr. They were protected from light to minimize the formation of the amine product (Impurity 1) during the formulation. The saturated solubility was also studied over a 24 hr period for some lots but due to compound degradation it was not further pursued for all lots. The saturated solubility of five drug substance lots is shown in Table 1.

TABLE 1

Compound 8 Saturated Solubility in
5 mM Citrate Saline pH about 4.

| Compound 8 Lot No. | Purity (Area %) | Saturated solubility in 5 mM citrate saline pH about 4, mg/mL |
|---|---|---|
| CAL-69-79A | 96.4 | >13.1 |
| CAL 69-38A | 96.8 | 19.8 |
| CAL-69-74A | 97.5 | 22.9 |
| CAL 80-09A | 98.9 | 8.1 |
| CAL 69-73A | 99.1 | 8.9 |

The saturated solubility of five different lots of Compound 8 ranged between 8 to 23 mg/ml in the vehicle. In some cases, the solutions were filtered and stored at 4° C. for 3-5 days. The concentration decreased slightly over time. It is suggested to filter the solutions immediately after preparation and then freeze in order to minimize the risk of seeding that may cause subsequent precipitation. Overall, the saturated solubility is estimated to be 9 mg/ml.

Methods

All samples were analyzed on an Agilent 1260 HPLC equipped with a binary pump and a diode array detector. An Agilent Poroshell 120 EC-C8 column was used with a bead diameter of 2.7 m (column size 4.6×50 mm). The column was equilibrated to 30° C. and the mobile phases consisted of A (0.1% trifluoroacetic acid [TFA] in purified distilled water) and B (0.1% TFA in acetonitrile [ACN]). The gradient was as follows:

| Time (min) | A % | B % |
|---|---|---|
| 0.00 | 95 | 5 |
| 4.50 | 5 | 95 |
| 5.00 | 5 | 95 |

The flow rate was set to 1.5 ml/min, the samples were diluted with 5 mM citrate buffer to a concentration of 1 mg/ml and were injected onto the HPLC with a 5 µl injection volume. Chromatograms were analyzed at 2 wavelengths. To determine the potency, area percent purity, and area percent of Impurity 2, a wavelength of 254 nm was monitored. The relative amount of Impurity 1 was determined by observing a wavelength of 310 nm. Standards were made in N,N-dimethyl formamide (DMF) for the studies.

Excipients

Mannitol is the most commonly used lyophilization bulking agent. The concentration of mannitol in the bulk filling solution, 2.5% (w/w) is the minimum concentration of those evaluated experimentally that provided an acceptable cake.

The combination of citric acid and sodium citrate forms a 5 mM citrate buffer pH about 4-5 in the bulk filling solution. Citrate buffer is a commonly used parenteral buffer. The 5 mM concentration is the minimum of the buffer strengths experimentally evaluated that was effective in stabilizing Compound 8 during processing.

Compostions with or without mannitol were compared. Solution stabilities at 2-8° C. were tracked for 7 days. Freeze thaw (F/T) stabilities were tracked for 3 cycles. As shown in the table below, with mannitol, % T0 (% T0 is the percent recovery compared to T0 (initial) in terms of concentration) of Compound 8 was 99.8% after storing at 2-8° C. for 7 days. % Area for Compound 8 was 98.5% and only 0.12% and 0.18% for Impurity 1 (Im.1) and Impurity 2 (Im.2). Without mannitol, Compound 8's % T0 was only 97.6% after storing at 2-8° C. for 7 days. % Area for Compound 8 was only 97.6%, while Impurity 1 had % Area of 0.67 and Impurity 2 had % Area of 0.22. Therefore, the data in the table below showed an unexpected benefit of mannitol on the formulation stability of Compound 8. Compound 8 was more stable in the compostion with mannitol at 2-8° C. and under F/T cycles.

| Sample Name | Storage Conditions | Assay Analysis ||||| % Area Analysis |||
|---|---|---|---|---|---|---|---|---|
| | | Comp. 8 RT min | Comp. 8 Conc mg/ml | Assay % | % T0 % | % Area ||||
| | | | | | | Comp. 8 | Im. 1 | Im. 2 |
| 5 mg/ml of Comp. 8 in 5 mM Citrate Saline pH about 4.0 | Initial | 3.42 | 5.048 | 101.0% | N/A | 98.8 | ND | ND |
| | 1 day, 2-8° C. Storage | 3.41 | 5.017 | 100.3% | 99.4% | 98.7 | 0.09 | ND |
| | 2 day, 2-8° C. Storage | 3.41 | 4.977 | 99.5% | 98.6% | 98.4 | 0.24 | 0.08 |
| | 3 day, 2-8° C. Storage | 3.40 | 4.938 | 98.8% | 97.8% | 98.2 | 0.49 | 0.12 |
| | 7 day, 2-8° C. Storage | 3.40 | 4.928 | 98.6% | 97.6% | 97.9 | 0.67 | 0.22 |
| | 1 F/T Cycle | 3.42 | 5.002 | 100.0% | 99.1% | 98.7 | 0.13 | ND |
| | 2 F/T Cycles | 3.40 | 4.983 | 99.7% | 98.7% | 98.6 | 0.20 | ND |
| | 3 F/T Cycles | 3.40 | 5.015 | 100.3% | 99.3% | 98.6 | 0.21 | ND |
| 5 mg/ml of Comp. 8 in 2.5% Mannitol, 5 mM Citrate Saline pH about 4.0 | Initial | 3.42 | 5.058 | 101.2% | N/A | 98.8 | ND | ND |
| | 1 day, 2-8° C. Storage | 3.41 | 5.068 | 101.4% | 100.2% | 98.7 | 0.08 | ND |
| | 2 day, 2-8° C. Storage | 3.42 | 5.039 | 100.8% | 99.6% | 98.7 | 0.08 | ND |
| | 3 day, 2-8° C. Storage | 3.40 | 5.034 | 100.7% | 99.5% | 98.6 | 0.11 | 0.08 |
| | 7 day, 2-8° C. Storage | 3.40 | 5.046 | 100.9% | 99.8% | 98.5 | 0.12 | 0.18 |
| | 1 F/T Cycle | 3.41 | 5.070 | 101.4% | 100.2% | 98.7 | 0.10 | ND |
| | 2 F/T Cycles | 3.41 | 5.034 | 100.7% | 99.5% | 98.7 | 0.10 | ND |
| | 3 F/T Cycles | 3.40 | 5.054 | 101.1% | 99.9% | 98.6 | 0.16 | ND |

Conclusions

Compound 8 is formulated at a drug concentration of 3-5 mg/mL in 5 mM citrate buffer at about pH 4 and 5% mannitol. It is recommended that the formulation be prepared in an amber vial under cold conditions (2-8° C.) and stored frozen to minimize the formation of degradation products, Impurity 1 and Impurity 2. During clinical dilution, it is suggested that Compound 8 be protected from light. Compound 8 is sensitive to light, pH, and temperature. During early stages of formulation development it was discovered Compound 8 forms two major impurities while in aqueous solution. The first impurity, Impurity 1, is a free amine without a platinum group that can develop when the formulation is exposed to light. The second impurity, Impurity 2, is a ring-opening product of the maleimide group which forms primarily at pH values above 6. The rate for both processes decreases with decreasing temperature.

Accordingly, to ensure a high level of purity and maximize stability, Compound 8 was formulated with a citrate buffer (to maintain a low pH), lyophilized (to minimize hydrolysis), and packaged in an amber vial (to minimize exposure to light).

In summary, Compound 8 Powder for Injection is a sterile lyophilized powder containing Compound 8, a cisplatin pro-drug, along with mannitol, sodium citrate and citric acid. Each dosage unit contains 100 mg of Compound 8 in a stoppered 50 mL amber vial. Nominal fill is 20 mL. Prior to administration, the product is reconstituted with 20 mL aqueous solution of 0.45% sodium chloride to yield a 5 mg/mL isotonic solution of Compound 8 in 5 mM citrate buffer, 0.45% sodium chloride and 2.5% mannitol.

The composition of Compound 8 powder for injection is shown in Table 2.

TABLE 2

Composition of Compound 8 Powder for Injection

| Component | Nominal amount per vial (mg) | Weight Percent (% w/w) | Function | Quality |
|---|---|---|---|---|
| Compound 8 | 100 | 0.500 | Active | GMP |
| Mannitol, Low endotoxin | 500 | 2.500 | Bulking agent | USP |
| Citric acid monohydrate[a] | 12.5 | 0.062 | Buffer stabilizer | USP |
| Sodium citrate dihydrate[a]Error! Reference source not found. | 11.6 | 0.058 | Buffer stabilizer | USP |

[a]Based on starting material

Alternatively, each dosage unit of Compound 8 Powder for Injection may also contain 50 mg Compound 8 in a stoppered 50 mL amber vial. pH is maintained at about 4 with 5 mM citrate buffer/saline. Nominal fill in each vial is 10 mL.

Example 3

Manufacturing Process of Compound 8 Powder for Injection

The drug product process begins by preparation of a chilled, solution of 2.5% mannitol and 5 mM citrate buffer (pH about 4-5) solution to which Compound 8 drug substance is added at concentration of 5 mg/mL. The saturated solubility of the drug substance in this buffer was shown experimentally to be 16-17 mg/mL. The bulk solution is filter (0.2 μm) sterilized, aseptically filled into vials, and lyophilized. To minimize Compound 8 degradation, the bulk solution is maintained chilled and protected from light during processing. Lyophilizing Compound 8 as a dry powder was selected as the best means to minimize hydrolysis during storage. Finally, filter sterilization was chosen as the most benign means to sterilize the drug product.

Container Closure System [Compound 8 Powder for Injection]

The container closure system uses standard pharmaceutical container closure components for sterile lyophilized products. The amber serum bottle was chosen to protect the product from light. The rubber stopper is constructed with a fluoropolymer film barrier designed to minimize drug product interaction with the closure.

Compatibility [Compound 8 Powder for Injection]

The drug product reconstituted solution is compatible with the commercially available i.v. infusion bags and administration sets dose.

Batch Formula [Compound 8 Powder for Injection]

The current batch size of Compound 8 Drug Product is provided in Table 3 and the batch formula is provided in Table 15.

TABLE 3

Compound 8 Drug Product Batch Size

| Product (strength) | Batch Size | Number of Vials (Nom.) |
| --- | --- | --- |
| 100 mg | 25 L | 1250 |

TABLE 4

Compound 8 Drug Product Batch Formula
Bulk Solution

| Component | Quality Standard | Amount % (w/w) | Amount (g) per Batch |
| --- | --- | --- | --- |
| Compound 8 | cGMP | 0.05 | 126.1 |
| Mannitol, low endotoxin | USP | 2.5 | 630.6 |
| Sodium citrate dihydrate | USP | 0.0582 | 14.7 |
| Citric acid monohydrate | USP | 0.0624 | 15.8 |
| WFI | USP | QS to 100% | QS to 25,223$^a$ (25,000 L) |
| Total Batch Size | | | 25,000 L |

$^a$Based on density of 1.0089 g/mL Description of Manufacturing Process and Process Controls [Compound 8 Powder for Injection]

Manufacturing Process

Figure 12:
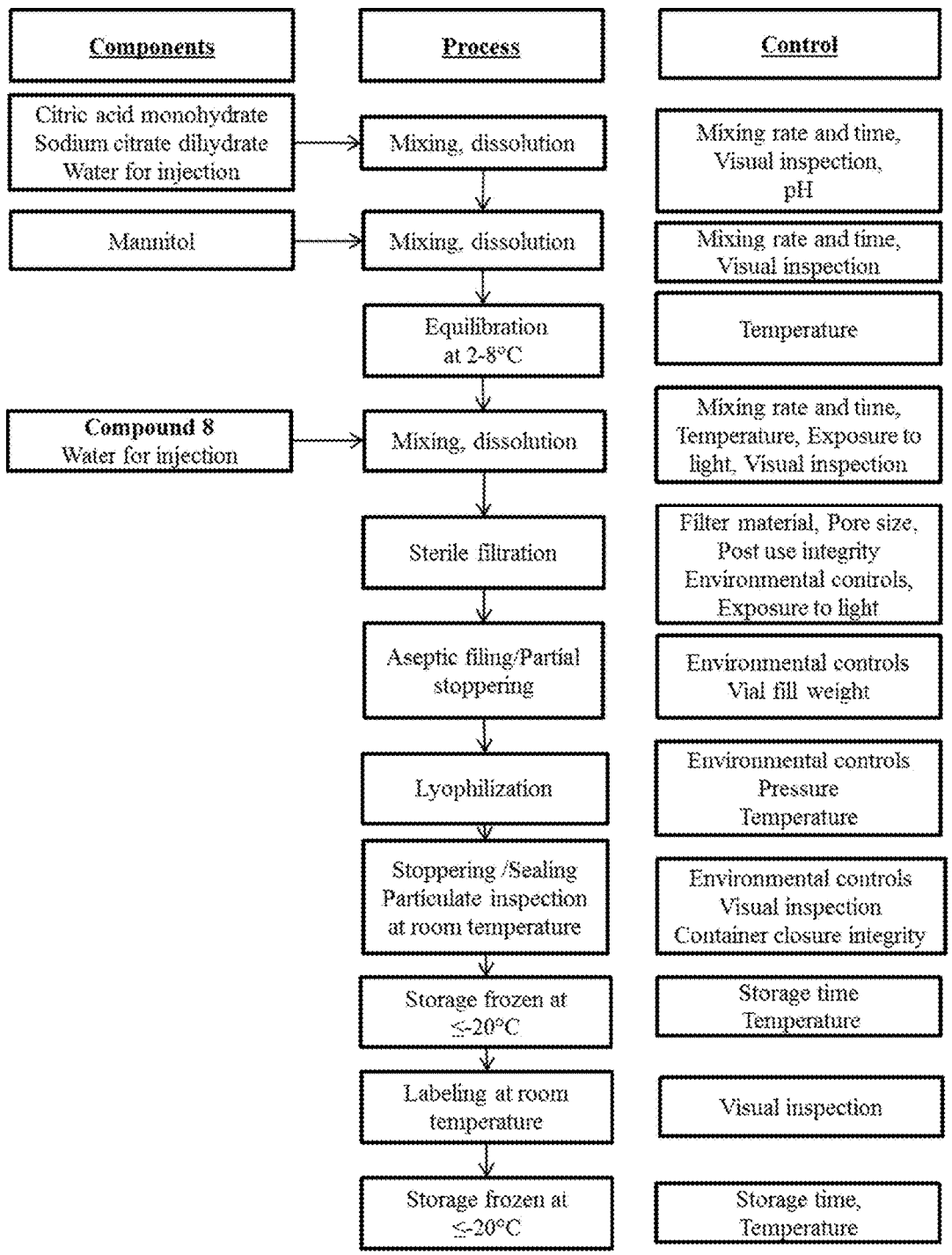
FIG. 12 shows Compound 8 Powder for Injection manufacturing process flow diagram.

A flow diagram for the manufacturing and packaging processes for Compound 8 Powder for Injection Drug Product is provided in FIG. 12.

Manufacturing Process Description

Compound 8 Powder for Injection manufacturing occurs in Class 100,000 room under yellow light. Aseptic processing steps are performed in a VHP decontaminated isolator.

Bulk solution is prepared by dissolving required amounts of sodium citrate, citric acid and mannitol into 90% of the required volume of WFI in a 25 L stainless steel, jacketed vessel with agitator at ambient temperature. The bulk solution is then cooled to 2-8° C. and after ensuring pH is in the accepted range of 4.0-4.5, Compound 8 drug substance is then added and mixed until dissolved. Additional WFI is added to QS to the target volume.

Aseptic vial filling occurs via an automated fill/stopper/capper machine in a VHP decontaminated isolator under yellow light. Bulk solution is intermittently pumped though porting in the isolator wall and a series of redundant sterile filters (0.2 μm) into a closed, steam sterilized, stainless steel, jacketed (2-8° C.) collection vessel. From the collection vessel the solution is dispensed (nominal fill 20 mL) into 50 mL amber vials. Alternatively, the solution is dispensed (nominal fill 10 mL) into 50 mL amber vials to reduce vial breakage. The vials are partially stoppered and transferred onto trays which, in turn, are transferred to the lyophilizer with a 5° C. shelf set point temperature. During the vial transfer, the lyophilizer opens into the isolator.

The lyophilization cycle starts with a rapid freeze to −45° C. (shelf set pt.) followed by annealing at −10° C. (shelf set pt.). Primary dry begins with a rapid freeze to −45° C. (shelf set pt.), vacuum started and shelf temperature set point increased to −10° C. (product critical temperature: −5° C.). On completion of primary dry, secondary drying begins by increasing the shelf temperature set point to 30° C. On completion of the cycle, the lyophilizer is back filled with sterile nitrogen and stoppers fully seated.

The vials are moved from the lyophilizer into the isolator and capped. Product vials are held at 2-8° C. prior to inspection and sampling for release testing. The vials are then stored at −20° C. and shipped to the distributor on dry ice for primary labelling, storage and distribution.

Description of the in Process Controls

Dissolution of Compound 8

To maintain stability, Compound 8 in solution must be kept at low pH and temperature, and protected from light. This is accomplished by the following control measures:

All open manufacturing processes are conducted under yellow light;

Bulk solution is compounded and stored in a closed, stainless steel, jacketed vessel with temperature maintained at 2-8° C. during processing;

During filling, bulk solution is maintained in a closed, stainless steel, jacketed surge vessel controlled at 2-8° C.;

The citrate buffer is formulated for pH about 4.2;

Filled vials are maintained in the lyophilizer at a shelf temperature set point of 5° C. until filling is complete.

Sterility

To ensure sterility of product the following controls are employed:

Environmental monitoring;

Product is processed through redundant sterile filters (0.2 μm). (Post-process integrity acceptance is based on single filter passing bubble point test);

Aseptic filling process is validated by process simulation using microbiological media (TSB) bracketing the largest and smallest containers used on the filling line;

The isolator VHP decontamination procedure has been validated;

The lyophilizer sterilization cycle has been validated.

Lyophilization

To ensure a good quality, easily reconstituted cake with low moisture content and the following controls were employed:

Lyophilization cycle was designed based on thermal characteristics of product and confirmed in pilot scale studies;

Cycle is pre-programmed into lyophilizer and temperature and pressure continuously recorded and monitored.

Controls of Critical Steps and Intermediates [Compound 8 Powder for Injection]

The in-process tests listed in Table 5 are employed to control several of the critical steps of the Compound 8 Powder for Injection Drug product manufacturing process.

TABLE 5

Target and In-Process Test Limits in Manufacture of Compound 8 Powder for Injection Drug Product

| Process step | Test | Target and In-Process Test Limits |
| --- | --- | --- |
| Prior to dissolving Compound 8 into bulk solution, pH and temperature must be with specified ranges. | pH<br>Temperature | Range: 4.0-4.5<br>Range 2-8° C. |
| To ensure sterility of product | Environmental viable and non-viable monitoring | Compatible with appropriate USP environmental classification |
| Vial fill weight is checked periodically during the filling operation and must be within specified target and acceptance limits: | Vial weight checks | Target: 20.35 g$^a$<br>Action limit: 19.74-20.96 (±3%)<br>(Requires pump adjustment)<br>Reject limit: 19.33-21.36 (±5%) |
| Programmed in the lyophilization cycle is a "pressure rise" test to ensure free water is removed prior to raising temperature for secondary drying, thus avoiding cake collapse | Lyophilizer pressure rise test | Vacuum is isolated from the chamber and chamber pressure monitored. Pressure rise must be less than 30 mTorr in 20 sec before proceeding with the secondary drying stage. |
| Cap seals are checked periodically during the capping process for proper seal. | Cap seal check | Caps are checked for visual appearance of proper rolled crimp and absence of cracks, splits or dents. Looseness is checked by trying to twist the cap. |
| At conclusion of manufacturing 100% of vials are visually inspected for quality appearance | Visual inspection | Vials are inspected for particulate matter, discoloration, vial and seal defects, cake quality, and product around stopper. |

$^a$Includes overfill to ensure delivery of 100 mg in 20 mL reconstitution fluid.

Batch Information and Analytical Results

The drug product Compound 8 Powder for Injection, 100 mg/vial in 50 mL vials, or 50 mg/vial in 50 mL vials, for use in the proposed clinical trial was manufactured in an aseptic environment using the process described in Description of the in Process Controls. Three batches (two development and one clinical) have been prepared using the same process, same grade excipients and solution composition. The first development batch was prepared at 10 mg/vial with a 2 mL fill before lyophilization. The subsequent batches have been prepared at 100 mg/vial with a 20 mL fill, or 50 mg/vial with 10 mL fill, before lyophilization. After reconstitution both the 10 mg and 100 mg are at 5 mg/mL as shown in Table 6. Also after reconstitution the 50 mg vial is at 5 mg/mL. The associated batch analysis data of the 10 mg and 100 mg batches are shown in Table 7.

TABLE 6

Batch Information Summary for Compound 8 Powder for Injection, 10 mg/vial and 100 mg/vial

| Lot Number | Lot Size (units) | Strength (mg)/ Fill(mL)/ Bottle(Size (mL) | Date of Manufacture | Material Use |
| --- | --- | --- | --- | --- |
| DNR-079-58 | 189 | 10/2/10 | February, 2015 | Stability |
| 0148-15008-8 | 22 | 100/20/50 | February, 2015 | Familiarization Batch |
| 0148-15008-13 | 131 | 100/20/50 | March, 2015 | Engineering batch |
| | | 100/20/50 | | Clinical Studies, Stability |

TABLE 7

| Batch Analysis Results for Compound 8 Powder for Injection | | | | | |
|---|---|---|---|---|---|
| Lot No. | | DNR-079-58 | 0148-15008-8 | 0148-15008-13 | |
| Dosage Strength | | 10 mg | 100 mg | 100 mg | |
| Batch Size (solution mass) | | 189 vials (0.5kg) | 500 mL | 4 L | |
| Drug Substance Lot number | | CAL-80-52A | BTPQR-001 | BTPQR-002 | 154BT P01 |
| Test Method | Proposed Specification | Result | Result | Result | Result |
| Appearance | Lyo cake to clump in amber vials | Conforms | Conforms | Conforms | |
| Identification | Retention time consistent with reference standard | Conforms | Conforms | Conforms | |
| Assay | 90.0-110.0% of label claim of the nominal amount | 100.0% | 99.4 (Assay) | 99.5% (Assay) | |
| Degradation Products | Individual NMT 1.0% Total NMT 5.0% | Impurity 1 = 0.15% Total = 0.15% | Total: 0.5% | Total 0.10% | |
| Uniformity of Dosage: Weight Variation | Conforms to USP <905> | NT | NT | NT | |
| pH$^a$ | 3.8-5.0 | 4.1 | 4.3 (WFI) | 4.2 (WFI) | |
| Reconstitution time$^a$ | Report results | NMT 1 min | <5 sec (WFI) | <5 sec (WFI) | |
| Particulate Matter$^a$ | Conforms to USP<788> | NT | NT | 196/container (≥10 μm) 2/container (≥25 μm) | |
| Moisture | Report Results | 0.4% | 0.5% | 0.7% | |
| Endotoxin | ≤0.250 EU/mg | NT | NT | ? | |
| Sterility$^b$ | Sterile | NT | NT | NT | |
| Osmolality | Report Results | NT | NT | NT | |

$^a$NMT: Not More Than
$^b$NT: Not Tested

Example 4

Toxicology Studies of Compound 8

Compound 8 is a novel albumin-binding prodrug of cisplatin. The evaluation of its pharmacokinetics properties showed that it is highly protein bound (≥99%) and leads to high platinum levels in the plasma of mouse, rat and dog following an intravenous administration.

Compound 8 toxicity was evaluated in single and repeat dose non-clinical toxicology studies. The list of the studies summarized in this section is presented in Table 8 below.

TABLE 8

| Toxicology Studies | | | | |
|---|---|---|---|---|
| Study type | Duration | Route of Administration | Species | Compound Administered |
| A Single dose intravenous DRF* toxicity study in male rats (non-GLP) (Compound 8-TX-001) | 10 days Dose on Day 1 | Intravenous injection | Male rats | Compound 8 |
| A Single dose intravenous DRF* toxicity study in beagle dogs (non-GLP) (Compound 8-TX-002) | 12 days Dose on Day 1 | Intravenous injection | Male and female dogs | Compound 8 |
| A repeat-dose intravenous toxicity study in rats with a 3-week recovery period (Including Supportive Toxicokinetic Evaluation) (GLP) (Compound 8-TX-007) | 6 weeks (include 3 week recovery period) Dose on Day 1 and 21 | Intravenous injection | Male and female rats | Vehicle Compound 8 Cisplatin |

*DRF—Dose Range-Finding

The single dose studies were designed as dose range-finding (DRF) studies to assist the dose and species selection for the repeat dose toxicity study and the dose selection for the cardiovascular toxicity study in dogs.

Rat was selected for the repeat-dose study as the more sensitive species based on the results from the DRF studies in rats and dogs, literature data showing that rat is a predictive model for platinum drugs (Paul A Andrews, David D. Smith, et. al, "Predictive Value of Preclinical Toxicology Studies for Platinum Anticancer Drugs", Clin Cancer Res, 1999; 5: 1161-1167), the contents of which are incorporated herein by reference in their entirety. The MTD or STD10 determined in the rat DRF study, 19 mg/kg (122 mg/m$^2$) is lower than the MTD of 10 mg/kg (200 mg/m$^2$), determined in the dog DRF study. In addition, there were no mortalities or treatment related clinical observations in dog up to 12 mg/kg (240 mg/m$^2$) while unscheduled deaths in rat were observed at 27 mg/kg (162 mg/m$^2$) with no mortalities at lower doses in the rat.

The repeat dose study in rat also included cisplatin as a comparator at 6 mg/kg dose that was expected to produce measurable toxicity and extrapolated to 36 mg/m$^2$ HED falling in the Cisplatin clinical range (20-100 mg/m$^2$) to benchmark potential clinical toxicity.

Toxicity and toxicokinetic (TK) assessments were conducted for both Compound 8 and Cisplatin. The exposure to the test article (Compound 8 or Cisplatin) was determined by analyzing the total platinum concentration in the plasma, plasma ultrafiltrate, and red blood cell (RBC) pellets. Platinum in the plasma ultrafiltrate was considered free drug (non-protein bound), while the platinum in the plasma was a combination of protein bound and free drug. The difference between these two concentrations is representative of the protein bound drug (Compound 8 or Cisplatin).

For Compound 8, the mean systemic exposure to platinum increased in an approximate dose-proportional manner across the dose range for plasma, RBC pellets and ultrafiltrate and was highest in the plasma and lowest in the ultrafiltrate, meaning that the predominant fraction of the drug in the plasma is protein-bound. In the Cisplatin group dose normalized exposure in plasma was lower that the plasma exposure in Compound 8 treated animals, however, the dose normalized exposures in RBC pellets and ultrafiltrate were greater than those from Compound 8 treated animals.

There were no deaths and no effects were noted in clinical observations, functional observation battery (FOB) assessments or ophthalmic examinations following treatment with Compound 8. FOB findings in Cisplatin group included a slight increase in the incidence of palpebral closure following dosing on Day 1, increased thermal response time following the second dose and a slight decrease in mean forelimb strength at the end of the recovery.

Body weights were decreased in Compound 8 treated animals relative to the vehicle group transiently through Day 7 (9 mg/kg) or throughout the treatment period (14 and 19 mg/kg). The Cisplatin dose (6 mg/kg) group exhibited treatment-related, decreases in body weights in male and female rats, relative to the vehicle group, that were comparable to rats in the highest dose (19 mg/kg) group for Compound 8. During the recovery period, the body weights for the males receiving 14 mg/kg Compound 8 and females receiving 19 mg/kg Compound 8 were comparable to the vehicle treated animals, indicating a slight reversal towards normalcy. Conversely, the Cisplatin-treated animals continued to exhibit decreased body weights which tended to become more severe during the recovery period, relative to the vehicle group.

Most of the hemathology and clinical chemistry findings were similar for Cisplatin (6 mg/kg) and the highest dose (19 mg/kg) Compound 8 group. However, the changes attributable to altered renal function were generally greater in the Cisplatin group. For instance dose dependent mild increase in creatinine concentration at 19 mg/kg to +76% (males) and +18% (females) observed as compared to +288% (males) and +103% (females) increase in creatinine in the rats dosed with 6 mg/kg Cisplatin group. Mild increase in the urea nitrogen at 19 mg/kg Compound 8 to +14% in the male rats observed as compared to +386% (males) and 150% (females) at 6 mg/kg Cisplatin.

Clinical chemistry changes unique for the Cisplatin group included mild to moderate decreases in sodium, potassium and/or chloride concentrations. Changes unique to Compound 8 treated animals were limited to dose dependent mild increase in alanine aminotransferase (ALT) at the end of the terminal phase and resolved completely during the recovery stage. Changes seen in both groups but more pronounced in Compound 8 treated animals included elevated fibrinogen, aspartate aminotransferase (AST), amylase, lipase, globulin, and triglyceride levels all of which decreased or were completely resolved during the recovery stage.

At the terminal necropsy, Compound 8-related microscopic findings were limited to: kidneys in males at ≥9 mg/kg and in females at ≥14 mg/kg; bone marrow (femur/sternum) and pancreas in males and females at ≥9 mg/kg; thymus of males and females at ≥14 mg/kg, last injection site, stomach (glandular and nonglandular) and skin in males and females at 19 mg/kg, and testes and epididymides in males ≥9 mg/kg.

Cisplatin-related microscopic findings at 6 mg/kg were limited to the kidneys, bone marrow, thymus, and skin of terminal males and females; microscopic findings were of similar characterization as previously discussed for the Compound 8 groups. Testicular changes were noted in Cisplatin treated animals at an increased incidence/severity than those findings noted in BTP114 treated males. Microscopic findings at the last injection site were limited to slightly increased severity of inflammation in the terminal males and increased incidence of pancreatic apoptosis was only noted in terminal females. In general, the microscopic findings were of increased incidence and/or severity when compared to 19 mg/kg Compound 8 groups.

Following the completion of the three-week recovery period, findings noted in the Compound 8 treated groups generally tended to reverse towards normalcy with the exception of noted changes in platelet counts, cholesterol concentration, urine pH, creatinine clearance, and testicular changes. Similar findings were noted in the Cisplatin treated group at the end of the three-week recovery period.

Based on the adverse findings noted in the Compound 8 dose groups, the STD$_{10}$ (the dose that causes death or irreversible severe toxicity in 10% of the animals) based on rat repeat dose study was projected to be ≥19 mg/kg (≥114 mg/m$^2$).

There is an extensive body of published literature regarding the preclinical evaluation of multiple platinum compounds, including cisplatin. The toxicities associated with platinum compounds are well established, with the principal toxicities including nausea and vomiting; nephrotoxicity; neurotoxicity (sensory neuropathy); ototoxicity; and myelosuppression. The DLTs of platinum drugs seen in Phase 1 studies, namely myelosuppression, gastrointestinal toxicities nephrotoxicity, and neurotoxicity, were predicted nonclinically in studies in the rodent and dog (Diana L. Clark, Paul A Andrews, David D. Smith, et. al, "Predictive Value of Preclinical Toxicology Studies for Platinum Anticancer Drugs", Clin Cancer Res, 1999; 5: 1161-1167, the contents of which are incorporated herein by reference in their entirety).

Given the extensive nonclinical and clinical data available with platinum drugs, and cisplatin in particular, the nonclinical toxicology program for Compound 8 is limited to two single-dose toxicity studies in the rat and dog, and a repeat-dose toxicity study in the rat. The single dose studies were designed as DRF studies to assist the dose and species selection for the GLP repeat-dose toxicity study and the dose selection for the GLP safety pharmacology study in the dog.

The rat was selected for the repeat-dose study as the more sensitive species based on the results from the DRF studies in rats and dogs and literature showing that rat is a predictive model for platinum drugs (Diana L. Clark, Paul A Andrews, David D. Smith, et. al, "Predictive Value of Preclinical Toxicology Studies for Platinum Anticancer Drugs", Clin Cancer Res, 1999; 5: 1161-1167, the contents of which are incorporated herein by reference in their entirety). The MTD and $STD_{10}$ determined in the rat DRF study, 19 mg/kg (122 mg/m$^2$), is lower than the MTD of 10 mg/kg (200 mg/m$^2$) determined in the dog DRF study. In addition, there were no mortalities or treatment related clinical observations in dogs up to 12 mg/kg (240 mg/m$^2$), whereas unscheduled deaths in rats were observed at 27 mg/kg (162 mg/m$^2$).

The repeat-dose study in rat included cisplatin as a comparator at a dose of 6 mg/kg, a dose expected to produce measurable toxicity and extrapolated to a HED of 36 mg/m$^2$, a dose within the cisplatin clinical range (20-100 mg/m$^2$) to benchmark clinical toxicity.

Single Dose Studies

Two single dose toxicology studies were conducted with Compound 8, 1 in the rat and another in the Beagle dog.

A Single Dose Intravenous Dose Range-Finding Toxicity Study in Male Rats

This study (Compound 8-TX-001) was designed as a dose range finding study to support the dose selection for the repeat-dose IV toxicity GLP study in rats (Compound 8-TX-007).

The test article, Compound 8, was formulated prior to dosing as a solution in 5 mM citrate buffered saline (0.9% sodium chloride), pH about 4-4.5, at nominal concentrations of 2.7, 1.4, 1.9, and 2.3 mg/mL. Compound 8 was administered via IV injection to groups of 3 animals each at doses of 27, 14, 19, and 23 mg/kg. Dose formulations were all within the acceptance criteria (±10% of target concentration) ranging from 98.8 to 106.2 percent of target concentration. Assessment of toxicity was based on mortality, clinical observations, body weight, and food consumption, and clinical and anatomic pathology.

There were 2 unscheduled deaths during the course of the study. Two rats in Group 1 (27 mg/kg) were found dead on Day 7. Both animals lost weight throughout the study and were observed with clinical observations, including thin appearance, red material around the nose, piloerection, decreased activity, and/or cold to touch. In addition, mild to moderate depletion of thymus cells, moderate depletion of white and red pulp in the spleen, and moderate to marked nephropathy were noted. The study pathologist considered the cause of death for both rats was acute renal failure. Additional observations noted in surviving animals included thin appearance in one animal receiving 27 mg/kg Compound 8 and hind feet and fore feet cold to touch in one animal receiving 23 mg/kg Compound 8. Decreases in body weight were noted throughout the study at doses ≥23 mg/kg. In addition, transient decreases in body weight were noted at doses ≤19 mg/kg through Day 4. Decreased body weights correlated with decreased food consumption in all groups.

Evidence of reduced renal function and renal injury was noted in rats receiving Compound 8 at doses ≥14 mg/kg, including one or more of the following: increased in serum urea nitrogen, creatinine, and phosphorus, low urine specific gravity, presence of glucose and/or protein in the urine, and/or increased urinary renal injury markers (i.e., kidney injury molecule-1, neutrophil gelatinase-associated lipocalin, albumin, and osteopontin). The changes in urea nitrogen and creatinine demonstrated partial to full resolution at the terminal collection in rats administered 14 and 19 mg/kg Compound 8, but progressed in magnitude in males administered 23 and 27 mg/kg. Electrolyte changes, considered secondary to renal injury, including decreases in sodium and chloride, and/or increases in potassium, were also present at doses ≥19 mg/kg, while decreases in albumin were also noted in rats administered ≥19 mg/kg, which was likely secondary to protein loss in the urine.

Evidence of an inflammatory response was noted in rats at doses ≥19 mg/kg, including increased total leukocytes, neutrophils, monocytes, and/or lymphocytes. In addition, changes that were likely due to reduced hematopoiesis (decreased reticulocytes and platelets) were noted in rats administered 23 mg/kg Compound 8.

Histopathologically significant findings noted included mild to marked acute nephropathy, mild to severe thymus depletion, and mild to moderate splenic depletion and lymphoid hyperplasia. Minor findings were also observed in liver, testes, and potentially thyroid glands. Groups 1 and 4 (27 and 23 mg/kg, respectively) had the most prominent kidney findings while Groups 2 and 3 (14 and 19 mg/kg, respectively) had kidney findings more typical of reversible changes.

Based on the results of this study and having in mind the small number of animals per group (N=3), the MTD and $STD_{10}$ were determined to be ~19 mg/kg. Therefore 19 mg/kg was selected as the highest dose in the repeat dose IV toxicity study in rats.

A Single Dose Intravenous Dose Range-Finding Toxicity Study in Beagle Dogs

This study (Compound 8-TX-002) was conducted to evaluate and characterize the acute toxicity and to determine an MTD of Compound 8 when administered once via IV injection to the dog, and to assist in dose selection for a subsequent dog cardiovascular study (Compound 8-TX-005). The test article, Compound 8, was formulated prior to dosing, as a solution in 5 mM citrate buffered saline (0.9% sodium chloride), pH about 4-4.5 at nominal concentrations of 1.2, 2.4, 4.0, and 4.8 mg/mL. Dose formulations were all within the acceptance criteria (±10% of target concentration) ranging from 92.1 to 99.8 percent of target concentration.

Groups of 2 animals each (1 male, 1 female) received Compound 8 at doses of 3, 6, 10, or 12 mg/kg. Assessment of toxicity was based on mortality, clinical observations, body weight, and qualitative food assessment; physical examinations; and clinical pathology. Toxicokinetic assessment was conducted for platinum concentration in the plasma and plasma ultrafiltrate.

There were no mortalities during the study and no treatment-related clinical observations.

Decreases in body weight (generally dose-related) were noted in male and female dogs in all dose groups and exceeded 10% in the 12 mg/kg animals. In the 10 and 12 mg/kg dose groups, this decrease in body weight correlated with sporadic decreases in qualitative food consumption.

General trends in hematology parameters (decreases in reticulocytes, red cell mass, neutrophils and platelets) were noted in both sexes and all groups and were indicative of bone marrow/hematopoietic effects that did not consistently follow a dose response and tended to become more pronounced at Days 4 and 10 relative to Day 2. There were no definitive effects of Compound 8 on chemistry, coagulation, or urinalysis parameters.

Based on the results of this study, the MTD was determined to be 10 mg/kg (200 mg/m$^2$). Based on these results the doses selected for the dog cardiovascular toxicity study were 6 and 10 mg/kg.

Repeat-dose Studies

One repeat-dose toxicology study has been conducted in the rat.

A Repeat-Dose Intravenous Toxicity Study in Rats with a 3-week Recovery Period

Compound 8 toxicity was evaluated in a repeat-dose IV toxicity study in rats with a 3-week recovery period (Compound 8-TX-007). This study was conducted evaluate the potential repeat dose toxicity of the test article, Compound 8, in rats when administered on Days 1 and 21, and to evaluate reversibility, progression, or delayed appearance of observed changes following a 3-week post dose observation period. Groups of 30 animals (15/sex) each received vehicle control or Compound 8 9, 14, 19, or 6 mg/kg. Groups of 20 animals (10/sex) received Compound 8 9, 14, 19, or 6 mg/kg and 6 animals (3/sex) received vehicle control in the TK portion of the study.

Assessment of toxicity was based on mortality, clinical observations, functional observational battery evaluations, body weight, and food consumption and efficiency; ophthalmoscopic examinations; and clinical and anatomical pathology. RBC pellet analysis was conducted for total platinum content.

Toxicity and TK assessments were conducted for the test article and positive control. The positive control, cisplatin, was used as comparator to benchmark clinical toxicity. The cisplatin dose of 6 mg/kg in rats extrapolates to 36 mg/m$^2$ HED (human estimated dose), which falls into the clinical dose range of cisplatin (20-100 mg/m$^2$, the most commonly used clinical dose of cisplatin is 75 mg/m$^2$).

There were no deaths and no effects were noted in clinical observations, FOB, or ophthalmic examinations following treatment with Compound 8. FOB findings noted in cisplatin-treated animals included a slight increase in the incidence of palpebral closure following dosing on Day 1; increased thermal response time following the second dose; and a slight decrease in mean forelimb grip strength at the end of recovery.

Body weights were decreased in Compound 8 treated animals transiently through Day 7 (9 mg/kg) or throughout the treatment period (14 and 19 mg/kg). Food consumption exhibited similar effects as BW. The cisplatin dose (6 mg/kg) group exhibited treatment-related, decreases in body weights in male and female rats, relative to the vehicle group, that were comparable to rats in the highest dose (19 mg/kg) group for Compound 8. During the recovery period, the body weights for the males receiving 14 mg/kg Compound 8 and females receiving 19 mg/kg Compound 8 were comparable to the vehicle treated animals, indicating a slight reversal towards normalcy. Conversely, the cisplatin-treated animals continued to exhibit decreased body weights, which tended to become more severe during the recovery period, relative to the vehicle group.

Compound 8 treated animals were noted with decreased reticulocyte counts and increased monocyte counts and fibrinogen and globulin concentrations in both sexes at all dose levels. Platelet counts were also increased in males at 14 and 19 mg/kg. Changes attributable to altered renal function (increased creatinine concentration, urea nitrogen concentrations, phosphorus and calcium concentrations; increased urine volume with concomitant decreased urine specific gravity; increased glucosuria; and decreased urine pH and creatinine clearance) were noted in both sexes at all Compound 8 dose levels. Increased amylase and lipase activity and increased AST, ALT, and/or lactate dehydrogenase (LDH) activities, were also present in both sexes at all dose levels. Increased cholesterol and decreased triglycerides along with increased glucose values were also noted in Compound 8 treated animals. Decreased activated partial thromboplastin times (aPTT) in males at all Compound 8 dose levels and prolongations in prothrombin time in females at all Compound 8 dose levels were also noted.

Cisplatin-treated animals exhibited similar findings as those observed in the 19 mg/kg Compound 8-treated group, including decreased reticulocyte counts and platelets in both sexes administered cisplatin 6 mg/kg, although reticulocyte counts were decreased to a greater magnitude than the 19 mg/kg Compound 8 dose group, and moderately decreased total leukocyte counts in both sexes administered cisplatin 6 mg/kg. Changes attributable to altered renal function (increased creatinine concentration, urea nitrogen concentrations, phosphorus and calcium concentrations; increased urine volume with concomitant decreased urine specific gravity; increased glucosuria; and decreased urine pH and creatinine clearance) were noted in both sexes administered cisplatin 6 mg/kg, albeit at magnitudes generally greater than those observed in either sex at 19 mg/kg Compound 8. Increases in AST, LDH, and amylase activity were also noted in animals administered cisplatin at 6 mg/kg, although changes in these analytes were inconsistently noted among males and females, and occurred at lower magnitudes than those observed in either sex at 19 mg/kg Compound 8. Changes among clinical chemistry analytes that were unique to animals administered cisplatin 6 mg/kg included mild to moderate decreases in sodium, potassium, and/or chloride concentrations. A mild decrease in aPTT was also present at the terminal collection in males administered cisplatin at 6 mg/kg.

Organ weight changes in Compound 8 treated groups at ≥14 mg/kg included decreased absolute and relative thymus weights in males and females, decreased absolute and relative prostate gland weights in males, and decreased absolute and relative seminal vesicle with coagulating gland weights in males. Microscopic changes in Compound 8 treated groups included kidney tubular degeneration/necrosis and/or regeneration in terminal and recovery males at ≥9 mg/kg and in females at ≥14 mg/kg; decreased bone marrow hematopoietic cellularity in terminal and recovery males and females at ≥9 mg/kg; thymic lymphoid cortical depletion in terminal males and females at ≥14 mg/kg; subacute/chronic inflammation and/or hemorrhage at the last injection site in terminal males and females at 19 mg/kg; and sporadic bilateral or unilateral testicular seminiferous tubule degeneration/atrophy or seminiferous tubule dilation with or without epididymal oligospermia/germ cell debris in terminal and recovery males at ≥9 mg/kg. Also noted microscopically were erosion/ulceration of the nonglandular stomach of terminal males at 19 mg/kg; glandular stomach mucosal atrophy in terminal males and females at 19 mg/kg; skin alopecia/hypotrichosis in a few terminal males and females at 19 mg/kg; focal hepatic necrosis in the liver of a single terminal female at 19 mg/kg; individual hepatocellular necrosis in one terminal female at 19 mg/kg; and pancreatic acinar cell apoptosis in terminal males and females at ≥9 mg/kg Compound 8.

Organ weight changes in the cisplatin treated group included decreased absolute and relative thymus weights. Decreased absolute and relative organ weights were also noted in the spleen and thyroid/parathyroid glands of terminal males and females at 6 mg/kg (cisplatin) and liver, prostate, and seminal vesicle with coagulating gland of terminal males at 6 mg/kg (cisplatin). Microscopic changes noted in cisplatin-treated animals included kidney tubular degeneration/necrosis and/or regeneration which were generally of increased severity compared to 19 mg/kg Compound 8; decreased bone marrow hematopoietic cellularity which was of increased severity when compared to animals treated with Compound 8 at a dose of 19 mg/kg; and increased incidence/severity of thymic lymphoid cortical depletion which was of increased severity when compared to 19 mg/kg Compound 8 animals. Also noted in cisplatin-treated animals was lymphoid depletion of the spleen, which was not noted in Compound 8-treated animals. Increased incidence/severity of subacute/chronic inflammation and/or hemorrhage of the last injection site, and increased incidence of glandular stomach mucosal atrophy were all noted in cisplatin-treated animals at incidence and/or severity similar to the 19 mg/kg Compound 8-treated group. Testicular changes were noted in cisplatin-treated males at an increased incidence/severity than those findings noted in Compound 8-treated males.

Following the completion of the 3-week recovery period, findings noted in the Compound 8 treated groups generally tended to reverse towards normalcy, with the exception of noted changes in platelet counts, cholesterol concentration, urine pH, creatinine clearance, and testicular changes. Similar findings were noted in the cisplatin-treated group at the end of the 3-week recovery period.

Based on the adverse findings noted in the Compound 8 dose groups, the $STD_{10}$ (the dose that causes death or irreversible severe toxicity in 10% of the animals) was projected to be ≥19 mg/kg (114 mg/m$^2$).

Local Tolerance

Local tolerance of Compound 8 1 followed an IV administration to male and female rats was assessed in the repeat-dose GLP study (Compound 8-TX-007). The assessment was done by microscopic evaluation of the last injection site.

In the last injection site, slightly increased incidence and/or severity of perivascular subacute/chronic inflammation and/or hemorrhage were noted in terminal males and females at 19 mg/kg. Mixed inflammatory cells and/or extravasation of RBCs were observed surrounded vessels in the majority of animals across all groups; these types of findings are expected to some degree with the injection process. However, the slightly increased incidence and/or severity may reflect minimally increased irritation at 19 mg/kg.

Cisplatin-related microscopic findings at the last injection site were limited to slightly increased severity of inflammation in the terminal males and increased incidence of pancreatic apoptosis was only noted in terminal females.

Other Studies:

Genotoxicity studies, carcinognenicity studies, reproductive and developmental toxicity studies are also carried out with Compound 8. For example, the following studies are carried out: antigenicity, immunotoxicity, mechanistic studies, dependence, studies on metabolites, studies on impurities, fertility and early embryonic development, embryofetal development, prenatal and postnatal development, including maternal function, and studies in which offspring (juvenile animals) are dosed and/or further evaluated.

A summary of in vivo evaluation of Compound 8 and comparison with cisplatin is shown in Table 9 below.

TABLE 9

| in vivo Evaluation of Compound 8 and Comparison with Cisplatin ||| |
| --- | --- | --- |
| Evaluation | Compound 8, 19 mg/kg | Cisplatin. 6 mg/kg |
| Mortality | No unscheduled deaths | No unscheduled deaths |
| Clinical observations, FOB and ophthalmic observations | No adverse effects | Slight increase in the incidence of palpebral closure (post 1$^{st}$); increased thermal response time (post 2$^{nd}$ dose); and a slight decrease in mean forelimb grip strength at the end of recovery.* |
| Hemathology (moderate to marked changes) | Reticulocytes↓, (resolved at recovery), platelets↑ | Greater changes to Reticulocytes↓ Leucocytes↓* |
| Coagulation | Fibrinogen↑(fully resolved at recovery) | Fibrinogen↑ (in male group at recovery only |
| Clinical Chemistry (moderate to marked): | Creatinine↑, AST↑, ALT↑, Amylase↑, Lipase↑, Cholesterol↑ Globulin↑ (partially to fully resolved at recovery) | Urea nitrogen↑and Creatinine↑ (much greater increase) together with Cholesterol↑ decreased at recovery but remained elevated Sodium↑, Potassium↑, Chloride↑ resolved at recovery |
| Pathology ||| |
| Organ weights | Thymus↓ | Thymus↓ (greater), Liver↓, Spleen↓ |
| Kidneys (moderate or severe) | Tubule degeneration/necrosis (moderate in terminal, mild in recovery) and regeneration (moderate). Severity is dose dependent | Tubule degeneration/necrosis (moderate in terminal, mild in recovery) and regeneration (moderate). |
| Thymus | (1M), (moderate at terminal, none at recovery) | (10M/7F) (moderate in terminal, none at recovery) |

TABLE 9-continued in vivo Evaluation of Compound 8 and Comparison with Cisplatin

| Evaluation | Compound 8, 19 mg/kg | Cisplatin. 6 mg/kg |
| --- | --- | --- |
| Stomach nonglandular | erosion ulcer (1M), no findings at recovery* | |
| Stomach glandular | | erosion ulcer* (1M), no findings in the recovery group* |
| Testes | Degeneration/atrophy (1M) not dose dependent, no findings at recovery | |
| Epididymides: | Epididymides (bilateral): severe (1M at 9 mg/kg) not dose dependent, none at recovery | Epididymides (inilateral): severe (1M), none at recovery |
| Tissues with minimal to mild observations | bone marrow (femur and sternum), Last injection site, skin, spleen, pancreas recovery: | terminal: recovery: |

Example 5

In Vivo Pharmacology

Anti-tumor Activity in Murine Xenograft Models

The potential anti-tumor activity of Compound 8 has been evaluated in various murine xenograft models, including ovarian, pancreatic, and lung.

Ovarian Xenograft Model

The effect of Compound 8 on tumor growth inhibition (TGI) was evaluated in the A2780 human ovarian cancer nude mouse (female Crl:NU(NCr)-Foxn1$^{nu}$) xenograft model. In this model, a total of 6 doses of Compound 8 (20 mg/kg), cisplatin (4 mg/kg) as a comparator, and vehicle control treatments were administered IV on an every 3-day (q3) to end schedule, with percent tumor growth inhibition (% TGI) determined thereafter. Compound 8 and cisplatin treatment resulted in significant (p<0.0001) decreases in tumor growth relative to vehicle control (72% TGI and 55% TGI, respectively). Although the decrease in tumor growth for Compound 8 was greater than that for cisplatin, the difference between groups did not reach statistical significance (p=0.242) (Table 11).

TABLE 10

Percent Tumor Growth Inhibition with Compound 8 and Cisplatin versus Vehicle Control in the A2780 (Human Ovarian Cancer) Xenograft Model

| Treatment | Dose Level (mg/kg) | Dose Level (uM/kg) | MTV (mm³) | SEM (mm³) | TGI (%) | Statistical Significance versus Vehicle | Statistical Significance versus cisplatin |
| --- | --- | --- | --- | --- | --- | --- | --- |
| Vehicle | N/A | N/A | 2314 | 285 | N/A | N/A | N/A |
| Cisplatin | 4 | 13.3 | 1052 | 107 | 55 | *** | N/A |
| Compound 8 | 20 | 34.2 | 639 | 37 | 72 | *** | NS |

MTV = mean tumor volume; N/A = not applicable; NS = not significant; SEM = standard error of the mean; TGI = tumor growth inhibition.
*** p < 0.0001.

All groups experienced negligible mean BW losses; the mean maximal BW loss was 7.4% at Day 15 for Compound 8, 2.3% Day 5 for cisplatin, and 0.3% at Day 5 for vehicle. No treatment-related side effects were seen in any treatment group.

Pancreatic Xenograft Models

The effect of Compound 8 on TGI was evaluated in the BxPC-3 human pancreatic adenocarcinoma nude mouse (female Crl:NU(NCr)-Foxn1$^{nu}$) xenograft model. In this model, a total of 7 doses of Compound 8 (20 mg/kg), cisplatin (4 mg/kg) as a comparator, and vehicle control treatments were administered IV on a q3 to end schedule, with % TGI determined thereafter on Day 20. Compound 8 and cisplatin treatment each resulted in TGI of 31% relative to vehicle control in this model; the difference between each group and vehicle control was not significant.

All groups experienced negligible mean BW losses. Treatment-related side effects in the Compound 8 group included swollen tails on Day 13 in all animals, which became severe and ulcerated in 1 animal on Day 16. No treatment-related side effects were seen in the cisplatin or vehicle control group.

In another pancreatic xenograft model, the MIA Paca-2 human pancreatic adenocarcinoma nude mouse (female Crl:NU(NCr)-Foxn1$^{nu}$) model, a total of 7 doses of Compound 8 (10 mg/kg), oxaliplatin (7 mg/kg) as a comparator, and vehicle control were administered IV on a q3 to end schedule, with TGI determined thereafter on Day 18. Treatment of MIA Paca-2 xenograft tumors with both oxaliplatin and Compound 8 led to statistically significant TGI relative to vehicle control of 61% (p=0.0023) and 64% (p=0.0014), respectively. Compound 8 and oxaliplatin were not significantly different from each other in this analysis (Table 11).

TABLE 11

Percent Tumor Growth Inhibition with Compound 8 and Oxaliplatin versus Vehicle Control in the MIA Paca-2 (Pancreatic) Xenograft Model

| Treatment | Dose Level (mg/kg) | Dose Level (uM/kg) | MTV (mm³) | SEM (mm³) | TGI (%) | Statistical Significance versus Vehicle | Statistical Significance versus Oxaliplatin |
|---|---|---|---|---|---|---|---|
| Vehicle | N/A | N/A | 3191 | 285 | N/A | N/A | N/A |
| Oxaliplatin | 7 | 17.9 | 1251 | 107 | 61 | ** | N/A |
| Compound 8 | 10 | 17.1 | 1150 | 37 | 64 | ** | NS |

MTV = mean tumor volume; N/A = not applicable; NS = not significant; SEM = standard error of the mean; TGI = tumor growth inhibition.
** p < 0.0025.

Negligible mean BW losses were seen in each group, with mean maximal BW loss of 3.7% at Day 18 for Compound 8, 8.1% Day 5.3 of oxaliplatin, and 0% for vehicle control. No treatment-related adverse effects were seen with Compound 8 or vehicle control. Treatment-related effects in the oxaliplatin group were seen, with all animals in the group being pale and dehydrated and having petechiae on Day 18.

Lung Xenograft Models

The effect of Compound 8 was evaluated in the Calu-6 human NSCLC nude mouse (female Crl:NU(NCr)-Foxn1$^{nu}$) xenograft model. In this model, a total of 4 doses of Compound 8 (10 mg/kg and 15 mg/kg), cisplatin (3 mg/kg) as a comparator, and vehicle control were administered IV twice weekly for 2 weeks, with TGI and percent tumor growth delay (% TGD) determined thereafter on Day 33 and Day 54, respectively. Significant TGI relative to vehicle control of 81% and 74% was seen with Compound 8 15 mg/kg and cisplatin, respectively (p<0.0001); the difference between Compound 8 and cisplatin was not significant. Percent TGI of 42% was seen with the lower Compound 8 dose of 10 mg/kg, which was significantly different from both vehicle (p=0.021) and Compound 8 15 mg/kg (p=0.03) but not significantly different from cisplatin (Table 12).

TABLE 12

Percent Tumor Growth Inhibition with Compound 8 and Cisplatin versus Vehicle Control in the Calu-6 (Human Non-small Cell Lung Cancer) Xenograft Model

| Treatment | Dose Level (mg/kg) | Dose Level (uM/kg) | MTV (mm³) | SEM (mm³) | TGI (%) | Statistical Significance versus Vehicle | Statistical Significance versus Cisplatin |
|---|---|---|---|---|---|---|---|
| Vehicle | N/A | N/A | 1791 | 259 | N/A | N/A | *** |
| Cisplatin | 3 | 10 | 462 | 65 | 74 | *** | N/A |
| Compound 8 | 15 | 25.7 | 335 | 36 | 81 | *** | NS |
| Compound 8 | 10 | 17.1 | 1045 | 216 | 42 | *** | NS |

MTV = mean tumor volume; N/A = not applicable; NS = not significant; SEM = standard error of the mean; TGI = tumor growth inhibition.
** p < 0.0001;
* p < 0.05.

Tumor growth delay relative to vehicle control of 18%, 51%, and 47% was seen with Compound 8 10 mg/kg, Compound 8 15 mg/kg, and cisplatin, respectively. At the higher Compound 8 dose level, TGD was significant relative to vehicle control (p<0.01), but not statistically different from cisplatin (p ≥0.05) (Table 13).

TABLE 13

Tumor Growth Delay with Compound 8 and Cisplatin versus Vehicle Control in the Calu-6 (Human Non-small Cell Lung Cancer) Xenograft Model

| Treatment Group | Dose Level (mg/kg) | Dose Level (uM/kg) | Median TTE (Days) | T-C (Days) | % TGD | Statistical Significance versus Vehicle | Statistical Significance versus Cisplatin |
|---|---|---|---|---|---|---|---|
| Vehicle | N/A | N/A | 35.8 | N/A | N/A | N/A | N/A |
| Cisplatin | 3 | 10 | 52.5 | 16.7 | 47 | * | N/A |
| Compound 8 | 15 | 25.7 | 42.3 | 6.5 | 18 | NS | NS |
| Compound 8 | 10 | 17.1 | 53.9 | 18.1 | 51 | ** | NS |

% TGD = percent tumor growth delay; N/A = not applicable; NS = not significant; T-C = XX; TTE = time to endpoint
* p < 0.05;
* p < 0.01.

Negligible mean BW losses were seen in each group, with mean maximal BW loss of 0.9% at Day 4 for Compound 8 10 mg/kg and 3.2% on Day 5 for Compound 8 15 mg/kg dose; no BW loss was seen in the cisplatin and vehicle control groups. No treatment-related side effects were seen with Compound 8 or vehicle control. One animal in the cisplatin group experienced severe petechiae on Day 4.

The effect of Compound 8 also was evaluated in the NCI-H520 human NSCLC nude mouse (female CrTac:NCr-Foxn1$^{nu}$) xenograft model. In this model, a total of 5 repeat dosing of Compound 8 (15 mg/kg, 10 mg/kg), cisplatin (3 mg/kg) as a comparator, and vehicle control, were administered IV twice weekly, with TGI determined thereafter on Day 31. Percent TGI of 56%, 83%, and 60% relative to vehicle was seen with Compound 8 10 mg/kg, Compound 8 15 mg/kg, and cisplatin, respectively. All treatments were statistically significant compared to vehicle (p<0.0001). The difference between either Compound 8 group and cisplatin was not significant (Table 14).

TABLE 14

Percent Tumor Growth Inhibition with Compound 8 and Cisplatin versus Vehicle Control in the NCI-H520 (Human Non-small Cell Lung Cancer) Xenograft Model

| Treatment | Dose Level (mg/kg) | Dose Level (uM/kg) | MTV (mm$^3$) | SEM (mm$^3$) | TGI (%) | Statistical Significance compared to Vehicle |
|---|---|---|---|---|---|---|
| Vehicle | N/A | N/A | 2041 | 291 | N/A | N/A |
| Cisplatin | 3 | 10 | 823 | 92 | 60 | *** |
| Compound 8 | 10 | 17.1 | 891 | 102 | 56 | ***, vs. cisplatin (NS) |
| Compound 8 | 15 | 25.7 | 353 | 34 | 83 | ***, vs. cisplatin (NS) |

MTV = mean tumor volume; N/A = not applicable; NS = not significant; SEM = standard error of the mean; TGI = tumor growth inhibition.
*** p < 0.0001.

All groups experienced negligible mean BW losses, with mean maximal BW losses of 11% at Day 17 for Compound 8 15 mg/kg, 2.7% at Day 4 for Compound 8 10 mg/kg, 0.43% on Day 4 for cisplatin, and 0.42% at Day 4 for vehicle control. No treatment-related adverse effects were seen in any treatment group.

Safety Pharmacology
Cardiovascular and Respiratory Systems

An in vitro evaluation of the binding of Compound 8 to membrane preparations of hERG using a radiolabeled antagonist was performed. In this assay, Compound 8 was tested when conjugated to human serum albumin and when un-conjugated to human serum albumin at concentrations of 3 μM and 10 μM, respectively. Findings revealed no evidence for significant cardiovascular toxicity with Compound 8 at concentrations of 3 uM conjugated to human serum albumin and or of 10 uM unconjugated to human serum albumin.

The cardiovascular and respiratory effects of Compound 8 administered IV were evaluated in Beagle dogs (Compound 8-TX-005). Findings showed that Compound 8, administered as a single IV injection to female Beagle dogs at doses of 6 and 10 mg/kg, did not produce mortality or changes in body temperature, heart rate, electrocardiogram (ECG) parameters (PR, RR, QRS, QT, or QTc intervals), or respiratory rate. Test article-related effects included observations of vomitus, which were noted for all animals at the end of the cardiovascular monitoring period (approximately 24 hours post-dose), and slight, non-dose-dependent increases in blood pressure (≤9-16% above controls) which were noted between 6 and 12 hours following both treatments.

In summary, IV administration of Compound 8 produced no observable adverse effects on cardiovascular or pulmonary function in female Beagle dogs at doses up to and including 10 mg/kg, corresponding to up to a 200 mg/m$^2$ HED. The assessment of the respiratory function showed that there were no test article related changes in the respiratory rate noted over the course of the study following IV administration of Compound 8 in female Beagle dogs at doses up to and including 10 mg/kg.

Pharmacokinetics and Drug Metabolism in Animals

A series of nonclinical studies have been performed to evaluate the PK properties of Compound 8, including the assessment of in vitro protein binding in rat and human plasma; the PK of platinum in plasma and plasma ultrafiltrate after IV administration of Compound 8 in the mouse, rat, and dog, and RBC partitioning of platinum from Compound 8 in vitro and in vivo. Furthermore, relative platinum levels in tumor in plasma for Compound 8 and cisplatin were measured in a mouse xenograft study. Lastly, Compound 8 and form Compound 8 conjugated to albumin were tested for CYP inhibition.

Absorption

Compound 8 is administered IV; therefore, absorption may not be relevant.

Distribution
Tissue Distribution

No formal tissue distribution studies have been performed with Compound 8.

In Vitro Plasma Protein Binding

In an in vitro protein binding assay using rat and human plasma (Compound 8-DMPK-008), Compound 8 was shown to be very highly protein bound (≥99%) after incubation for 10 minutes at 37° C. These results are consistent with the design of Compound 8 to rapidly and efficiently bind to albumin.

Total Plasma and Plasma Ultrafiltrate Platinum Pharmacokinetics in Mouse, Rat and Dog Nonclinical studies were performed to evaluate the PK of platinum in plasma after IV administration of Compound 8 in the mouse, rat, and dog. The analyses included platinum levels both in total plasma as well as plasma ultrafiltrate. In all species evaluated, Compound 8 showed that a significant majority of the platinum was bound to plasma proteins rather than found free in the ultrafiltrate.

In the mouse (Compound 8-DMPK-011; Compound 8-DMPK-012), administration of a single IV bolus dose of Compound 8 resulted in a total platinum plasma maximum concentration ($C_{max}$) of 282 µmoles/L at 5 minutes postdose. The area under the plasma concentration time curve (AUC) was 3680 h·µmol/L, and the half-life in the elimination phase was 23.2 hours. The plasma free platinum $C_{max}$ was 15.9 moles/L and the AUC was 20.6 h·µmol/L. The half-life in the elimination phase was 7.27 hours.

The half-life of total plasma platinum is similar to the half-life of albumin in the mouse, consistent with fact that Compound 8 forms a covalent attachment to albumin in vivo. These data also show that unbound platinum in plasma ultrafiltrate is only a small fraction of total circulating platinum. At $C_{max}$, ultrafiltrate platinum to total ratio was 0.06 and the ultrafiltrate to total AUC ratio was 0.0056, demonstrating only a small (<1%) portion of platinum in circulation is free in the ultrafiltrate.

Compound 8 was administered in 2 different formulations in mice. The formulation used in pharmacology studies was 5% dimethyl sulfoxide (DMSO)/10% Solutol/Saline, and the formulation used in PK studies was 5 mM citrate pH about 4; this latter formulation is that used in GLP toxicology studies in the rat and is the human clinical formulation. The $AUC_{(0-48h)}$ values for total plasma were 3440 µM·hr for the DMSO/Solutol formulation and 3270 µM·hr for the citrate formulation. The mean difference for these 2 values is 5%, indicating that there is a negligible difference in PK observed between the 2 different formulations used in mouse studies, and therefore, that there is little or no effect of formulation on assay results.

A summary of total plasma platinum PK parameters in the rat and dog is presented in Table 15.

TABLE 15

Total Plasma Platinum PK Parameters in the Rat and Dog

| | Rat | | | |
| --- | --- | --- | --- | --- |
| | Compound 8 | | | Cisplatin |
| Parameter | 9 mg/kg | 14 mg/kg | 19 mg/kg | 6 mg/kg |
| $AUC_{inf}$ (h · µmol/L) | 3824 | 5917 | 7744 | 382 |
| CL (mL/kg/min) | 0.0671 | 0.0675 | 0.0700 | 0.873 |
| $t_{1/2}$ (hours) | 51.4 | 53.8 | 53.8 | 102 |
| $C_{max}$ (µmol/L) | 301 | 369 | 393 | 50 |
| Vz (mL/kg) | 299 | 314 | 326 | 7747 |
| Vss (mL/kg) | 184 | 208 | 224 | 6340 |

| | Dog | | | |
| --- | --- | --- | --- | --- |
| | Compound 8 | | | |
| Parameter | 3 mg/kg | 6 mg/kg | 10 mg/kg | 12 mg/kg |
| $AUC_{inf}$ (h · µmol/L) | 2820 | 6180 | 10090 | 12550 |
| CL (mL/kg/min) | 0.0305 | 0.0277 | 0.0282 | 0.0273 |
| $t_{1/2}$ (hours) | 116 | 118 | 109 | 105 |
| $C_{max}$ (µmol/L) | 49 | 104 | 157 | 197 |
| Vz (mL/kg) | 304 | 279 | 267 | 247 |
| Vss (mL/kg) | — | — | — | — |

AUC = area under the plasma concentration curve extrapolated to infinity;
CL = clearance;
$C_{max}$ = maximum plasma concentration;
$t_{1/2}$ = half-life;
$V_{ss}$; apparent volume of distribution at steady state;
Vz = volume of distribution In both rats treated with an Compound 8 IV bolus dose of 9, 14, or 19 mg/kg (Compound 8-TX-007), and dogs treated with an Compound 8 IV bolus dose of 3, 6, 10, or 12 mg/kg (Compound 8-TX-002), exposure of total platinum was dose-linear over the range studied. The clearance of total platinum was very low in both rat (0.07 mL/min/kg) and dog (0.03 mL/min/kg), with a low volume of distribution (Vz) in both species, consistent with restriction of the platinum significantly to the plasma compartment. The elimination half-lives were long in rat (53 hours) and dog (109 hours), consistent with the albumin half-lives in these species.

The rat and dog ultrafiltrate levels dropped rapidly in the distribution phase, with a long elimination phase half-life in parallel with the total platinum. The ultrafiltrate levels were approximately 1% of the total platinum levels throughout the distribution phase.

Compound 8 behaves consistently with the constraint of conjugation to albumin, and restriction to the albumin area of distribution. This prevents Compound 8 platinum from distributing to the entire water area of distribution until the platinum is released from the conjugate. Since the extracellular fluid is 300 mL/kg and the plasma is 40 mL/kg, the average Vz of 326 mL/kg reflects the distribution to the plasma and extracellular space as that is expected of an albumin conjugaterence in their entirety. In contrast, the Vz of cisplatin is very high, and reflects a greater propensity to distribute broadly.

Red Blood Cell Partitioning In Vitro

An analysis of RBC partitioning of Compound 8 was conducted in vitro in human and rat whole blood (Compound 8-DMPK-009). In human blood, the majority of the platinum (92%) was observed in plasma at all timepoints tested and low levels (<8%) were observed in RBCs throughout the 4 hours. Similar partitioning was seen in rat RBCs at the earliest time points, with a moderately increased accumulation in RBCs to 4 hours, with 18% observed at that time point. These data show that the majority of platinum from Compound 8 introduced into whole blood remains associated with the plasma with a fraction of the platinum being detected within RBCs. The levels of platinum associated with the RBCs did not change over time in human whole blood and increases moderately over 4 hours in rat whole blood (Table 16).

TABLE 16

Percent Compound 8 in Human and Rat Whole Blood Partitions

| | Human | | | | Rat | | | |
| --- | --- | --- | --- | --- | --- | --- | --- | --- |
| Parameter | 0.5 (h) | 1 (h) | 2 (h) | 4 (h) | 0.5 (h) | 1 (h) | 2 (h) | 4 (h) |
| Plasma | 92.1 | 92.8 | 92.8 | 92.0 | 90 | 88 | 86 | 82 |
| RSD | 0.64 | 0.59 | 0.41 | 1.23 | 0.7 | 1.6 | 2.0 | 2.5 |
| Red Blood Cells | 7.90 | 7.20 | 7.10 | 7.40 | 10 | 12 | 14 | 18 |
| RSD | 7.90 | 7.21 | 7.16 | 8.00 | 6.7 | 12 | 13 | 11 |

RSD = relative standard deviation

Red Blood Cell Platinum Concentrations

RBC platinum concentrations were assessed in the repeat-dose toxicology study in rats (Compound 8-TX-007). Administration of cisplatin (6 mg/kg) resulted in accumulation of platinum in the RBCs at 96 hours post-dose on Day 21 relative to Day 1, whereas Compound 8 (19 mg/kg) did not result in significant accumulation of platinum in the RBCs on Day 21 relative to Day 1, implying that less Compound 8 platinum drug delivery is lost to RBCs.

Tumor Exposure

Figure 13:
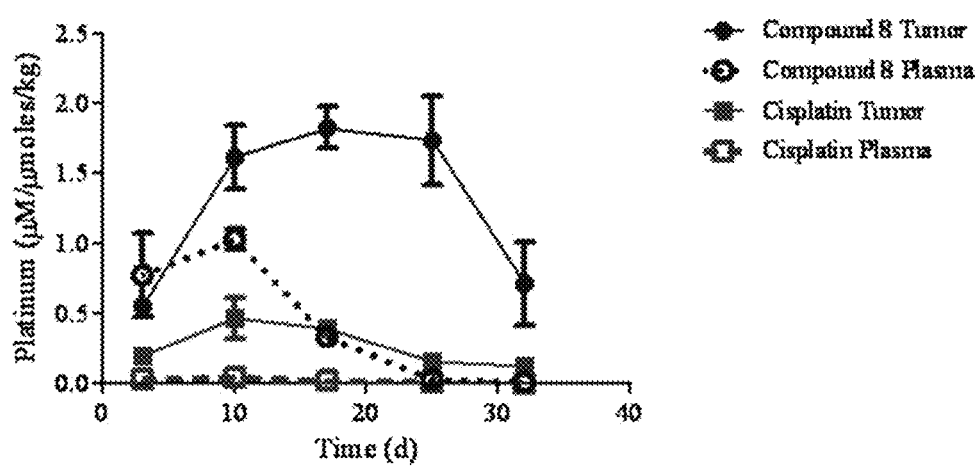
FIG. 13 shows platinum levels in tumor and plasma after Compound 8 (BTP-114, 15 mg/kg) and cisplatin (3 mg/kg) administration.

The relative platinum levels in tumor and plasma after administration of Compound 8 (10 and 15 mg/kg) and cisplatin (6 mg/kg) on Days 0, 3, 7, and 10 were measured in the NCI-H520 human NSCLC nude mouse (female CrTac:NCr-Foxn1$^{nu}$) xenograft model (Compound 8-DMPK-013). On a molar platinum basis, Compound 8 at MTD was dosed 30% higher than cisplatin, but the tumor platinum AUC was 12.8 times higher and the plasma platinum exposure 64 times higher (FIG. 13). These differences demonstrate the significant increase in plasma and tumor exposure achieved utilizing Compound 8, a prodrug of cisplatin that covalently attaches to albumin.

Metabolism

Microsomal stability could not be performed because negative controls failed. In stability studies, Compound 8 was below the limit of quantitation in NADPH-free controls (Compound 8-DMPK-011). This is consistent with literature reports that microsomes contain protein thiols (Liebler D C, Meredith M J, Guengerich F P. Formation of glutathione conjugates by reactive metabolites of vinylidene chloride in microsomes and isolated hepatocytes. Cancer Res 1985; 45(1): 186-93, the contents of which are incorporated herein by reference in their entirety), would react with Compound 8. CYP inhibition was studied to determine whether Compound 8 has an inhibitory effect on microsomes.

Excretion

No excretion studies have been performed with Compound 8.

Drug-Drug Interactions

It was known that Compound 8 disappeared quickly in microsome preparations in the absence of NADPH, which is consistent with literature that suggests high protein thiol content in the microsome (Liebler D C, Meredith M J, Guengerich F P. Formation of glutathione conjugates by reactive metabolites of vinylidene chloride in microsomes and isolated hepatocytes. Cancer Res 1985; 45(1):186-93, the contents of which are incorporated herein by reference in their entirety), which would react with Compound 8. It was also widely established in the literature that maleimides quickly conjugate albumin (Kratz F. Albumin as a drug carrier: design of prodrugs, drug conjugates and nanoparticles. J Control Release. 2008; 132(3):171-83, the contents of which are incorporated herein by reference in their entirety). Therefore, both Compound 8 and Compound 8 conjugated to albumin in vitro (Compound 8S) were evaluated in a CYP inhibition study; results are summarized in Table 17.

TABLE 17

CYP Inhibition Results for Compound 8 and Compound 8S (Preconjugated Compound 8)

| Compound | IC$_{50}$ (µM) | | | | | | |
|---|---|---|---|---|---|---|---|
|  | 1A2 | 2B6 | 2C8 | 2C9 | 2C19 | 2D6 | 3A4 |
| Compound 8 | 0.55 | 0.582 | 0.68 | 0.95 | 2.72 | 0.72 | 1.96 |
| Compound 8 Albumin conjugate | 4.87 | 0.07 | 6.13 | 1.44 | >6.0 | >6.0 | >6.0 |

Compound 8 showed a moderate level of activity across a range of CYPs tested. Since Compound 8 reacts rapidly with albumin in circulation the inhibition of CYPs, this is not considered to be a concern. The preconjugate preparation showed less activity against the panel of CYPs, with the exception of CYP2B6. Given this observation, drugs that are metabolized principally by CYP2B6 are prohibited in Compound 8 clinical studies.

Example 6

Effects in Humans

Compound 8 is a cisplatin pro-drug. There is an extensive body of published literature of the clinical evaluation of platinum compounds. Clinical testing of cisplatin began in 1971 (Lebwohl D, Canetta R. Clinical development of platinum complexes in cancer therapy: an historical perspective and an update. Eur J Cancer 1998; 34(10):1522-34, the contents of which are incorporated herein by reference in their entirety), and the compound was initially approved by the FDA for the treatment of metastatic testicular and ovarian cancers in 1978 and subsequently approved for the treatment of advanced bladder cancer.

Cisplatin is currently available as a generic drug in the United States, making the tracking of sales and use difficult. However, as reported by Miller et al. (Miller R P, Tadagavadi R K, Ramesh G, Reeves W B. Mechanisms of Cisplatin nephrotoxicity. Toxins (Basel). 2010; 2(11):2490-518, the contents of which are incorporated herein by reference in their entirety), a search of the ClinicalTrials.gov database returned ≥500 active clinical studies involving cisplatin, an indication of its ongoing wide clinical use.

Cisplatin is used as first-line chemotherapy against epithelial malignancies of lung, ovarian, bladder, testicular, breast, head and neck, oesophageal, gastric and pancreatic but also as second- and third-line treatment against a number of metastatic malignancies including cancers of the melanoma, prostate, mesothelioma, leiomyosarcomas, malignant gliomas, and others. Cisplatin is considered the gold standard treatment against cervical cancer in combination with radiotherapy (Pasetto L M, D'Andrea M R, Brandes A A, Rossi E, Monfardini S. The development of platinum compounds and their possible combination. Crit Rev Oncol Hematol. 2006; 60(1):59-75, the contents of which are incorporated herein by reference in their entirety).

In most advanced cancers, the response rate to cisplatin is ~50% in the first-line setting and 15% in the second- or third-line setting. Response rates of 25 to 50% have been observed for chemo-naive patients with advanced NSCLC treated with cisplatin or carboplatin in combination with gemcitabine or taxanes and in exceptional cases, these rates are up to 80% with addition of radiotherapy (Pasetto L M, D'Andrea M R, Brandes A A, Rossi E, Monfardini S. The development of platinum compounds and their possible combination. Crit Rev Oncol Hematol. 2006; 60(1):59-75, the contents of which are incorporated herein by reference in their entirety).

The starting dose projected in humans using allometry is the dose that will result in $\frac{1}{10}^{th}$ the AUC observed in rats at STD$_{10}$ in the GLP repeat dose toxicity study (Compound 8-TX-007). The rat STD$_{10}$ in Compound 8-TX-007 was 19 mg/kg. The observed AUC at 19 mg/kg in rats was 7,060 uM·hr; thus, $\frac{1}{10}^{th}$ the AUC is 706 uM·hr. Using the Dose=AUC×CL relationship, the proposed starting dose in humans is 20 mg/m$^2$ (Table 18).

TABLE 18

Projected and Measured PK Parameter Overview

| Parameter | Mouse | Rat | Dog | Human MTD | Human Efficacy AUC and Dose | Human Safe Starting AUC and Dose |
|---|---|---|---|---|---|---|
| Projected vs. Measured | | Measured | | Projected | Projected | Projected |
| $t_{1/2}$ (h) | 23.2 | 53.8 | 109 | 450** | 450** | 450** |
| Dose (mg/m$^2$) | 41.8 (MTD) | 120 (MTD*) | 205 (MTD) | 383 | 98 | 20 |
| MTD AUC ($\mu M \cdot h$) | 3,680 | 7,060 | 10,100 | 14,422 | 3,680 | 706 |

*STD$_{10}$ was 19 mg/kg not achieved with statistical significance in Study Compound 8-TX-001, so the more conservative MTD closest-dose was used to assess safe starting dose exposure.
**Literature value for albumin.

The allometric scaling predicts a low clearance and long half-life of total platinum in humans with an efficacious dose of 98 mg/m$^2$ and an MTD of 383 mg/m$^2$, based on PK and pharmacology in preclinical species (Table 19).

TABLE 19

Comparative Pharmacokinetic Data and Systemic Exposure to Compound 8 (5 mM Citrate Formulation) after IV Administration to Mice, Rats, Dogs, and Humans

| Species | Dose (mg/kg/day) | Dose (mg/m$^2$/day) | AUC ($\mu M \cdot hr$) | References |
|---|---|---|---|---|
| Mouse | 15 | 41.8 | 3,680 | Compound 8-DMPK-012 |
| Rat | 19 | 120 | 7,060 | Compound 8-DMPK-002 |
| Dog | 10 | 205 | 10,000 | Compound 8-DMPK-003 |
| Humans: | | | | |
| Projected Safe Starting Dose and Exposure | 0.5 | 20 | 706 | Compound 8-DMPK-016 |
| Projected Efficacious Dose and Exposure | 2.44 | 98 | 3,680 | Compound 8-DMPK-016 |
| Projected MTD and Exposure | 9.58 | 383 | 14,400 | Compound 8-DMPK-016 |

Potential Risks

Nonclinical data with Compound 8 support safe dosing in humans. The following subsections describe potential risks with Compound 8 in the clinical setting, based on nonclinical data with Compound 8 and clinical data with other platinum compounds in the oncologic setting.

Nausea and Vomiting

Cisplatin is associated with nausea and vomiting.

Vomiting was observed in nonclinical studies with Compound 8. Patients participating in clinical studies of Compound 8 may receive prophylactic 5-HT$_3$ receptor antagonist-based anti-emetic treatment before each Compound 8 dose, per standard institutional practice.

Nephrotoxicity

Cisplatin is associated with dose-related and cumulative renal insufficiency, including acute renal failure.

Based on nonclinical study findings, a reduced risk of renal toxicity relative to cisplatin is anticipated with Compound 8. In the rat, a single IV administration of Compound 8 at doses up to 20 mg/kg resulted in mild to minimal kidney necrosis at the highest dose evaluated; whereas treatment with a single dose of cisplatin 7 mg/kg resulted in a high incidence of moderate acute tubular necrosis of the kidney. Furthermore, clinical chemistry findings revealed a lesser effect on urea nitrogen and creatinine with Compound 8 compared to cisplatin, indicating reduced kidney toxicity. These findings were supported by the results of the GLP repeat-dose toxicity study in the rat, which also indicated reduced kidney toxicity with Compound 8 relative to cisplatin.

In order to reduce the risk of nephrotoxicity, patients participating in clinical studies of Compound 8 are required to have normal serum creatinine or calculated creatinine clearance ≥60 mL/min (Cockroft-Gault formula). Furthermore, patients are required to receive IV hydration before and after each Compound 8 dose, as described in the clinical study protocol. Diuretic therapy with mannitol or furosemide is not required, but may be administered per institutional practice.

Patients participating in clinical studies of Compound 8 will have clinical chemistry and urinalysis performed before each Compound 8 dose, and patients with signs of nephrotoxicity are to be managed as described in the clinical study protocol.

Ototoxicity

Cisplatin is associated with ototoxicity manifested by subjective hearing loss, ear pain, and/or tinnitus.

Patients participating in clinical studies of Compound 8 are to be monitored for signs of ototoxicity and managed as described in the clinical study protocol.

Neurotoxicity

Cisplatin is associated with sensory neuropathy, characterized by symptoms of distal paresthesias and numbness.

In the repeat dose toxicity study in the rat, no effects of Compound 8 at doses up to 19 mg/kg were seen on FOB assessments and no other signs of neurotoxicity were noted.

Patients with pre-existing ≥Grade 2 peripheral neuropathy are prohibited from participating in clinical studies of Compound 8. Furthermore, patients participating in clinical studies of Compound 8 will be monitored for signs of sensory neuropathy and managed as described in the clinical study protocol.

Myelosuppression

Cisplatin is associated with myelosuppression (i.e., leukopenia and thrombocytopenia) in 25 to 30% of patients treated.

In nonclinical studies, Compound 8 was associated with hematologic abnormalities in both rats and dogs, including decreases in reticulocytes, red cell mass, neutrophils, and platelets.

Patients are required to have adequate bone marrow function to be eligible for participation in Compound 8 clinical studies. Patients participating in Compound 8 clinical studies will have hematologic tests performed before each Compound 8 dose, and patients with hematologic toxicities are to be managed as described in the clinical study protocol.

Hypersensitivity Reactions

Cisplatin is associated with hypersensitivity reactions, occurring in up to 20% of patients treated.

No signs suggestive of an allergic reaction to Compound 8 were seen in nonclinical studies. However, as a precaution, facilities for the management of anaphylaxis must be available during Compound 8 infusion. Epinephrine (1:1000) for injection, resuscitation equipment, and personnel competent in their use should be immediately available. Patients should be monitored carefully for any such symptoms so treatment can begin immediately if they occur.

Potential Drug Interactions

Compound 8 and a pre-conjugated form of Compound 8 attached to albumin were tested for inhibition of CYPs. For the pro-conjugated form of Compound 8, weak CYP inhibition was noted, with the exception of CYP2B6, with an $IC_{50}$ of 0.070 uM. Because of this finding, concomitant use of medications cleared by CYP2B6 (e.g., rifampin) is prohibited in clinical studies of Compound 8.

Carcinogenesis, Mutagenesis, and Impairment of Fertility

Nonclinical studies have not been performed to test Compound 8 for its carcinogenic potential or potential to impair fertility.

In a nonclinical carcinogenicity study of cisplatin, 13 deaths secondary to malignancy were seen in 50 rats treated with cisplatin for 3 weeks, 3×1 mg/kg body weight/week. Furthermore, the development of secondary malignancies has been reported in patients treated with cisplatin (Cisplatin prescribing information).

Pregnancy

Animal reproduction studies have not been performed with Compound 8. It is not known whether Compound 8 can cause fetal harm when administered to a pregnant woman or can affect reproductive capacity.

Cisplatin can cause fetal harm when administered to pregnant women. Compound 8 must not be administered to pregnant women. Females of childbearing potential as well as fertile men and their partners participating in clinical studies of Compound 8 must agree to abstain from sexual intercourse or use adequate contraception, as defined in the clinical study protocol, from 30 days before the first through 30 days after the last Compound 8 dose.

Nursing Mothers

It is not known whether Compound 8 is excreted in human milk. Compound 8 should not be given to nursing mothers.

Management of Potential Toxicity and Overdose

Cisplatin doses ≥100 mg/m²/cycle once every 3 to 4 weeks are rarely used in the clinical setting. Cases of cisplatin overdose, which have been fatal in some cases, have been reported in the literature (Charlier C, Kintz P, Dubois N, Plomteux G. Fatal overdosage with cisplatin. J Anal Toxicol 2004; 28(2):138-40; Hofmann G, Bauernhofer T, Krippl P, Lang-Loidolt D, Horn S, Goessler W, et al. Plasmapheresis reverses all side-effects of a cisplatin overdose—a case report and treatment recommendation. BMC Cancer 2006 Jan. 4; 6: 1; Yamada Y, Ikuta Y, Nosaka K, Miyanari N, Hayashi N, Mitsuya H, Baba H. Successful treatment of Cisplatin overdose with plasma exchange. Case Rep Med 2010; 2010:802312; Jurek T, Rorat M, Dys P, Swiatek B. Fatal cisplatin overdose in the treatment of mediastinal lymphoma with the ESHAP regimen—analysis of the causes of the adverse drug event. Onkologie 2013; 36(1-2):49-52, the contents of each of which are incorporated herein by reference in their entirety).

Ototoxicity was reported as the presenting symptom in several cases of cisplatin overdose. Other toxicities reported to be associated with cisplatin overdose include nausea and vomiting, renal insufficiency, electrolyte abnormalities, myelosuppression, peripheral neuropathy, hepatotoxicity, and retinopathy. Diarrhea, pancreatitis, seizures, and respiratory failure have also been reported (Tsang R Y, Al-Fayea T, Au H J. Cisplatin overdose: toxicities and management. Drug Saf 2009; 32(12): 1109-22, the contents of which are incorporated herein by reference in their entirety).

No specific antidote for cisplatin exists. Key management principles and strategies to lessen toxicities include reno-protection and enhancing drug elimination with aggressive IV hydration with or without the use of an osmotic diuretic, and avoidance of nephrotoxic medications. Sodium thiosulfate and plasmapheresis, with or without hemodialysis support, should be strongly considered (Tsang et al., 2009, the contents of which are incorporated herein by reference in their entirety). Such treatment was reported as successful in a patient inadvertently treated with cisplatin 80 mg/m² daily for 3 days (240 mg/m² total dose) (Yamada et al., 2010, the contents of which are incorporated herein by reference in their entirety). Close monitoring of clinical and laboratory parameters, and institution of supportive therapies, including antiemetics and hematopoietic colony stimulating factor support, are warranted (Tsang et al., 2009, the contents of which are incorporated herein by reference in their entirety).

Measures similar to those described above for the management of cisplatin overdose should be initiated in the setting of a Compound 8 overdose.

Storage

Compound 8 Powder for Injection is to be stored frozen at ≤−20° C., protected from light. Compound 8 is to be stored in a locked area, accessible only to appropriate study personnel.

Example 7

Protocol of a Phase 1, Open-Label, Dose Escalation Study of Intravenous Administration of Single Agent Compound 8 in Patients with Advanced Solid Tumors, Followed by Expansion in Patients with BRCA Mutation-Positive Solid Tumors Compound 8 is a small molecule prodrug of cisplatin that is designed to covalently attach to albumin, thereby increasing serum half-life, and consequently area under the plasma concentration time curve (AUC), relative to cisplatin. This is postulated to result in increased accumulation of the prodrug and active drug in tumor tissue, and increase efficacy when compared to cisplatin, but without the associated toxicity. This premise is supported by nonclinical study findings, which have shown Compound 8 to bind efficiently to albumin in plasma in vitro and in vivo. In tumor xenograft models, Compound 8 has showed enhanced anti-tumor activity relative to cisplatin, as indicated by higher percent tumor growth inhibition. When administered as an IV bolus in rats and dogs, Compound 8 had an increased plasma AUC and extended half-life compared with cisplatin. Furthermore, based on nonclinical study findings, Compound 8 is anticipated to have an improved safety profile relative to cisplatin. Based on these findings, clinical investigation of Compound 8 is warranted.

The patients enrolled in the dose-escalation phase represent a population for whom no curative therapy exists. It has been recently shown that cancers characterized by deficient DNA repair pathways may be more sensitive to treatment with platinum, thus identifying a potential patient selection strategy. Defective DNA repair is well characterized in ovarian and breast cancers that harbor mutations in BRCA1/BRCA2 (Waddell N, Pajic M, Patch A M, Chang D K, Kassahn K S, Bailey P, et al. Whole genomes redefine the mutational landscape of pancreatic cancer. Nature. 2015; 518 (7540):495-501, the contents of which are incorporated herein by reference in their entirety). More recently, these deficiencies have been described in other advanced malignancies, including pancreatic and prostate cancers. Preliminary evidence suggests that these DNA repair-deficient subgroups of pancreatic, prostate (Vaishampayan U N, Fontana J, Heilbrun L K, Smith D, Heath E, Dickow B, Figg W D, the contents of each of which are incorporated herein by reference in their entirety). Phase II trial of bevacizumab and satraplatin in docetaxel-pretreated metastatic castrate-resistant prostate cancer. (Urol Oncol. 2014; 32(1):31.e25-33), and breast cancers (Isakoff S J, Mayer E L, He L, Traina T A, Carey L A, Krag K J, et al. TBCRCO009: A Multicenter Phase II Clinical Trial of Platinum Monotherapy With Biomarker Assessment in Metastatic Triple-Negative Breast Cancer. J Clin Oncol. 2015, the contents of each of which are incorporated herein by reference in their entirety), are more likely to benefit from platinum treatment.

This potential for patient selection has formed the basis for exploring the preliminary activity of Compound 8 in tumor-specific expansion patient cohorts once the safety profile and MTD or recommended Phase 2 dose (RP2D) has been established in the Dose-escalation Phase. In the Cohort-expansion Phase, the preliminary safety and activity of Compound 8 are evaluated in the following distinct patient cohorts: 1) BRCA1/BRCA2 mutated advanced pancreatic cancer, with no more than 2 prior lines of chemotherapy in the advanced disease setting; 2) BRCA1/BRCA2 mutated advanced prostate cancer, with no more than 1 prior line of chemotherapy in the advanced disease setting (unlimited hormonal therapies allowed); and 3) other solid tumors with BRCA1/BRCA2 mutations, including triple-negative breast cancer (TNBC) and ovarian cancer, with no more than 2 prior lines of chemotherapy in the advanced disease setting.

Objectives:

Dose Escalation Phase

Primary

The primary objective of the Dose-escalation Phase is to determine the safety, tolerability, dose-limiting toxicities (DLTs), maximum tolerated dose (MTD), and recommended phase 2 dose (RP2D) of Compound 8 administered intravenously (IV) every 21 days as monotherapy in patients with advanced solid tumors.

Secondary

The secondary objectives of the Dose-escalation Phase are to evaluate the plasma pharmacokinetics (PK) of Compound 8 as monotherapy in patients with advanced solid tumors.

To assess preliminary evidence of anti-tumor activity of Compound 8 as monotherapy in patients with advanced solid tumors, as determined by the Investigator using the Response Evaluation Criteria in Solid Tumors (RECIST), version 1.1 (Eisenhauer et al., 2009, the contents of which are incorporated herein by reference in their entirety).

Cohort-expansion Phase

Primary

The primary objective of the Cohort-expansion Phase is:
To further evaluate the safety, tolerability, and anti-tumor activity of Compound 8 as monotherapy in the following tumor-specific cohorts:
Compound 8 as monotherapy in patients with advanced BRCA1 or BRCA 2 mutation-positive pancreatic cancer who have received 1 or 2 prior lines of chemotherapy in the advanced disease setting (N ~10-15);
Compound 8 as monotherapy in patients with advanced BRCA1 or BRCA 2 mutation-positive prostate cancer who have received up to 1 prior line of chemotherapy in the advanced disease setting (N ~10-15);
Compound 8 as monotherapy in patients with advanced BRCA1 or BRCA 2 mutation-positive solid tumors who have received no more than 2 lines of chemotherapy in the advanced disease setting (N ~20-30). Of the 20 to 30 patients planned to be enrolled in Expansion Cohort 3, a minimum of 10 patients each must be in one of the following 2 categories:
Patients with BRCA1 or BRCA 2 mutation-positive triple-negative breast cancer who have received no more than 2 prior lines of chemotherapy in the advanced disease setting;
Patients with BRCA1 or BRCA 2 mutation-positive ovarian cancer who have received no more than 2 prior lines of chemotherapy in the advanced disease setting.

Methodology

Protocol Compound 8-001 is an open-label, Phase 1 study evaluating Compound 8 as monotherapy in patients with advanced solid tumors. The study has 2 phases, a Dose-escalation Phase in patients with advanced solid tumors, and a Cohort-expansion Phase in patients with predicted loss of function BRCA1 or BRCA 2 mutation-positive solid tumors, including pancreatic, prostate, breast, and ovarian cancer.

After provision of written informed consent, patients are screened for study eligibility within 14 days before the first study drug dose. Patients who are determined to be eligible, based on screening assessments, will be enrolled in the study on Cycle 1, Day 1 (C1D1; baseline). A treatment cycle is 21 days in length. All patients receive Compound 8 administered IV on Day 1 every 21 days; the Compound 8 dose received is dependent on the cohort/phase in which the patient is enrolled. During treatment, patients attend study center visits and have study evaluations performed on D1, D8, and D15 of each treatment cycle. In the Dose-escalation Phase, patients also attend a study center visit on C1D3 or C1D4. All study visits are conducted on an out-patient basis, but may be conducted on an in-patient basis per institutional policy.

In the absence of unacceptable Compound 8 treatment-related toxicity or disease progression, patients receive Compound 8 treatment for up to 1 year at the discretion of the Investigator and beyond 1 year with the agreement of the Investigator and the Sponsor.

After discontinuation of study drug, patients complete an End of Treatment (EOT) visit within 30 days after the last study drug dose. Thereafter, patients are contacted via telephone on an every 3-month-basis for survival status.

Safety is assessed during the study by documentation of adverse events (AEs), clinical laboratory tests, physical examination, vital sign measurements, electrocardiograms (ECGs), and Eastern Cooperative Oncology Group (ECOG) performance status (PS).

Serial blood samples for PK are collected from all patients in the Dose-escalation Phase.

During Screening, all sites of disease are assessed by computed tomography (CT).

If the anatomic region cannot be adequately imaged by CT, magnetic resonance imaging (MRI) may be used instead, with the approval of the Medical Monitor. Tumor measurements are repeated within 7 days of the first study drug dose in every other cycle, starting in C3, and at the EOT visit. (Such assessments will be performed more frequently, if indicated). Repeat assessments use the same radiographic methods as used at baseline. Disease response is assessed by the Investigator using RECIST, version 1.1 (Eisenhauer E A, Therasse P, Bogaerts J, Schwartz L H, Sargent D, Ford R, Dancey J, Arbuck S, Gwyther S, Mooney M, Rubinstein L, Shankar L, Dodd L, Kaplan R, Lacombe D, Verweij J. New response evaluation criteria in solid tumours: revised RECIST guideline (version 1.1). Eur J Cancer. 2009; 45 (2):228-47, the contents of which are incorporated herein by reference in their entirety).

Dose-escalation Phase:

Patients with advanced solid tumors are eligible for participation in the Dose-escalation Phase.

The Dose-escalation Phase initially employ an accelerated titration design, with a single patient enrolled in each cohort (i.e., Single-patient Cohorts). The initial patient receives Compound 8 monotherapy at a starting dose of 20 mg/m$^2$. Doses are escalated in 100% increments (i.e., doubling), until ≥Grade 2 toxicity (with the exception of alopecia), as determined according to the United States (US) National Cancer Institute (NCI) Common Terminology Criteria for Adverse Events (CTCAE), version 4.03, is encountered, at which point that cohort and all subsequent monotherapy cohorts follow a classical "3+3" dose escalation design (i.e., Standard Cohorts). (If a dose of 80 mg/m$^2$ is reached without a ≥Grade 2 toxicity considered by the Investigator to be study drug-related, then the accelerated titration procedure cease, and the standard dose escalation procedure followed, starting with the 80 mg/m$^2$ cohort.) Doses are further escalated in 25 to 50% increments, based on Safety Review Committee (SRC) decision, until the MTD is reached. Based on the interim evaluation of the safety and tolerability data of the previous dose level, it may also be decided that accrual will take place at an intermediate dose level.

All patients within a cohort who complete C1, have safety assessments performed through C2D 1, and are assessed for DLT before enrollment of the next cohort may commence. If <33% patients within a cohort have a DLT (i.e., <2 of up to 6), then enrollment of the next cohort may commence with approval from the Medical Monitor. If ≥33% (≥2 of up to 6) of patients within a cohort experience a DLT, then the DLT dose level have been reached and the previous lower dose level is considered the preliminary MTD. A total of 6 to 10 patients are treated at the MTD or RP2D to provide further characterization of safety, tolerability, and PK of Compound 8.

The RP2D is based on the findings of the safety, tolerability, PK, and activity profile of Compound 8 in patients who received monotherapy in the Dose-escalation Phase. This RP2D is used in the expansion cohorts in the Cohort-expansion Phase.

Cohort-expansion Phase:

The Cohort-expansion Phase begin once the RP2D is identified, even if enrollment and/or treatment of all patients through C2D1 at the MTD is not complete in the Dose-escalation Phase. The RP2D may be changed during the conduct of the Cohort-expansion Phase, with patients' dose adjusted accordingly, based on observations related to PK and any cumulative toxicity observed after multiple cycles. The RP2D may be equal to or higher than the preliminary MTD, but less than the non-tolerated dose (i.e., the dose at which ≥2 patients experienced DLT).

In the Cohort-expansion Phase, Compound 8 monotherapy is evaluated using the RP2D identified in the Dose-escalation Phase. Up to 3 Expansion Cohorts consisting of distinct subsets of patients with selected BRCA1 or 2 mutation-positive solid tumors are enrolled (see Objectives, Cohort Expansion Phase for tumor types). The final decision about which Expansion Cohorts to study is based on data from the Dose-escalation Phase and/or nonclinical data.

The safety and anti-tumor activity of Compound 8 will be assessed in the expansion cohorts. As well, tumor markers appropriate for the patient's solid tumor (e.g., carcinoembryonic antigen [CEA] and cancer antigen [CA]-19-9 in pancreatic cancer; CA-125 in ovarian cancer; prostate-specific antigen [PSA] in prostate cancer) are measured.

Number of Patients:

Dose-escalation Phase:

One patient is enrolled in each Single-patient Cohort and 3 to 6 patients are enrolled in each Standard Cohort, based on a standard Phase 1 dose escalation scheme. Each patient participates in only 1 dose cohort. The total number of patients to be enrolled in the Dose-escalation Phase is dependent upon the observed safety profile, which determines the number of patients per dose cohort, as well as the number of dose escalations required to achieve the MTD of Compound 8 and establish the RP2D.

A sample size of at least 3 patients in each Standard Cohort, expanding to 6 patients in the event of a marginal DLT rate (33%), was deemed to be a safe and conventional approach in the dose escalation of a novel oncologic agent. Assuming a true DLT rate of 5% or less, there would be a 3% chance that dose escalation would be halted in a given cohort (i.e., observing 2 or more patients with DLT). If a true DLT rate of 50% is assumed, then there would be an 83% chance that dose escalation would be halted in a given cohort.

As stated previously, additional 6 to 10 patients are enrolled at the MTD or RP2D to provide further characterization of the safety, tolerability, and PK of Compound 8.

Cohort-expansion Phase:

A total of up to 60 patients are enrolled in the Cohort-expansion Phase, including 10 to 15 patients in each Expansion Cohorts 1 and 2 and 20 to 30 patients in Expansion Cohort 3 (with at least 10 patients in each Expansion Cohorts 3A and 3B). The sample size of at least 10 patients per cohort is considered sufficient to evaluate the tolerability and preliminary activity of Compound 8 in patients with distinct tumor types. No formal sample size calculation was performed.

Diagnosis and main criteria for inclusion:

All Patients

All patients must meet all of the following criteria to be eligible to participate:

Male or female aged ≥18 years;

Patients with a history of brain metastasis are eligible for the study, provided they meet all the following criteria: a) brain metastasis were treated; b) there is no evidence of progression or hemorrhage after treatment; c) dexamethasone was discontinued at least 2 weeks before C1D1; and d) treatment with dexamethasone and/or anti-epileptic drugs is not required during study participation;

ECOG PS score of 0-1;

Adequate organ function within 14 days before C1D1, defined as follows:

Bone marrow: Absolute neutrophil count (ANC) ≥1.5× $10^9$/L, platelet count ≥100×$10^9$/L, and hemoglobin ≥9 g/dL.;

Hepatic: total bilirubin ≤1.5× the upper limit of normal (ULN) and alanine aminotransferase (ALT) and aspartate aminotransferase (AST)≤1.5×ULN (≤5×ULN if liver metastases are present);

Renal: normal serum creatinine or estimated creatinine clearance ≥60 mL/min (Cockroft-Gault formula).

If a female of childbearing potential, negative serum pregnancy test within 72 hours before C1D1 and agrees to use a physician-approved method of birth control from 30 days before C1D1 through 30 days after the last study drug dose;

If male, is surgically sterile or agrees to use a physician-approved method of birth control from 30 days before C1D1 through 30 days after the last study drug dose;

Ability to understand and willingness to sign informed consent form prior to initiation of study procedures;

Measurable disease per RECIST, version 1.1 (Eisenhauer et al., 2009, the contents of which are incorporated herein by reference in their entirety), (i.e., at least 1 measurable lesion ≥20 mm by conventional techniques or ≥10 mm by spiral CT scan or MRI), with the last imaging performed within 14 days before the first study drug dose.

Patients in the Dose-escalation Phase

Patients in the Dose-escalation Phase also must meet the following additional criterion:

Locally advanced solid tumor other than a primary central nervous system (CNS) tumor for which the patient has received ≤3 prior lines of chemotherapy. (There is no restriction regarding receipt prior therapy with targeted agents, immunotherapy, or hormone therapy).

Patients in the Cohort-expansion Phase

Patients in the Cohort-expansion Phase also must meet the following additional criterion:

Histologically- or pathologically-confirmed solid tumor in one of the following categories:

Advanced BRCA1 or 2 mutation-positive pancreatic cancer for which the patient has received 1 or 2 prior lines of chemotherapy in the advanced disease setting (Expansion Cohort 1);

Advanced BRCA1 or 2 mutation-positive prostate cancer, for which the patient has received up to 1 prior line of chemotherapy in the advanced disease setting (Expansion Cohort 2);

Advanced BRCA1 or 2 mutation-positive solid tumors, for which the patient has received no more than 2 prior lines of chemotherapy in the advanced disease setting (Expansion Cohort 3), including:

BRCA1 or 2 mutation-positive triple-negative breast cancer, for which the patient has received no more than 2 prior lines of chemotherapy in the advanced disease setting (Expansion Cohort 3A);

BRCA1 or 2 mutation-positive ovarian cancer, for which the patient has received no more than 2 prior lines of chemotherapy in the advanced disease setting (Expansion Cohort 3B).

Patients meeting any of the following criteria are not eligible for study participation:

History of leptomeningeal disease or spinal cord compression;

Underwent major surgery within 4 weeks before C1D1 or received cancer-directed therapy (chemotherapy, radiotherapy, hormonal therapy, biologic or immunotherapy, etc.) or an investigational drug or device within 14 days (6 weeks for mitomycin C and nitrosoureas) or 5 half-lives of that agent (whichever is shorter) before C1D1. A minimum of 10 days between termination of the investigational drug and administration of Compound 8 is required. In addition, any drug-related toxicity, with the exception of alopecia, must have recovered to ≤Grade 1;

Grade 2 or greater peripheral neuropathy at baseline (C1D1);

If female, pregnant or breast-feeding;

Known human immunodeficiency virus (HIV) infection or hepatitis B or C infection, as such patients may be at increased risk for toxicity due to concomitant treatment and disease-related symptoms may preclude accurate assessment of the safety of Compound 8;

Any primary CNS tumor (e.g., astrocytoma, glioblastoma);

Hypersensitivity to any platinum-containing agents;

Any other condition that, in the opinion of the Investigator, would compromise the patient's safety or interfere with the conduct of the study;

Investigational Product, Dosage and Mode of Administration:

Compound 8 Powder for Injection is a sterile lyophilized powder containing Compound 8, a cisplatin pro-drug, along with mannitol, sodium citrate, and citric acid. The product is intended to be reconstituted and infused IV with an isotonic solution. Compound 8 Powder for Injection will be supplied in 50 mL, type I glass amber bottles.

Patients will receive Compound 8 administered IV over 60 minutes on D1 every 21 days. Patients are to receive IV hydration per standard of care before and after each Compound 8 dose.

In the Dose-escalation Phase, the starting dose of Compound 8 as monotherapy is 20 mg/m². Dose escalation will be according to an accelerated titration design (Simon R, Freidlin B, Rubinstein L, Arbuck S G, Collins J, Christian M C. Accelerated titration designs for phase 1 clinical trials in oncology. J Natl Cancer Inst 1997; 89:1138-47, the contents of which are incorporated herein by reference in their entirety), and then by a standard 3+3 design. The planned dose levels are as follows and listed in Table 20:

TABLE 20

Dose Escalation Schedule
Dose Escalation (Modified Fibonacci Design)

| Dose Level | % Increment from Prior Dose Level | Compound 8 Dose (mg/m²) |
|---|---|---|
| 1 | — | 20 |
| 2 | 100% | 40 |
| 3 | 100% | 80[1] |
| 4 | 50% | 120 |
| 5 | 50% | 180 |
| 6 | 33% | 240 |
| 7 | 33% | 320 |
| 8 | 25% | 400 |
| 9 | 25% | 500 |

[1]If a dose of 80 mg/m² is reached without a ≥Grade 2 toxicity considered by the Investigator to be study drug-related, then the accelerated titration procedure will cease, and the standard dose escalation procedure followed, starting with the 80 mg/m² cohort.

As stated previously, based on the interim evaluation of the safety and tolerability data of the previous dose level, it may also be decided that accrual will take place at an intermediate dose level. The level of dose escalation and a decision to go to an intermediate dose level are determined by the SRC prior to dose escalation, but do not exceed the planned dose according to the pre-specified schema.

In the Dose-escalation phase, if a patient is tolerating Compound 8 without evidence of disease progression, the patient may, after C1, have the dose increased to a dose that has already been established as tolerable by the SRC, and with the agreement of the Sponsor's Medical Monitor.

In the Cohort-expansion Phase, Compound 8 is administered at the RP2D, as established in the Dose-escalation Phase.

Duration of Treatment:

In the absence of unacceptable Compound 8 treatment-related toxicity or disease progression, patients may receive Compound 8 treatment for up to 1 year at the discretion of the Investigator and beyond 1 year with the agreement of the Investigator and the Sponsor.

Criteria for Evaluation:

Safety: Safety is assessed by periodic physical examinations, 12-lead ECGs, clinical laboratory assessments, and monitoring of AEs. AEs are graded using the NCI CTCAE, version 4.03.

An SRC, consisting of the Sponsor's Medical Monitor and participating Investigators, hold teleconferences approximately every 1-2 weeks during the Dose-escalation Phase to review toxicities occurring in the current cohort and determine DLT. Based on its review, the SRC determines whether the escalation to the next dose level may commence or the current cohort is to be expanded or an intermediate dose level explored.

Anti-tumor Activity:

Disease response is assessed by the Investigator, using RECIST, version 1.1. In the Cohort Expansion Phase, tumor markers appropriate for the patient's solid tumor (e.g., CEA and CA-19-9 in pancreatic cancer; CA-125 in ovarian cancer; PSA in prostate cancer), also are measured.

Pharmacokinetics:

The PK profile is assessed in the Dose-escalation Phase by determining the plasma levels of Compound 8 at intervals throughout the study.

Statistical Methods:

PK is characterized by fitting an appropriate compartmental model to the complete set of data for each patient. Statistical analyses of safety, PK, and anti-tumor activity are primarily descriptive in nature, as the goal of the study is to determine the DLTs, MTD, and recommended dose of Compound 8 to be used for further investigation. This goal is achieved by the results of a deterministic algorithm; thus, statistical hypothesis testing is neither intended nor appropriate within this context.

Continuous variables are summarized using descriptive statistics [n, mean, standard deviation, median, minimum, and maximum]. Categorical variables are summarized showing the number and percentage (n, %) of patients within each classification.

Schedules of Events:

The schedule of events is presented in FIGS. 14-1, 14-2 and 14-3. C=cycle; D=day; ECOG=Eastern Cooperative Oncology Group; EOT=end of treatment.

After completion of the EOT visit, study center personnel will contact patients via telephone on an every 3-month-basis for survival status;

Screening serologies include human immunodeficiency virus (HIV), hepatitis B surface antigen (HBsAg), and hepatitis C virus deoxyribonucleic acid (HCV DNA);

If screening evaluation is done within 7 days before baseline (C1D1), it need not be repeated on C1D1;

Body surface area (BSA) is to be calculated by study center personnel using the Dubois method of calculation. BSA is to be calculated before study drug administration on C1D1 and recalculated before study drug administration of every other treatment cycle, starting with C3;

Hematology parameters include hemoglobin, hematocrit, red blood cell (RBC) count, platelet count, and white blood cell (WBC) count with differential. On study drug administration days, results must be available and reviewed before study drug administration;

If screening evaluation is done within 72 hours before baseline (C1D1), it need not be repeated on C1D1;

Clinical chemistries include chloride, carbon dioxide, sodium, potassium, calcium, magnesium, blood urea nitrogen, creatinine, glucose, albumin, alkaline phosphatase, AST, ALT, total bilirubin, and total protein. Samples may be collected up to 48 hours prior to scheduled clinic visits. On study drug administration days, results must be reviewed by the Investigator prior to study drug administration;

Coagulation studies include prothrombin time (PT) and activated partial thromboplastin time (aPTT);

Urinalysis includes specific gravity, pH, blood, glucose, protein, ketones, and microscopic examination of sediment;

Serum pregnancy testing is required only for females of childbearing potential, and Pregnancy testing is to be repeated on-study any time pregnancy is suspected;

For baseline tumor assessment, all sites of disease should be imaged by CT. If the anatomic region cannot be adequately imaged by CT, MRI may be used instead, with the approval of the Medical Monitor. Tumor measurements are repeated within 7 days of the first study drug dose in every other cycle, starting in C3, and at the EOT visit. Repeat assessments should use the same radiographic methods as used at baseline;

Disease response is assessed by the Investigator within 14 days prior to the first dose of study drug and repeated within 7 days of the first study drug dose in every other cycle, starting in C3, and at the EOT visit using RECIST, version 1.1 (Eisenhauer E A, Therasse P, Bogaerts J, Schwartz L H, Sargent D, Ford R, Dancey J, Arbuck S, Gwyther S, Mooney M, Rubinstein L, Shankar L, Dodd L, Kaplan R, Lacombe D, Verweij J. New response evaluation criteria in solid tumours: revised RECIST guideline (version 1.1). Eur J Cancer. 2009; 45(2):228-47, the contents of each of which are incorporated herein by reference);

In the Dose-escalation Phase only, serial blood samples for PK assessments are collected on C1D1 predose and at 0.5, 1, 2, 4, and 6 hours after the start of infusion;

In the Dose-escalation Phase only, a blood sample for PK assessments is collected any time between 72 and 96 hours after the start of infusion on C1D1;

In the Dose-escalation Phase only, a blood sample for trough drug levels is collected pre-dose;

In the Dose-escalation Phase only, in ≥C2, blood samples for PK assessments are collected on D1 pre-dose and at 0.5, 1, and 2 hours after the start of infusion. If the SRC determines that sufficient PK data have been collected and additional samples for PK are not required in ≥C2, then such samples no longer are collected;

Tumor markers appropriate for the patient's solid tumor (e.g., CEA and CA-19-9 in pancreatic cancer; CA-125 in ovarian cancer; PSA in prostate cancer) are measured during Screening within 14 days prior to the first dose of study drug and repeated within 7 days of the first study drug dose in every other cycle, starting in C3, and at the EOT visit. Tumor markers are measured within ±7 days of tumor measurements, where applicable.

Treatment of Patients

Study Drug Supply

Compound 8 Powder for Injection is a sterile lyophilized powder containing Compound 8, a cisplatin pro-drug, along with mannitol, sodium citrate, and citric acid. The product is to be reconstituted with an isotonic solution and infused IV. Each dosage unit contains 100 mg of Compound 8 in a stoppered 50 mL amber vial; 100 mg Compound 8 contains 51 mg cisplatin equivalents. Alternatively, each dosage unit contains 50 mg of Compound 8 in a stoppered 50 mL amber vial.

Compound 8 Powder for Injection will be supplied in 50 mL, type I glass amber bottles.

Study Drug Packaging and Labeling

Study drug labels do bear any statement that is false or misleading in any manner or represents that the study drug is safe or effective for the purposes for which it is being investigated. The content of the labeling is in accordance with FDA and local National regulatory specifications and requirements, as applicable.

Study Drug Storage

Compound 8 Powder for Injection is to be stored frozen at ≤−20° C., protected from light. Compound 8 is to be stored in a locked area, accessible only to appropriate study personnel.

Study Drug Accountability

The FDA requires accounting of all investigational drug received by each study center. Records of drug disposition required include the date received by the center, date administered, quantity administered, and the patient to whom study drug was administered. The Investigator is responsible for the accountability of all used and unused study drug containers and unused study drug.

Each study center uses a study drug accountability log to document study drug disposition. All items on this form are completed in full. A clinical research associate (CRA) representing the Sponsor is to approve the area where study drug is to be stored and accountability records are to be maintained.

The investigator identification number and patient initials and identification number are recorded on each study drug accountability log. Each time study personnel dispense study drug for a patient, he or she records the date dispensed, amount of study drug dispensed, and his or her initials. Study personnel monitors the inventory of clinical supplies and maintain a count of all used and unused study drug. The CRA reviews study drug accountability records and remaining drug supplies during routine monitoring visits.

Study Drug Dose Preparation

The Compound 8 dose is dependent on the cohort/study phase in which the patient is enrolled. The Compound 8 dose is calculated based on body surface area (BSA), as calculated at baseline and on D1 of every other cycle thereafter, starting with C3.

For IV Infusion, each bottle of Compound 8 Powder for Injection is reconstituted with 20 mL of 0.45% Sodium Chloride Injection, USP, to yield 5 mg/mL solution of Compound 8 in 5 mM citrate buffer, 2.5% Mannitol and 0.45% sodium Chloride. The reconstituted solution is further diluted with Sodium Chloride Injection, USP 0.9% for IV infusion (250 mL over 1 hour). After reconstitution, the study center pharmacist will transfer the reconstituted solution to an infusion set. Compound 8 is infused as soon as possible, but no longer than about 3, 4, or 5 hours, after reconstitution. It may need to be protected from light.

Refer to the Pharmacy Manual for details regarding study drug dose preparation and administration.

Study Drug Administration

All patients receive Compound 8 via IV infusion over 60 minutes on D1 of each treatment cycle.

Figure 15:
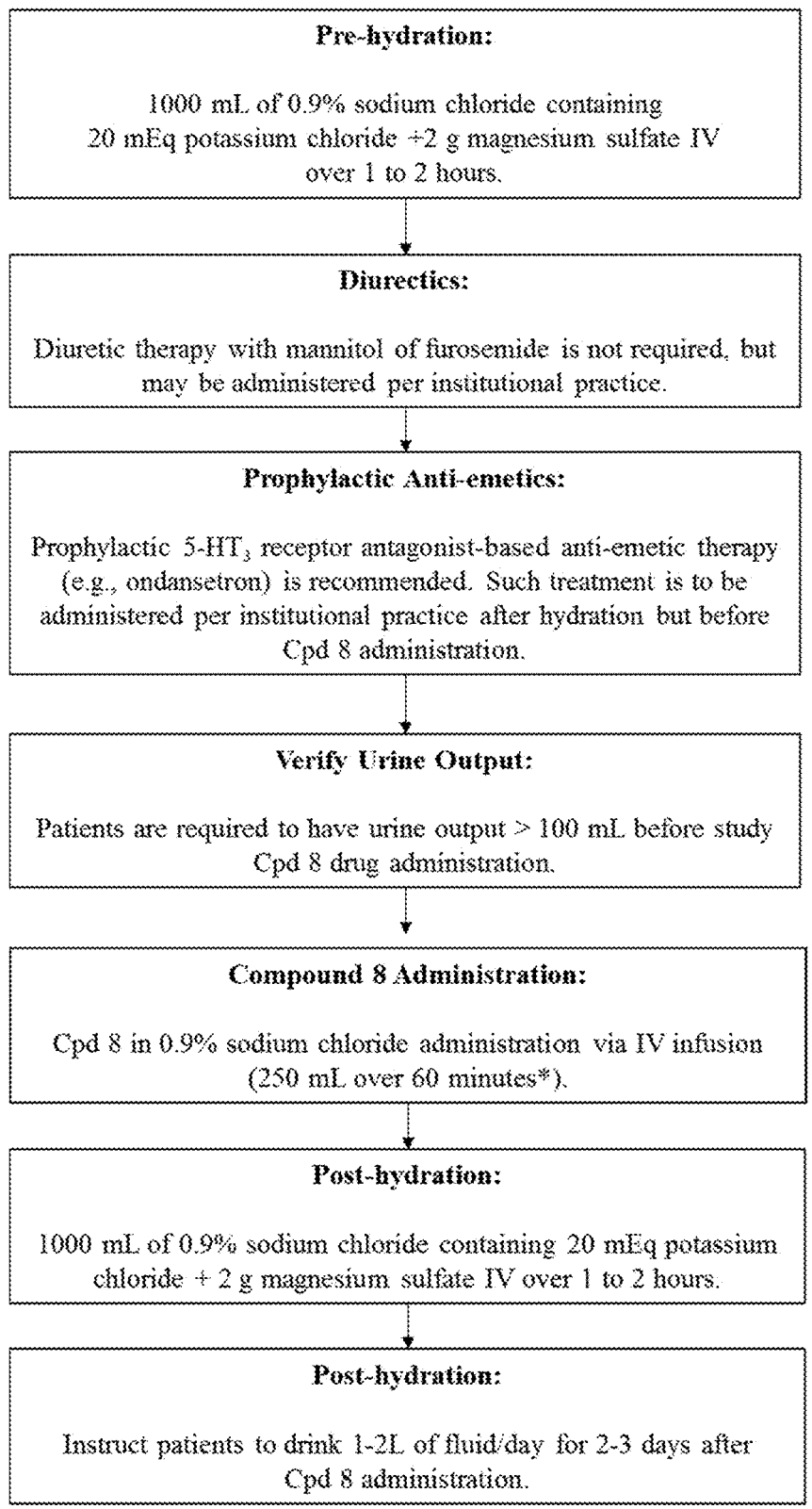
FIG. 15 shows Compound 8 administration regimen.

The administration regimen for Compound 8 is summarized in FIG. 15. As shown, all patients are required to receive IV hydration with 1,000 mL of 0.9% sodium chloride containing 20 mEq potassium chloride and 2 g magnesium sulfate over 1 to 2 hours before each Compound 8 dose. After administration of pre-hydration, patients may receive diuretic therapy with mannitol furosemide, per institutional practice. After administration of diuretics, if any, patients may receive prophylactic 5-HT3 receptor antagonist-based anti-emetic therapy (e.g., ondansetron), per institutional practice. Thereafter, study drug is administered. After completion of Compound 8 infusion, patients receive IV hydration with 1,000 mL of 0.9% sodium chloride containing 20 mEq potassium chloride and 2 g magnesium sulfate over 1 to 2 hours. Patients are instructed to drink 1-2 L of fluid/day for 2-3 days after Compound 8 administration.

For each Compound 8 infusion, the date, infusion start and stop time (24-hour clock), planned and actual dose infused, and volume infused, are documented in the source documents and transcribed in the eCRF.

Dose Escalation Phase

The starting dose of Compound 8 is 20 mg/m$^2$. The planned dose levels are summarized in Table 21.

TABLE 21

Planned Compound 8 Dose Levels
Dose Escalation (Modified Fibonacci Design)

| Dose Level | % Increment from Prior Dose Level | Compound 8 Dose (mg/m$^2$) |
|---|---|---|
| 1 | — | 20 |
| 2 | 100% | 40 |
| 3 | 100% | 80[1] |
| 4 | 50% | 120 |
| 5 | 50% | 180 |
| 6 | 33% | 240 |
| 7 | 33% | 320 |
| 8 | 25% | 400 |
| 9 | 25% | 500 |

[1]If a dose of 80 mg/m$^2$ is reached without a ≥Grade 2 toxicity considered by the Investigator to be study drug-related, then the accelerated titration procedure will cease, and the standard dose escalation procedure followed, starting with the 80 mg/m$^2$ cohort.

Compound 8 doses are escalated sequentially after the SRC, with appropriate representation from the Sponsor, Medical Monitor, and participating Investigators, reviews safety data collected during C1 from the patient(s) enrolled at the current dose level.

Each patient in a dose cohort must have received Compound 8 and completed follow-up safety evaluations through C2D1 to be eligible for the assessment of DLT.

Patients who discontinue from the study for reasons other than DLT before completing C1 are replaced.

If a DLT necessitates enrollment of additional patients into a cohort, the SRC review all safety data for that cohort after all patients have received Compound 8 and completed follow-up safety evaluations through C2D1. Based on the interim evaluation of the safety and tolerability data of the previous dose level, it may also be decided that accrual may take place at an intermediate dose level. The SRC may be convened earlier at the discretion of the Sponsor if important safety issues arise requiring the attention of the committee.

Accelerated Titration Procedure

Toxicities are graded by the Investigator using the NCI CTCAE, version 4.03.

Initially, 1 patient is enrolled into the first dose cohort. If, after that patient receives Compound 8 and has safety evaluations performed through C2D1:

The patient experiences no ≥Grade 2 toxicity considered by the Investigator to be Compound 8-related, then the next patient may be enrolled in the next dose cohort, with the approval of the SRC;

The patient experiences a ≥Grade 2 toxicity considered by the Investigator to be Compound 8-related (with the exception of alopecia) that does not meet the definition of DLT (Cohort-expansion phase), then enrollment continues in that cohort per the Standard Dose Escalation Procedure (see next subsection);

The patient experiences a DLT (Cohort-expansion phase), then enrollment continues in that cohort per the Standard Dose Escalation Procedure (see next subsection).

If a dose of 80 mg/m² is reached without a ≥Grade 2 toxicity considered by the Investigator to be study drug-related, then the accelerated titration procedure ceases, and the standard dose escalation procedure followed (see next subsection), starting with the 80 mg/m² cohort.

Standard Dose Escalation Procedure

The dose escalation procedure is summarized in Table 22.

Up to 3 patients initially are enrolled in each cohort.

After 3 patients receive Compound 8 and have safety evaluations performed through C2D1, and:

None of the 3 patients experience a DLT (Cohort-expansion Phase), then enrollment of the next cohort may commence with approval from the SRC;

1 of 3 patients within a cohort experiences a DLT (Cohort-expansion Phase), then up to 3 additional patients are to be enrolled sequentially at that dose level. If none of the additional 3 patients has a DLT (i.e., 1 of 6 patients has a DLT), then enrollment at the next scheduled dose may commence with approval from the SRC;

If ≥2 patients within a cohort experience a DLT (Cohort-expansion Phase), then the DLT dose level have been reached and the previous lower dose level is considered the MTD;

A total of 6 to 10 patients are treated at the MTD or other dose recommended for further investigation in phase 2 (i.e., RP2D) to provide further characterization of the safety, tolerability, and PK of Compound 8.

Note that enrollment in the next dose cohort can begin only when the last patient enrolled in the current dose cohort completes C1 and is assessed for DLT, provided that <2 patients in the current dose cohort experienced a DLT.

Although decisions regarding dose escalation are made based on review of data from C1, safety data are also collected from all patients continuing treatment and this is reviewed periodically by the SRC. Any detected cumulative toxicity may require later dose reductions or other action as appropriate, including further refinement of the RP2D.

TABLE 22

Summary of Dose Escalation Procedure

| Observed Safety Outcomes | Action |
|---|---|
| Accelerated Titration (Single-patient Cohorts; n = 1 each) | |
| No ≥Grade 2 AEs | Continue evaluation of single-patient dose cohorts.[1] Escalate by 100% to next dose level[1]. |
| At least 1 ≥Gr 2 AE (with the exception of alopecia) not meeting the definition of DLT | Expand current and subsequent cohorts to at least 3 patients (see Standard Dose Escalation Scheme below). |
| 1 DLT | Expand current cohort up to 6 patients or until 2 DLTs are encountered (Standard Dose Escalation Scheme below). |
| Standard Dose Escalation (Standard Cohorts; n = 3-6 each) | |
| No DLT | Escalate to next dose level. |
| 1 DLT in ≤3 patients | Expand cohort up to 6 patients. |
| 1 DLT in 6 patients | Escalate to next dose level. |
| >1 DLT in ≤6 patients | MTD reached; stop dose escalation. Possibly explore intermediate doses for the RP2D. |

Note:
DLT is defined in Cohort-expansion phase.
[1]If a dose of 80 mg/m² is reached without a ≥Grade 2 toxicity considered by the Investigator to be study drug-related, then the accelerated titration procedure will cease, and the standard dose escalation procedure followed, starting with the 80 mg/m² cohort.

Cohort-expansion Phase

In the Cohort-expansion Phase, all patients receive Compound 8 at the MTD or RP2D, as identified in the Dose-escalation phase.

The RP2D may be changed during the conduct of the Cohort-expansion Phase, with patients' dose adjusted accordingly, based on observations related to PK and any cumulative toxicity observed after multiple cycles. The RP2D may be equal to or higher than the preliminary MTD, but less than the non-tolerated dose (i.e., the dose at which ≥2 patients experienced DLT).

Definition of Dose-limiting Toxicity (DLT)

DLT is defined as the occurrence of any of the following events within the first cycle of treatment (i.e., through C2D1) that are considered by the Investigator to be at least possibly related to Compound 8:

Inability to begin C2 as scheduled (i.e., on Study Day 22) due to any Compound 8-related toxicity (either hematologic or non-hematologic);

Grade 4 hematologic toxicity of ≥7 days duration;

≥Grade 3 thrombocytopenia associated with ≥Grade 2 bleeding;

Febrile neutropenia;

≥Grade 3 non-hematologic toxicity, with the exceptions of:

nausea and/or vomiting and diarrhea that resolve to ≤Grade 3 within 48 hours of initiating maximal supportive treatment;

Grade 3 diarrhea, fever (in the absence of neutropenia), or fatigue that resolves to ≤Grade 3 within 72 hours.

Grade 3 laboratory abnormalities that are not associated with symptoms and resolve to Grade 1 or baseline by C2D1.

Any other significant toxicity considered by the Investigator and Sponsor's medical representatives to be dose-limiting (e.g., any toxicity considered at least possibly related to Compound 8 that results in patient withdrawal during C1).

Definition of Maximum Tolerated Dose (MTD)

The MTD is defined as the highest dose level at which <33% of patients experience DLT in C1.

Definition of Recommended Phase 2 Dose (RP2D)

The RP2D may be equal to or higher than the preliminary MTD, but less than the non-tolerated dose (i.e., the dose at which ≥33% of patients experienced DLT). The RP2D is determined in discussion with the Sponsor, Medical Monitor, and Investigators. Additionally, observations related to PK, and any cumulative toxicity observed after multiple cycles may be included in the rationale supporting the RP2D.

Dose Modifications

Dose-escalation Phase

In the Dose-escalation Phase, all patients must receive Compound 8 at the prescribed dose in C1. After C1, if, in the Investigator's judgment, the patient is not tolerating a dose level, the Medical Monitor should be contacted regarding dose reduction to a lower Compound 8 dose level, or discontinuation of treatment, as appropriate. If a patient is tolerating Compound 8 without evidence of PD, the patient may, after C1, have the dose increased to a dose that has already been established as safe and tolerable by the SRC, with the agreement of the Sponsor's Medical Monitor.

Cohort-expansion Phase

If possible, toxicities are to be managed symptomatically. The appropriate treatment should be used to ameliorate signs and symptoms, including antiemetics for nausea and vomiting, antidiarrheals for diarrhea, and antipyretics for fever.

No more than 1 dose reduction is to be implemented for each patient, with no dose re-escalation.

Dose Modifications for Hematologic Toxicities

Neutropenia

Neutropenia is to be treated as medically indicated. In addition, the measures listed in Table 23 are recommended.

Thrombocytopenia

For Grade 3 or 4 thrombocytopenia delay treatment for up to 2 weeks until platelet count is ≥100×10$^9$/L. Once platelet count returns to ≥100×10$^9$/L, restart study drug at a dose reduced by 25%.

If platelet count does not return to ≥100×10$^9$/L after delaying treatment for up to 2 weeks (i.e., within 5 weeks after the previous study drug dose), then study drug is to be discontinued.

Anemia

For Grade 2 or 3 anemia, delay treatment for up to 2 weeks (i.e., within 5 weeks after the previous study drug dose) until anemia resolves to Grade 1 or baseline (hemoglobin ≥10 g/dL). Treatment with blood transfusions and/or erythropoietin is allowed. Once hemoglobin returns to ≥10 g/dL, restart study drug at a dose reduced by 25%.

If hemoglobin does not return to ≥10 g/dL after delaying treatment for up to 2 weeks (i.e., within 5 weeks after the previous study drug dose), then study drug is discontinued.

Study drug is to be discontinued in the event of Grade 4 anemia.

Non-hematologic Toxicities

Peripheral Neuropathy

For ≥Grade 3 peripheral neuropathy delay treatment for up to 2 weeks until resolution to ≤Grade 2. Once peripheral neuropathy resolves to ≤Grade 2, restart study drug at a dose reduced by 25%.

If peripheral neuropathy does not resolve to ≤Grade 2 after delaying treatment for up to 2 weeks (i.e., within 5 weeks after the previous study drug dose), then study drug is to be discontinued.

Nephrotoxicity

Creatinine clearance is to be estimated using the Cockcroft-Gault formula before study drug administration on D1 of each cycle. If the patient's estimated creatinine clearance is:

≥60 mL/min, retreat at 100%;

45 to 60 mL/min, retreat at a dose reduced by 25%;

<45 mL/min, discontinue study drug.

Ototoxicity

Study drug is discontinued in the event of ≥Grade 3 ototoxicity considered by the Investigator to be Compound 8-related.

Nausea and Vomiting

For ≤Grade 2 nausea and vomiting, manage symptomatically and retreat at 100% on schedule.

For ≥Grade 3 nausea and vomiting, manage symptomatically and delay treatment for up to 2 weeks until resolution to ≤Grade 2 or baseline. Thereafter, restart study drug at a dose reduced by 25%. If nausea and vomiting to not resolve

TABLE 23

Dose Reduction Due to Neutropenia and Associated Complications

| Adverse Event | Action to be Taken |
| --- | --- |
| Grade 4 neutropenia lasting <5 days | Retreat at 100% on schedule. Consider prophylactic granulocyte-colony stimulating factor (G-CSF) for subsequent treatment. |
| Grade 4 neutropenia lasting for ≥5 days | Delay treatment for up to 2 weeks (i.e., up to 5 weeks after the previous study drug dose) until ANC is ≥1.5 × 10$^9$/L. Once ANC returns to ≥1.5 × 10$^9$/L, resume study drug at 100%, but with prophylactic G-CSF for subsequent treatment. |
| Grade 3/4 neutropenia with oral temperature ≥38.5° C. | If neutropenia recurs, delay treatment for up to 2 weeks (i.e., up to 5 weeks after the previous study drug dose) until ANC is ≥1.5 × 10$^9$/L. Once ANC returns to ≥1.5 × 10$^9$/L, restart study drug at a dose reduced by 25%. |
| Infection (documented with Grade 3/4 neutropenia) | If ANC recurs on the reduced dose or if ANC recovery to ≥1.5 × 10$^9$/L does not occur within 5 weeks of the previous study drug dose, then study drug is to be discontinued. | to ≤Grade 2 after a delay of up to 2 weeks (i.e., 5 weeks after the previous study drug dose), then study drug is discontinued.

Rationale for the Dose Selected

Human Starting Dose

The final dose projected in humans using allometry is the dose that will result in $1/10^{th}$ the AUC observed in rats at the severely toxic dose in 10% of the animals ($STD_{10}$) in the GLP repeat dose toxicity study. The closest dose to $STD_{10}$ in this study was the MTD of 19 mg/kg. The observed AUC at 19 mg/kg in rats was 7,060 υM·hours; thus, $1/10^{th}$ the exposure is 706 υM·hours. Using the Dose=AUC×clearance relationship, the resulting starting dose in humans is estimated to be 20 mg/m² (Table 24).

TABLE 24

Projected and Measured PK Parameter Overview

| Parameter | Mouse | Rat | Dog | Human MTD | Human Efficacy AUC and Dose | Human Safe Starting AUC and Dose |
|---|---|---|---|---|---|---|
| Projected vs. Measured | | Measured | | Projected | Projected | Projected |
| $t_{1/2}$ (h) | 23.2 | 53.8 | 109 | 450[2] | 450[2] | 450[2] |
| Dose (mg/m²) | 41.8 (MTD) | 120 (MTD[1]) | 205 (MTD) | 383 | 98 | 20 |
| MTD AUC µM·h | 3,680 | 7,060 | 10,100 | 14,422 | 3,680 | 706 |

[1]$STD_{10}$ was not achieved with statistical significance in Study 2347-007, so the more conservative MTD closest-dose was used to assess safe starting dose exposure.
[2]Literature value for albumin.

Concomitant Medications

All prescription and non-prescription medications and therapies, including pharmacologic doses of vitamins, herbal medicines, or other non-traditional medicines, taken from 30 days prior to the first dose of Compound 8 through the EOT Visit must be recorded in the eCRF. On PK sample collection days, both the date and time of concomitant medications and therapies must be recorded.

Excluded Medications

The following medications and treatments are prohibited during study participation.

Any investigational agent or device other than Compound 8, including agents that are commercially available for indications other than the patient's solid tumor that are under investigation for the treatment of solid tumors;

Any anti-neoplastic treatment with activity against solid tumors other than study drug. This includes high doses of corticosteroids;

Medications known to be nephrotoxic (e.g., aminoglycoside antibiotics [gentamicin, amikacin, tobramycin], amphotericin B, cyclosporine, tacrolimus, vancomycin);

Medications cleared by CYP2B6 (e.g., rifampin);

Pyridoxine;

Plasma levels of anticonvulsant agents (e.g., clonazepam, phenytoin) may become subtherapeutic during Compound 8 therapy. Patients receiving such agents are to be monitored and the anti-epileptic agent dose adjusted at the Investigator's discretion.

Radiation therapy to target lesions or surgical removal of target lesions is considered indicative of PD and will result in the patient being inevaluable for disease response.

Permitted Medications

Medications and treatments other than those specified in Excluded Medications, including palliative and supportive care for disease-related symptoms are permitted during the study. Patients should be closely monitored, and treatment is to be instituted for disease-related symptoms, as appropriate.

Diuretics and Antiemetics: As described in Study Drug Administration section, after receipt of required prehydration and before each Compound 8 dose, patients may receive diuretic therapy with mannitol or furosemide, per institutional practice. After administration of diuretics but before Compound 8 administration, if any, patients may receive prophylactic 5-HT3 receptor antagonist-based anti-emetic therapy (e.g., ondansetron), per institutional practice;

Hematopoietic Growth Factors: Hematopoietic growth factors may be used with the approval of the Medical Monitor and in accordance with the American Society of Clinical Oncology guidelines. Patients who experience grade 4 neutropenia lasting for ≥5 days; Grade 3/4 neutropenia with oral temperature ≥38.5° C.; or infection with Grade 3/4 neutropenia may receive treatment with colony-stimulating factors at the Investigator's discretion;

Luteinizing hormone-releasing hormone (LHRH) agonists: Patients with prostate cancer may receive concomitant therapy with LHRH agonists at the discretion of the Investigator.

Randomization and Blinding

This is an open-label, dose-escalation study; no randomization or blinding methods are employed.

Pharmacokinetic Assessments

For all patients in the Dose-escalation Phase, serial blood samples for PK assessments are collected at the following timepoints:

C1D1: pre-dose and at 0.5, 1, 2, 4, 6, and 72 to 96 hours after the start of study drug infusion;

C1D8;

C1D15;

≥C2D1: pre-dose and at 0.5 and 1 and 2 hours after the start of study drug infusion (If the SRC determines that sufficient PK data have been collected and additional samples for PK are not required in ≥C2, then such samples no longer will be collected);

The time of PK sample collection is relative to the start of study drug infusion;

The calendar date and exact 24-hour clock time of blood sample collection for PK assessments will be documented in the source document and the eCRF;

Blood samples for PK assessments are to be processed, stored, and shipped as described in the Study Manual.

Anti-tumor Activity Assessments
Tumor Markers

Tumor markers applicable to the patient's solid tumor type (e.g., CEA and CA-19-9 in pancreatic cancer; CA-125 in ovarian cancer; PSA in prostate cancer) are measured at the timepoints designated in FIGS. 14-1, 14-2 and 14-3 or patients in the Expansion Cohorts. Blood for tumor marker assessment is collected within ±7 days of tumor measurements, where applicable.

Tumor Measurements and Assessment of Disease Response

Tumor measurements and disease response assessments are performed for all patients. (All patients are required to have measurable disease during Screening). Disease response assessments are performed within 7 days of the first study drug dose in every other cycle, starting in C3, and at the EOT visit.

For such patients, all sites of disease should be imaged by computed tomography (CT). With the approval of the Medical Monitor, if the anatomic region cannot be adequately imaged by CT, magnetic resonance imaging (MRI) may be used instead. Subsequent assessments should use the same radiographic methods as used during Screening. Anatomical measurements (summed across target lesions) are documented during Screening and each subsequent evaluation. Objective assessments are performed during Screening and before the first study drug dose of every other cycle, starting with C3. When possible, the same qualified physician interprets results to reduce variability. Radiographic images are maintained at the study center and test results and Investigator's findings are filed in the patient's source documents.

During Screening, tumor lesions are categorized as measurable versus non-measurable and target versus non-target, as follows.

Measurable Versus Non-measurable

Measurable: lesions that could accurately be measured in at least one dimension as ≥10 mm by CT scan or caliper measurement by clinical examination or ≥20 mm by chest X-ray; the longest diameter is recorded.

Non-measurable: all other lesions, including small lesions (longest diameter <10 mm or pathological lymph nodes with ≥10 to <15 mm short axis) and truly non-measurable lesions.

Target Versus Non-target

Target: all measurable lesions up to a maximum of 2 lesions per organ and 5 lesions in total, representative of all involved organs, are identified as target lesions and measured and recorded at Screening. Target lesions are selected on the basis of their size (i.e., those with the longest diameter) and suitability for accurate repeated measurement. The sum of the longest diameter for all target lesions is calculated and recorded in the eCRF as the baseline sum longest diameter.

Non-target: all other lesions not classified as target lesions (or sites of disease) are identified as non-target lesions and are recorded in the eCRF. Measurement of non-target lesions is not required.

Disease response in target and non-target lesions will be assessed by the Investigator using RECIST guidelines, version 1.1 (Eisenhauer et al., 2009, the contents of which are incorporated herein by reference in their entirety), according to the categories and criteria described in Table 25. The best overall response for each patient will be reported as the best response documented over the sequence of objective statuses recorded using the categories and criteria in Table 26.

TABLE 25

Response Evaluation Criteria in Solid Tumors (RECIST) Guidelines for Tumor Response
Disease Response Criteria for Target and Nontarget Lesions Evaluation of Target lesions

| | |
|---|---|
| Complete Response (CR): | Disappearance of all target lesions. |
| Partial Response (PR): | At least a 30% decrease in the sum of the LD of target lesions, taking as reference the baseline sum LD. |
| Stable Disease (SD): | Neither sufficient shrinkage to qualify for PR nor sufficient increase to qualify for PD, taking as reference the smallest sum LD since the treatment started. |
| Progressive Disease (PD): | At least a 20% increase in the sum of the LD of target lesions, taking as reference the smallest sum LD recorded since the treatment started or the appearance of one or more new lesions. |

Evaluation of Nontarget lesions

| | |
|---|---|
| Complete Response (CR): | Disappearance of all nontarget lesions and normalization of tumor marker level. |
| Incomplete Response/ Stable Disease (SD): | Persistence of one or more nontarget lesion(s) or/and maintenance of tumor marker level above the normal limits. |
| Progressive Disease (PD): | Appearance of one or more new lesions and/or unequivocal progression of existing nontarget lesions. |

Source: Eisenhauer E A, Therasse P, Bogaerts J, Schwartz L H, Sargent D, Ford R, et al. New response evaluation criteria in solid tumours: revised RECIST guideline (version 1.1). Eur J Cancer 2009; 45(2): 228-47, the contents of which are incorporated herein by reference in their entirety.
Key: LD = longest diameter.

TABLE 26

Overall Response Criteria

Patients with Target and Nontarget Lesions

| Target Lesions | Non-Target Lesions | New Lesions | Overall Response |
|---|---|---|---|
| CR | CR | No | CR |
| CR | Non-CR/Non-PD | No | PR |
| CR | Not evaluated | No | PR |
| PR | Non-PD or not all evaluated | No | PR |
| SD | Non-PD or not all evaluated | No | SD |
| Not evaluated | Non-PD | No | NE |
| PD | Any | Yes or no | PD |
| Any | PD | Yes or no | PD |
| Any | Any | Yes | PD |

TABLE 26-continued

Overall Response Criteria

Patients with Nontarget Lesions Only

| Non-Target Lesions | New Lesions | Overall Response |
|---|---|---|
| CR | No | CR |
| Non-CR/Non-PD | No | Non-CR/Non-PD |
| Not all evaluated | No | NE |
| Unequivocal PD | Yes or No | PD |
| Any | Yes | PD |

Source: Eisenhauer E A, Therasse P, Bogaerts J, Schwartz L H, Sargent D, Ford R, et al. New response evaluation criteria in solid tumours: revised RECIST guideline (version 1.1). Eur J Cancer 2009; 45(2): 228-47, the contents of which are incorporated herein by reference in their entirety.
Key: CR = complete response; NE = inevaluable; PD = progressive disease.

Any patient with a CR or PR has repeat assessments performed 4 weeks later to confirm the response.

Safety Assessments

Demographics

Patient demographics, including age, sex, race, and ethnicity, are documented during screening.

Medical History, Including Cancer History

A complete medical history is documented during screening and updated at baseline, prior to administration of the first Compound 8 dose.

The medical history includes cancer history, including the patient's primary tumor type, current disease stage, date of and disease stage at diagnosis, method of diagnosis, and all previous treatments, including systemic therapy, radiation therapy, and surgeries, as well as response to such treatment.

Each patient's BRCA status is documented.

As part of the patient's cancer history, study centers submit a local histology or cytology report obtained prior to enrollment, if available. Furthermore, paraffin blocks (preferred) or a minimum of 10 unstained slides of available archival tumor tissue are requested from the patient's local institution and collected.

Physical Examination

Complete physical examinations are performed at the time points designated in FIGS. 14-1, 14-2 and 14-3. Complete physical examinations include assessment of the following:

- General appearance;
- Head, eyes, ears, nose, and throat;
- Cardiovascular system;
- Respiratory system;
- Chest;
- Gastrointestinal system (abdomen);
- Lymphatic system;
- Musculoskeletal system;
- Skin;
- Psychiatric;
- Neurological (including questioning regarding whether the patient is experiencing any numbness and/or pain as well as light touch, sharp touch [skin prick], and temperature, position [proprioception], and vibration sensation testing. Additional neurological assessments are to be performed as appropriate for the patient's condition, at the Investigator's discretion).

Symptom-directed (i.e., abbreviated) physical examinations are conducted at all other study visits.

On dosing days, physical examinations should be completed prior to infusion. Abnormal physical examination findings that are considered by the Investigator to be clinically significant for a particular patient during screening and before dosing on C1D1 are reported as part of the patient's medical history. Abnormal, clinically significant examination findings following initiation of dosing on C1D1 are reported as an AE, if the finding represents a change from baseline.

Vital Signs

Vital signs, including blood pressure, pulse, respiration rate, and body temperature, are measured at the time points designated in FIGS. 14-1, 14-2 and 14-3Error!Reference source not found. Pulse rate and blood pressure are measured with the patient in a sitting position after a 5-minute rest.

Vital signs should be measured prior to any scheduled blood sample collection. On dosing days, vital signs are measured prior to the start of study drug infusion and before any scheduled blood sample collection.

Vital signs abnormalities that are considered by the Investigator to be clinically significant for a particular patient during screening and before dosing on C1D1 are reported as part of the patient's medical history. Abnormal, clinically significant vital signs results observed following initiation of dosing on C1D1 are reported as AEs, if the finding represents a change from baseline.

Weight and Height

Height is to be measured for all patients during screening.

Body weight is measured at the time points designated in FIGS. 14-1, 14-2 and 14-3 and at any time the patient has experienced a notable change in weight (±10%).

At Baseline, BSA is calculated by the Dubois method using screening height and baseline weight measurements. The Baseline BSA is used to determine the patient's study drug dose. Thereafter, BSA is recalculated on D1 of every other treatment cycle, starting with C3, and the patient's study drug dose adjusted accordingly.

Electrocardiogram (ECG)

A 12-lead ECG is performed at the time points designated in FIGS. 14-1, 14-2 and 14-3.

Laboratory Assessments

Laboratory assessments are performed by the local laboratory.

Laboratory abnormalities that are considered by the Investigator to be clinically significant for a particular patient during screening and before study drug administration at Baseline are reported as part of the patient's medical history and as an AE after the start of study drug administration at Baseline, where the finding represents a change from Baseline.

Hematology and Clinical Chemistries

Blood samples for hematology and clinical chemistries are collected at the time points designated in FIGS. 14-1, 14-2 and 14-3. If the screening sample is collected within 72 hours before C1D1, a sample need not be collected on C1D1.

After C1D1, samples are collected up to 48 hours before scheduled study center visits. Hematology and clinical chemistry results must be reviewed by the Investigator prior to study drug administration. If any clinically relevant hematology or clinical chemistry abnormalities are identified after the patient leaves the study center, the patient is to be contacted and appropriate follow-up performed.

The following clinical laboratory parameters are measured:

| Hematology | |
|---|---|
| Hematocrit | Platelet count |
| Hemoglobin | White blood cell count with differential |
| RBC count | |
| Chemistry | |
| Chloride | Carbon dioxide |
| Sodium | Potassium |
| Calcium | Magnesium |
| BUN | Creatinine* |
| Glucose | Albumin |
| Alkaline phosphatase | AST |
| ALT | Total bilirubin |
| Total protein | |

*Creatine clearance is to be estimated using the Cockcroft-Gault formula before study drug administration on D1 of each treatment cycle; refer to Nephrotoxicity section for dose modification criteria based on estimated creatinine clearance.

Clinical laboratory evaluations are repeated as necessary during treatment at a schedule determined by the Investigator, based on the patient's clinical status.

Urinalysis

Urine for urinalysis is collected at the time points designated in FIGS. 14-1, 14-2 and 14-3. If the screening sample is collected within 72 hours before C1D1, a sample need not be collected on C1D1.

The following urinalysis parameters are determined:

| Urinalysis | |
|---|---|
| Specific gravity | Protein |
| pH | Ketones |
| Blood | Microscopic examination of sediment |
| Glucose | |

Coagulation Studies

Blood samples for coagulations studies, including prothrombin time and activated partial thromboplastin time, are collected at the time points designated in FIGS. 14-1, 14-2 and 14-3. If the screening sample is collected within 72 hours before C1D1, a sample need not be collected on C1D1.

Pregnancy Testing

Serum samples for beta-human chorionic gonadotropin pregnancy testing are collected from females of childbearing potential (FOCBP) at the time points designated in FIGS. 14-1, 14-2 and 14-3. If the screening sample is collected within 72 hours before C1D1, a sample need not be collected on C1D1.

Pregnancy testing is repeated any time pregnancy is suspected.

A FOCBP is defined as any female who has experienced menarche and who has not undergone successful surgical sterilization (hysterectomy, bilateral tubal ligation, or bilateral oophorectomy) or is not postmenopausal (defined as amenorrhea ≥12 consecutive months; or women on hormone replacement therapy with documented serum follicle-stimulating hormone level ≥35 mIU/mL). Women who are using oral, implanted, or injectable contraceptive hormones or mechanical products, such as an intrauterine device or barrier methods (diaphragm, condoms, spermicides) to prevent pregnancy, are practicing abstinence, or whose partner is sterile (e.g., vasectomy), are considered to be of childbearing potential.

Prior to study enrollment, FOCBP must be advised of the importance of avoiding pregnancy during study participation and the potential risk factors for an unintentional pregnancy. This information will be included in the informed consent form (ICF) that must be signed by the patient. In addition, all FOCBP or fertile men with partners of childbearing potential should be instructed to contact the Investigator immediately if they suspect they or their partner might be pregnant (e.g., missed or late menstrual period) at any time during study participation.

Accordingly, the patient must agree to adequate birth control from 30 days before C1D1 through 30 days after the last study drug dose.

Patients with a positive pregnancy test result during screening or on C1D1 are not eligible for study participation. Patients with positive results any time after the start of study drug administration have study drug permanently discontinued.

Screening Serology

A blood sample for serologic testing, including HIV, hepatitis B surface antigen, and hepatitis C DNA, is collected during screening.

ECOG Performance Status

ECOG performance status is determined at the time points designated in FIGS. 14-1, 14-2 and 14-3.

The ECOG performance status scale, with corresponding Karnofsky performance status score equivalents is as follows.

TABLE 27

Eastern Cooperative Oncology Group Performance Status Scale, with Equivalent Karnofsky Performance Status Scores

| ECOG[1] | | Karnofsky[2] | |
|---|---|---|---|
| Score | Criterion | % | Criterion |
| 0 | Normal activity | 100 | Normal; no complaints; no evidence of disease |
| | | 90 | Able to carry on normal activity; minor signs or symptoms of disease |
| 1 | Symptoms but ambulatory | 80 | Normal activity with effort; some signs or symptoms of disease |
| | | 70 | Cares for self; unable to carry on normal activity or do active work |
| 2 | In bed <50% of time | 60 | Requires occasional assistance but is able to care for most of his/her needs |
| | | 50 | Requires considerable assistance and frequent medical care |
| 3 | In bed >50% of time | 40 | Disabled, requires special care and assistance |
| | | 30 | Severely disabled; hospitalization is indicated though death is not imminent |

TABLE 27-continued

Eastern Cooperative Oncology Group Performance Status Scale,
with Equivalent Karnofsky Performance Status Scores

| ECOG[1] | | Karnofsky[2] | |
|---|---|---|---|
| Score | Criterion | % | Criterion |
| 4 | 100% bedridden | 20 | Very sick; hospitalization is necessary |
| | | 10 | Moribund; fatal processes progressing rapidly |
| 5 | Dead | 0 | Dead |

[1]Oken M M, Creech R H, Tormey D C, Horton J, Davis T E, McFadden E T, Carbone P P. Toxicity and response criteria of the Eastern Cooperative Oncology Group. Am J Clin Oncol. 1982; 5: 649-655, the contents of which are incorporated herein by reference in their entirety.
[2]Mor V, Laliberte L, Morris J N, Wiemann M. The Karnofsky Performance Status Scale: an examination of its reliability and validity in a research setting. Cancer. 1984; 53: 2002-2007, the contents of which are incorporated herein by reference in their entirety.

Adverse Events

Each patient must be carefully monitored for the development of any AEs. This information should be obtained in the form of non-leading questions (e.g., "How are you feeling?") and from signs and symptoms detected during each examination, observations of study personnel, and spontaneous reports from patients.

Information about AEs will be collected from the start of Compound 8 administration on C1D1 through 30 days after the last dose of study drug.

Adverse Event Definitions, Recording, and Reporting

Definition of Adverse Events

Adverse Events (AE)

An AE is any untoward medical occurrence in a patient or clinical investigation subject administered a pharmaceutical product, and which does not necessarily have to have a causal relationship with this treatment. An AE can therefore be any unfavorable and unintended sign (including abnormal laboratory findings), symptom, or disease temporally associated with the use of an investigational product, whether or not related to the investigational product.

Any abnormal clinical or laboratory finding considered by the Investigator to be clinically significant is to be recorded in the eCRF as part of the patient's medical history if occurring prior to the start of study drug administration and as an AE if occurring after the start of study drug administration at Baseline, where the finding represents a change from Baseline.

For the purposes of this study, death and disease progression (i.e., PD) are not considered AEs and should not be reported as such. Death is considered an outcome of one or more primary AEs, and PD is considered a worsening of underlying disease and is a criterion for study drug discontinuation. PD is not to be recorded as an AE unless PD results in an outcome of death; in such cases, PD should be reported as an AE/serious adverse event (SAE) with an outcome of death.

Unexpected Adverse Event

An unexpected AE is any event for which the nature or severity is not consistent with the information in the current Investigator's Brochure.

Serious Adverse Event (SAE)

An AE or suspected adverse reaction is considered serious if, in the view of either the Investigator or Sponsor, it:
Results in death;
Is life-threatening. Life-threatening means that the patient was at immediate risk of death from the reaction as it occurred, i.e., it does not include a reaction which hypothetically might have caused death had it occurred in a more severe form;
Requires in-patient hospitalization or prolongation of existing hospitalization: Hospitalization admissions and/or surgical operations scheduled to occur during the study period, but planned prior to study entry are not considered AEs if the illness or disease existed before the patient was enrolled in the study, provided that it did not deteriorate in an unexpected manner during the study (e.g., surgery performed earlier than planned). Additional exclusions to SAE reporting include hospitalizations for:
Elective procedures;
Social/administrative reasons in the absence of an AE;
Expected deterioration caused by PD;
Results in persistent or significant disability/incapacity. Disability is defined as a substantial disruption of a person's ability to conduct normal life functions;
Is a congenital anomaly/birth defect;
Is an important medical event. An important medical event is an event that may not result in death, be life-threatening, or require hospitalization but may be considered an SAE when, based upon appropriate medical judgment, it may jeopardize the patient and may require medical or surgical intervention to prevent one of the outcomes listed in the definitions for SAEs. Examples of such medical events include allergic bronchospasm requiring intensive treatment in an emergency room or at home, blood dyscrasias or convulsions that do not result in in-patient hospitalization, or the development of drug dependency or drug abuse.

All SAEs that occur after any patient has been enrolled, before treatment, during treatment, or within 30 days following the cessation of treatment, whether or not they are related to the study drug, must be reported.

Adverse Event Assessment

Intensity

The intensity of each AE is to be assessed by the Investigator according to the NCI CTCAE, Version 4.03. If the AE is not included in the NCI CTCAE, then the Investigator is to determine the intensity of the AE according to the following criteria:

Mild (Grade 1): AE that disappears or is easily tolerated on continuation of study drug.

Moderate (Grade 2): AE sufficiently discomforting to cause interference with usual work activities.

Severe (Grade 3): AE that is incapacitating, with inability to work or perform daily activities.

Life-Threatening (Grade 4): AE that is potentially life-threatening.

Death (Grade 5): Death related to AE.

The causal relationship of each AE to study drug is determined by the Investigator according to best medical judgment, as follows:

Definitely related: This category applies when, after careful medical consideration, there is almost no consideration of other causation.

Probably related: There is a clinically plausible time sequence between onset of the AE and study drug administration. The AE is unlikely to be caused by a concurrent and/or underlying illness, other drugs, or procedures. If applicable, the AE follows a clinically consistent resolution pattern upon withdrawal of study drug.

Possibly related: There is a clinically plausible time sequence between onset of the AE and study drug administration, but the AE could also have been caused by the concurrent/underlying illness, other drugs, or procedures. Information regarding study drug withdrawal may be lacking or unclear. "Possible" should be used when study drug administration is one of several biologically plausible causes of the AE.

Unlikely related: The AE is most likely due to a non-study drug-related cause. However, association with the study drug cannot be completely ruled out.

Unrelated: Another cause of the AE is most plausible and a clinically plausible temporal sequence is inconsistent with the onset of the AE and study drug administration and/or a causal relationship is considered biologically implausible.

If the relationship between the AE/SAE and study drug is determined to be "possible", "probable", or "definite", the event is considered to be treatment-related for the purposes of expedited regulatory reporting and safety analyses.

Recording Adverse Events

Each patient must be carefully monitored for the development of any AEs. This information should be obtained in the form of non-leading questions (e.g., "How are you feeling?") and from signs and symptoms detected during each examination, observations of study personnel, and spontaneous reports from patients.

All AEs (serious and non-serious) spontaneously reported by the patient and/or in response to an open question from study personnel or revealed by observation, physical examination, or other diagnostic procedures are documented in the patient's source documents and recorded in the eCRF. Any clinically relevant (as determined by the Investigator) deterioration in laboratory assessments or other clinical findings is considered an AE and must be recorded in the patient's source documents and in the eCRF.

Information about AEs will be collected from the start of Compound 8 administration at Baseline through 30 days after the last dose of study drug. The AE term should be reported in standard medical terminology when possible. Also when possible, signs and symptoms indicating a common underlying pathology should be noted as one comprehensive event. For each AE, the investigator will evaluate and report the onset, resolution, intensity, causality, action taken, serious outcome (if applicable), and whether or not it caused the patient to discontinue the study.

Reporting Serious Adverse Events

All SAEs (related and unrelated) occurring from screening through the EOT visit (30 days after the last study drug dose) are reported.

The Investigator must report all SAEs to Novella within 24 hours of discovery.

Additional follow-up information, if required or available, should be sent to Novella within one business day of receipt and placed with the original SAE information and kept with the appropriate section of the eCRF and/or study file.

The Sponsor is responsible for notifying the relevant regulatory authorities of certain events. It is the Investigator's responsibility to notify the IRB of all SAEs that occur at his or her study center. Investigators will also be notified of all unexpected, serious, drug-related events (7/15 Day Safety Reports) that occur during the clinical study. Each study center is responsible for notifying its IRBC of these additional SAEs.

Follow-Up of Adverse Events

The Investigator must continue to follow all treatment-emergent SAEs and non-serious AEs considered to be at least possibly related to study drug either until resolution or the event is clearly determined to be stable or due to a patient's stable or chronic condition or inter-current illness(es). This follow-up may extend after the end of the study.

Pregnancy

Study drug must be discontinued immediately in the event of a pregnancy in the patient. The patient should be referred to an obstetrician/gynecologist experienced in reproductive toxicity for further evaluation and counseling.

The Investigator follows the patient/patient's partner until completion of the pregnancy, and must notify the Medical Monitor of the outcome within 5 days. The Investigator provides this information as a follow-up to the initial report.

If the outcome of the pregnancy meets the criteria for immediate classification as an SAE (i.e., spontaneous abortion [any congenital anomaly detected in an aborted fetus is to be documented], stillbirth, neonatal death, or congenital anomaly), then the Investigator should report it as such. Furthermore, all neonatal deaths that occur within 30 days of birth should be reported, without regard to causality, as SAEs. In addition, any infant death after 30 days that the Investigator suspects is related to the in utero exposure to the study drug should also be reported.

Overdose

Signs and symptoms of an overdose should be reported as AEs.

Departures from the protocol is determined as allowable on a case-by-case basis and only in the event of an emergency. The Investigator or other physician in attendance in such an emergency must contact the Medical Monitor as soon as possible to discuss the circumstances of the emergency.

The Medical Monitor, in conjunction with the Investigator, decides whether the patient should continue to participate in the study. All protocol deviations and reasons for such deviations must be documented in the patient's source records.

Protocol Deviations Due to an Emergency or Adverse Event

Departures from the protocol are determined as allowable on a case-by-case basis and only in the event of an emergency. The Investigator or other physician in attendance in such an emergency must contact the Medical Monitor as soon as possible to discuss the circumstances of the emergency.

The Medical Monitor, in conjunction with the Investigator, decides whether the patient should continue to participate in the study. All protocol deviations and reasons for such deviations must be documented in the patient's source records.

Statistics
General Statistical Considerations

Protocol Compound 8-001 is an open-label, Phase 1 study evaluating Compound 8 as monotherapy in patients with advanced solid tumors. The study has 2 phases, a Dose-escalation Phase in patients with advanced solid tumors, and a Cohort-expansion Phase in patients with selected BRCA1 or BRCA2 mutation-positive solid tumors, including pancreatic, prostate, breast, and ovarian cancer.

The objectives of the Dose-escalation phase is to determine the safety, tolerability, DLTs, MTD, plasma PK, preliminary anti-tumor activity and RP2D of Compound 8 administered IV every 21 days as monotherapy in patients with advanced solid tumors. The objectives in the Cohort-expansion phase are to further evaluate the safety, tolerability, and preliminary anti-tumor activity of Compound 8 as monotherapy in four tumor-specific cohorts (pancreatic, prostate, breast, and ovarian).

Descriptive statistics is utilized for all safety, efficacy, and PK parameters. Categorical variables are summarized by frequency distributions (number and percentages of patients), continuous variables are summarized by mean, standard deviation, median, minimum, maximum, and time-to-event variables are summarized using Kaplan-Meier methods and figures for the estimated median time.

All data are summarized by study phase (Dose-escalation and Cohort-expansion), cancer indication (pancreatic, prostate, breast, and ovarian) and Compound 8 dose received. All data collected are also presented in patient listings.

Determination of Sample Size
Dose-escalation Phase

The total number of patients to be enrolled in the Dose-escalation Phase is dependent upon the observed safety profile, which determines the number of patients per dose cohort, as well as the number of dose escalations required to achieve the MTD of Compound 8 and establish the RP2D. One patient is enrolled in each Single-patient Cohort and 3 to 6 patients are enrolled in each Standard Cohort, based on a standard Phase 1 dose escalation scheme. Each patient participates in only 1 dose cohort.

The operating characteristics of the Dose-escalation phase of this study are shown in Table 28.

the tolerability and preliminary activity of Compound 8 in patients with distinct tumor types.

Replacement of Patients

Patients who are lost to follow-up or withdraw consent for study participation prior to receiving Compound 8 or who, in the Dose-escalation Phase, withdraw in C1 for reasons other than DLT may be replaced.

Populations for Analysis

The intent-to-treat (ITT) principal will be followed for the safety and efficacy populations. This is defined as all patients enrolled into the study and who received any amount of Compound 8. PK analyses is performed on the PK population, defined as all patients who receive any amount of Compound 8 and have sufficient data for PK analysis.

Patient Disposition

Data tabulations summarize the following patient numbers:
  Enrolled;
  Compound 8 dose received;
  Evaluable for safety and efficacy;
  Protocol violations;
  Protocol completions;
  Withdraw from study due to: AE; Investigator request; Withdrew consent; Lost to Follow-up; Other reasons, as collected in the eCRF.

Patient Characteristics

Demographic and baseline characteristics of patients are summarized using descriptive statistics: Age; Sex; Race; Ethnicity; Baseline ECOG PS; Primary diagnosis; Disease stage at diagnosis and baseline; Prior therapies, including systemic therapies, radiation, and surgeries; Other baseline characteristics, as collected in the eCRF.

Concomitant Medications

The number and proportion of patients in the Safety analysis set using different concomitant medications are tabulated and summarized by WHO Drug anatomical, therapeutic, chemical (ATC) class and preferred term.

Efficacy Analysis

Evidence of preliminary anti-tumor activity is assessed by the objective response, as defined by RECIST, version 1.1. This is used to summarize the overall response rate (CR+

TABLE 28

| Probability of Dose Escalation | | | | | | | | | | | |
|---|---|---|---|---|---|---|---|---|---|---|---|
| | Background Toxicity Rate | | | | | | | | | | |
| | 1% | 5% | 10% | 20% | 30% | 40% | 50% | 60% | 70% | 80% | 90% |
| Probability of dose escalation | 99.9% | 97% | 91% | 71% | 49% | 31% | 17% | 8% | 3% | 1% | 0.1% |

For example, assuming a true DLT rate of 5%, there is a 97% probability of dose escalating. Conversely, for a true DLT rate of 50%, the probability of dose escalating is 17%.

A total of 6 to 10 patients are treated at the MTD or RP2D to provide further characterization of the safety, tolerability, and PK of Compound 8.

Cohort-Expansion Phase

No formal sample size calculations were performed. A total of up to 60 patients are enrolled in the Cohort-expansion Phase. This includes 10-15 patients in each Expansion Cohort 1, 2, 3A, and 3B. The sample size of at least 10 patients per cohort was not chosen to meet a specific statistical threshold but is considered sufficient to evaluate PR), as well as the rates for the individual categories of response, (i.e., CR, PR, SD, and PD).

Safety Analysis

All patients who receive any amount of Compound 8 are included in the final summaries and listings of safety data.

Summary tables present the number of patients observed with treatment-emergent adverse events (TEAEs) and corresponding percentages, where treatment-emergent is defined as any AE that occurs after administration of the first dose of study drug and through 30 days after the last dose of study drug, any event that is considered study drug-related regardless of the start date of the event, or any event that is present at baseline but worsens in intensity or is subsequently considered study drug-related by the Investigator.

The denominator used to calculate incidence percentages consists of patients receiving any amount of Compound 8. Within each summary table, the AEs are categorized according to the Medical Dictionary for Regulatory Activities (MedDRA) system organ class and preferred term. Additional subcategories are based on event intensity (severity graded according to CTCAE, version 4.03) and relationship to study drug.

Deaths, SAEs, and TEAEs leading to study drug discontinuation are tabulated on a per-patient basis, as warranted by the data.

For the Dose-escalation phase, the DLTs, MTD, and RP2D are identified.

Change from baseline in clinical laboratory parameters is summarized across time on study. Furthermore, the frequency of laboratory abnormalities by maximum post-baseline CTCAE grade are tabulated by cycle and overall for selected laboratory parameters to include at least hemoglobin, white blood cell count, ANC, lymphocytes, platelet count, AST, ALT, bilirubin, creatinine, alkaline phosphatase, and electrolytes. Shift tables also may be produced for these parameters based on the baseline CTCAE grade and the maximum CTCAE grade by cycle and overall.

Changes in vital sign parameters (including systolic and diastolic blood pressure and heart rate) and body weight are summarized over time, and any abnormal values will be tabulated. The proportions of patients with treatment-emergent clinically significant ECG abnormalities are tabulated, and changes in ECG findings are presented in data listing format.

ECOG performance status is summarized by cycle and worst status overall; ECOG performance status is presented in data listing format.

Additional safety analyses may be determined at any time without prejudice, in order to most clearly enumerate rates of toxicities and to define further the safety profile of Compound 8.

Pharmacokinetic Analysis

PK is characterized by fitting an appropriate compartmental model to the complete set of data for each patient. The model to be used is determined from the data and is parameterized in terms of clearance(s) and volumes of distribution.

EQUIVALENTS AND SCOPE

While several embodiments of the present teachings have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present teachings. More generally, those skilled in the art will appreciate that all parameters, dimensions, materials, and configurations described herein are meant to be exemplary and that the actual parameters, dimensions, materials, and/or configurations will depend upon the specific application or applications for which the teachings of the present teachings is/are used. Those skilled in the art will recognize, or be able to ascertain using no more than routine experimentation, many equivalents to the specific embodiments of the present teachings described herein.

It is, therefore, to be understood that the foregoing embodiments are presented by way of example only and that, within the scope of the appended claims and equivalents thereto, the present teachings may be practiced otherwise than as specifically described and claimed. The present teachings are directed to each individual feature and/or method described herein. In addition, any combination of two or more such features and/or methods, if such features and/or methods are not mutually inconsistent, is included within the scope of the present teachings.

The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

What is claimed is:

1. A pharmaceutical composition comprising Compound 8:

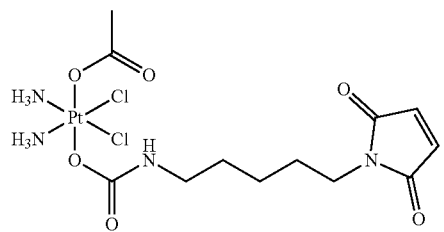

or a pharmaceutically acceptable salt thereof and a pharmaceutically acceptable excipient, wherein the pharmaceutical composition has a pH of about 4 to about 5, wherein the pharmaceutical composition further comprises a citrate buffer, and wherein the pharmaceutically acceptable excipient is mannitol.

2. The pharmaceutical composition of claim 1, wherein the concentration of Compound 8 is 3-5 mg/mL.

3. The pharmaceutical composition of claim 2, wherein the concentration of Compound 8 is 5 mg/mL.

4. The pharmaceutical composition of claim 1, wherein the pharmaceutical composition has a pH of about 4 or about 4.25.

5. The pharmaceutical composition of claim 1, the buffer has a concentration of about 0.5 mM to about 100 mM.

6. The pharmaceutical composition of claim 1, wherein the citrate buffer comprises sodium citrate and citric acid, or citric acid and sodium hydroxide.

7. The pharmaceutical composition of claim 1, wherein the excipient has a weight percent of about 0.5% (w/w) to about 20% (w/w).

8. The pharmaceutical composition of claim 1, wherein the excipient has a weight percent of about 2.5% (w/w).

* * * * *